(12) United States Patent
Andreae et al.

(10) Patent No.: US 9,408,569 B2
(45) Date of Patent: Aug. 9, 2016

(54) VASCULAR BLOOD SAMPLING CATHETER

(71) Applicant: PROVAZO LLC, Charlottesville, VA (US)

(72) Inventors: Andrew E. Andreae, Orlando, FL (US); Timothy J. Higgins, Springfield, VA (US); Jessica L. Ungerleider, La Jolla, CA (US); Peter Jacob Neems, Charlottesville, VA (US)

(73) Assignee: ProVazo LLC, Charlottesville, VA (US)

( * ) Notice: Subject to any disclaimer, the term of this patent is extended or adjusted under 35 U.S.C. 154(b) by 0 days.

(21) Appl. No.: 14/069,539

(22) Filed: Nov. 1, 2013

(65) Prior Publication Data

US 2014/0128774 A1    May 8, 2014

Related U.S. Application Data

(60) Provisional application No. 61/722,160, filed on Nov. 3, 2012.

(51) Int. Cl.
*A61B 5/00* (2006.01)
*B65D 81/00* (2006.01)
(Continued)

(52) U.S. Cl.
CPC ......... *A61B 5/150992* (2013.01); *A61B 5/1405* (2013.01); *A61B 5/153* (2013.01); *A61B 5/155* (2013.01); *A61B 5/150099* (2013.01); *A61B 5/150221* (2013.01); *A61B 5/150396* (2013.01); *A61B 5/150511* (2013.01); *A61B 5/15003* (2013.01); *A61B 5/150358* (2013.01); *A61B 5/150633* (2013.01); *A61B 5/150748* (2013.01); *A61B 5/150755* (2013.01);
(Continued)

(58) Field of Classification Search
CPC ....... A61B 5/1405; A61B 5/155; A61B 5/153
USPC .......................... 600/573, 576, 577, 580, 581
See application file for complete search history.

(56) References Cited

U.S. PATENT DOCUMENTS 4,700,694 A * 10/1987 Shishido ...................... 600/104
4,705,501 A    11/1987 Wigness
(Continued)

FOREIGN PATENT DOCUMENTS

| DE | 3117159 | 11/1982 |
|---|---|---|
| WO | 2007/050788 | 5/2007 |
| WO | 2011/157638 | 12/2011 |

OTHER PUBLICATIONS

Office Action dated Jul. 17, 2014 from Corresponding U.S. Appl. No. 14/069,627.
(Continued)

*Primary Examiner* — Max Hindenburg
*Assistant Examiner* — Jonathan M Foreman
(74) *Attorney, Agent, or Firm* — McDermott Will & Emery LLP

(57) ABSTRACT

A liquid sampling catheter contains a lumen filled by a sampling cannula with a hollow lumen and either a closed or open distal tip. Attached to the proximal end of the device is a modular blood storage component. The sampling stick slides through the patient's skin or through a seal and in-dwelling lumen on a corresponding sampling hub to sample blood from a patient. This embodiment establishes a simple, standardized, and quick procedure for sampling small amounts of bodily liquids such as blood for a variety of analyte tests.

60 Claims, 44 Drawing Sheets

(51) Int. Cl.
*A61B 5/15* (2006.01)
*A61B 5/153* (2006.01)
*A61B 5/155* (2006.01)
*A61M 5/158* (2006.01)
*A61M 39/06* (2006.01)

(52) U.S. Cl.
CPC .............. *A61M 5/158* (2013.01); *A61M 39/06* (2013.01); *A61M 2005/1586* (2013.01)

(56) References Cited

U.S. PATENT DOCUMENTS

| | | | |
|---|---|---|---|
| 5,009,391 A * | 4/1991 | Steigerwald | A61M 39/0613 137/849 |
| 5,224,938 A | 7/1993 | Fenton | |
| 5,269,764 A | 12/1993 | Vetter et al. | |
| 5,405,323 A * | 4/1995 | Rogers et al. | 604/508 |
| 5,556,381 A | 9/1996 | Ensminger | |
| 5,702,418 A | 12/1997 | Ravenscroft | |
| 5,713,858 A | 2/1998 | Heruth | |
| 6,080,138 A | 6/2000 | Lemke et al. | |
| 6,344,033 B1 | 2/2002 | Jepson et al. | |
| 6,908,459 B2 | 6/2005 | Harding et al. | |
| 6,916,309 B2 | 7/2005 | Fangrow, Jr. | |
| 7,008,404 B2 | 3/2006 | Nakajima | |
| 7,670,320 B2 | 3/2010 | Iwase et al. | |
| 7,713,250 B2 | 5/2010 | Harding et al. | |
| 7,717,882 B2 | 5/2010 | Harding | |
| 7,846,139 B2 | 12/2010 | Zinn | |
| 8,057,439 B2 | 11/2011 | Di Fiore | |
| 8,262,625 B1 | 9/2012 | Fischell et al. | |
| 8,366,685 B2 | 2/2013 | Devgon | |
| 8,506,533 B2 | 8/2013 | Carlyon et al. | |
| 2002/0099267 A1 * | 7/2002 | Wendlandt et al. | 600/173 |
| 2002/0120215 A1 | 8/2002 | Craword | |
| 2005/0096609 A1 | 5/2005 | Maginot et al. | |
| 2005/0148823 A1 | 7/2005 | Vaugh et al. | |
| 2005/0197663 A1 | 9/2005 | Soma et al. | |
| 2006/0155209 A1 | 7/2006 | Miller | |
| 2007/0100295 A1 * | 5/2007 | Belley et al. | 604/246 |
| 2009/0125037 A1 * | 5/2009 | Goto | 606/140 |
| 2010/0160863 A1 | 6/2010 | Heuser | |
| 2010/0179563 A1 | 7/2010 | Skakoon | |
| 2010/0217155 A1 | 8/2010 | Poux | |
| 2011/0163094 A1 * | 7/2011 | Arney | B65D 39/00 220/212 |
| 2011/0313354 A1 | 12/2011 | Hennessy | |
| 2012/0157968 A1 | 6/2012 | Eldredge et al. | |
| 2012/0191010 A1 | 7/2012 | Cabot | |
| 2012/0277630 A1 * | 11/2012 | Devgon | 600/581 |
| 2013/0237925 A1 | 9/2013 | Trainer et al. | |

OTHER PUBLICATIONS

International Search Report and the Written Opinion dated Aug. 15, 2014 from Corresponding PCT Application No. PCT/US2014/035944.

Advisory Action dated May 7, 2015 from corresponding U.S. Appl. No. 14/069,627.

\* cited by examiner

VASCULAR BLOOD SAMPLING CATHETER

RELATED APPLICATION DATA

This application claims priority from U.S. Provisional Patent Application Ser. No. 61/722,160, filed 3 Nov. 2012.

FEDERALLY SPONSORED RESEARCH

Not Applicable

SEQUENCE LISTING OR PROGRAM

Not Applicable

BACKGROUND OF THE INVENTION

1. Field of the Invention

This invention relates to liquid sampling catheters such as vascular catheters, specifically in their use to sample volumes of patient liquids, including blood, in clinical settings.

2. Background of the Art

The embodiments described herein relate generally to medical devices. More particularly, the present disclosure relates to a blood sampling device and associated method via a vascular access device. Blood sampling is a common medical procedure involving the withdrawal of at least a drop of blood from a patient. Hospitals, medical clinics, emergency rooms, and health care providers commonly sample liquid from patients either by lancet fingerstick or heel stick devices, venipuncture, or central IV lines. Once collected, blood samples are analyzed via a variety of chemistry tests.

Blood samples are commonly taken to determine the physiological and biochemical state of a patient, and are either analyzed in a laboratory, a distance away from a patient, or at the point of care, near the location of the patient. Clinicians then use this analysis to determine the disease state of a patient, mineral concentrations, organ function, and clinical treatment effectiveness. One example of a common blood test is a point of care blood glucose test, where blood is extracted via a lancet fingerstick, and mechanically transferred onto a testing strip to determine blood glucose values. In other tests, clinicians draw a vial of blood from a venous or arterial source, and then that sample is analyzed in a central laboratory for tens to hundreds of biochemical tests including gas electrolyte levels, protein analysis, and cholesterol quantification, among others.

Despite rapid advancements in both laboratory analysis and point of care testing, current methods of blood sampling have remained relatively unchanged. Each of these methods presents their own unique challenges and issues. Lancets sample capillary blood, which has a higher margin of error in metabolic measurements. These devices also cause discomfort as patients are continually pricked. Venipuncture, the most common method of sampling, when done frequently can cause significant trauma to the venous system and impede the integrity of a patient's veins. Additionally, venipuncture is a manual, labor-intensive process creating significant labor costs by requiring specially trained venipuncture teams within hospitals. It also presents a much higher level of discomfort than lancets. Central line sampling is a more complicated procedure with multiple steps and can be prone to error. Using the same site for infusion and sampling causes an increased chance of sample contamination. Drawing blood from central lines is also known to increase the risk of central line-associated blood stream infections. These blood sampling processes are labor and time intensive, and require multiple devices throughout the sampling process. Furthermore, these methods have many clinical and practical problems associated with their use. Accordingly, there is a need for more efficient and accurate blood sampling devices.

U.S. Pat. No. 8,366,685 (Devgon) describes systems and methods for phlebotomy through a peripheral IV catheter. An actuator is used to advance and retract a sampling cannula that engages a peripheral intravenous line.

US Patent Application (abandoned) Pub. No.: US 2002/0120215 A1, describes a BLOOD COLLECTION SET WITH RETRACTABLE NEEDLE (Crawford) that provides a retractable sheath over a needle sampler, the sheath having horizontal stabilizing wings.

SUMMARY OF THE INVENTION

An embodiment of the present invention provides a medical blood sampling device and related method for sampling of blood from the vascular system of the patient. An embodiment of the present invention provides a medical blood sampling device and related method that, among other things, facilitates quick, simple, and standardized sampling of the blood sources considered most clinically acceptable. This innovation improves the accuracy, patient comfort, and convenience associated with blood draws.

The ability to sample blood accurately and noninvasively is imperative in conserving blood and yielding more accurate analyte test results, which leads to improvements in patient outcomes and comfort. The device herein established will provide a standardized and simple means to obtain these blood samples. This will improve patient comfort and potentially their overall clinical outcome.

This technology is provided by structures and/or methods that may implement the sampling of liquids from within a patient with at least steps of:

a) inserting a sampling device into a region of a patient, the sampling device comprising a delivery catheter and within a lumen of the delivery catheter is a sampling cannula having a longitudinal axis, the delivery catheter being moveable over the sampling cannula by retraction or extension of the delivery catheter sheath(s);

b) moving the delivery catheter towards a target area within the patient (which may contain a distal volume of material from which a sample is to be taken) causes the delivery catheter to press against the patient or sampling hub thereby causing the sheath(s) of the delivery catheter to retract as the delivery catheter advances forward which exposes the sampling cannula to the target area within the patient c) allowing liquid within the target area within the patient into the sampling cannula; and d) withdrawing the liquid from the sampling cannula to create a liquid sample.

A general description of the sampling device could include a delivery catheter and within a lumen of the delivery catheter is a sampling cannula having a longitudinal axis, the delivery catheter being moveable over the sampling cannula by retraction or extension. The delivery catheter could also enter the target area through a sampling hub (especially as described herein) or directly through the patient's skin.

A sampling hub directs a medical device towards a target area. The hub may have some of: a hub body; a lumen passing between openings at the front end (distal end) or bottom of the hub and the rear end (proximal end), the lumen allowing for passage of an elongate element through the entire lumen; in one optional structural embodiment, the bottom of the hub body may be flat (or any convenient configuration, including conformable, curved, friction-providing surface, absorbent surface, moisture-penetrable surface, antimicrobial surface, breathable surface, etc.); the top of hub body preferably is sloped downwardly although it may be level or even slope upwardly or curve; the lumen is preferably sloped downwardly to enable guidance of the elongate body towards the target area, although horizontal alignment is exemplified herein; and an area surrounding the opening of the lumen at the rear end configured to receive a support for the elongate element, the support for the elongate element having a diameter in the support larger than a diameter of the elongate element.

BRIEF DESCRIPTION OF THE FIGURES

In the drawings, closely related figures have the same number but different alphabetic suffixes. These drawings only depict typical embodiments of the invention and are not intended to be considered the only possible embodiments or to limit the scope of the invention.

DETAILED DESCRIPTION OF THE INVENTION

Figure 1:
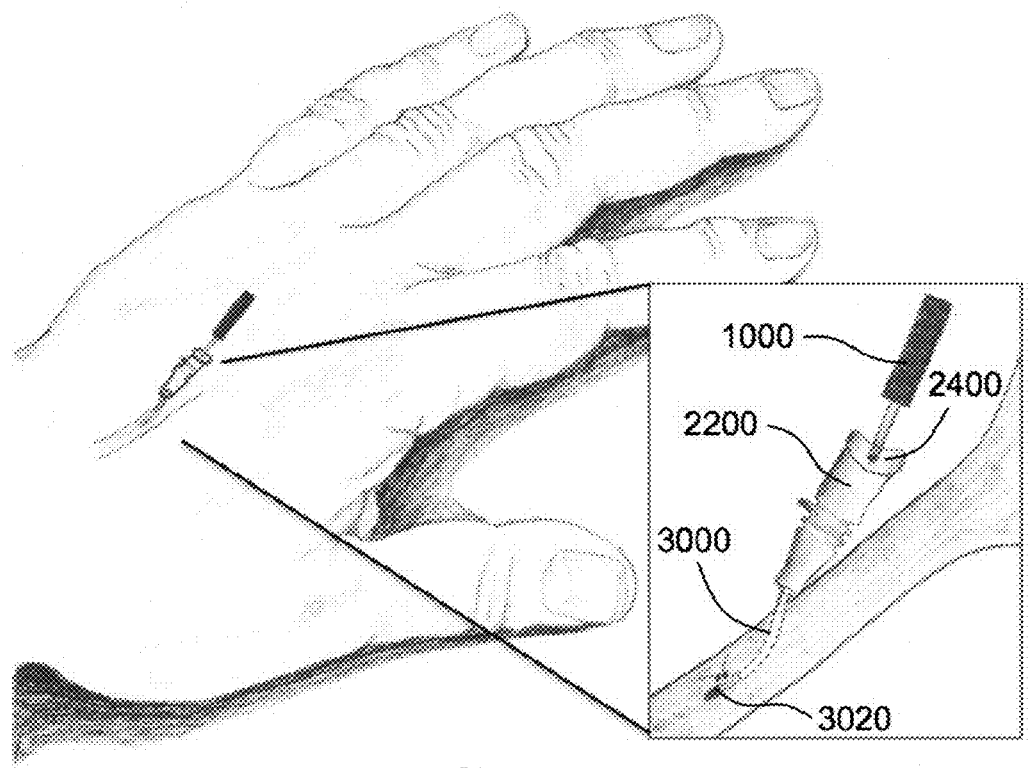
FIG. 1 shows the operation of the device on a patient according to a representative embodiment.

There are at least two unified aspects of the present technology, a method and the device unique to the implementation of that method. The method may be practiced by the described device. A sampling device, such as a solids, tissue or liquid sampling device, such as a blood sampling device or an arterial or intravenous blood sampling device useful within the practice of the present technology would include at least a delivery catheter. Within a lumen of the delivery catheter is a sampling cannula having a longitudinal axis. The delivery catheter is moveable over the sampling cannula by retraction or extension of the delivery catheter sheath(s). The sampling device, by way of example, may provide two extreme relative positions of the delivery catheter and the sampling cannula (and intermediate functional positions may also be available). A first extreme position might be where the delivery catheter shields at least the majority (or all, including the majority or all number of ports or the majority or all areas of entry into ports) of sampling ports in the sampling cannula from exposure to an adjacent environment along the longitudinal axis of the sampling cannula and a second extreme position wherein the delivery catheter sheath(s) has moved rearwardly and exposed to the adjacent environment the majority of sampling ports in the sampling cannula. The sampling ports may be present along the longitudinal axis of the sampling cannula (and one or more may be forward at the tip of the sampling cannula) and at least some of the ports may be perpendicular to the longitudinal axis of the sampling cannula. In the first extreme position, at least 50% of the sampling ports are shielded from the adjacent environment and in the second extreme position, at least a greater number of the sampling ports are exposed to the adjacent environment. The sampling cannula may support a sampling hub that surrounds the front end or distal end of the sampling cannula, the sampling hub providing a sealed insertion port or split septum physically insulating the external environment from the adjacent environment, the sampling hub physically insulating the intake ports in the sampling cannula from exposure to an adjacent environment. As noted, the two extreme relative positions of the delivery catheter and the sampling cannula may be available, a first extreme position where the delivery catheter shields at least the majority of sampling ports in the sampling cannula from exposure to an adjacent environment along the longitudinal axis of the sampling cannula and a second extreme position wherein the delivery catheter sheath(s) has moved rearwardly and exposed to the adjacent environment the majority of sampling ports in the sampling cannula, and wherein movement of the delivery catheter from the first extreme position to the second extreme position causes the sampling hub to cover the longitudinal axis of the sampling cannula and expose at least some of the intake ports in the sampling cannula to the adjacent environment. The sampling cannula may have or create a volume therein to hold liquid samples, and there would be a port at a proximal end of the volume to allow controlled passage of liquid within the volume to be withdrawn into a modular sampling component. Otherwise, the entire sampling cannula would be physically removed from the sampling device and transported for analysis of the liquid sample after removal. It is also possible for the sampling cannula to be a solid probe or collection tool. In these embodiments the probe may be used to deliver an electric shock or sensor to a region. A solid collection tool may also be used to collect a solid sample (i.e., biopsy) from the target area. The sensor and some other tools would require electrical leads to the tool from a power source and/or a communication link to a processor or other signal receiver. The sampling device may include a construction wherein a proximal support element is present to resist forward and rearward movement of the sampling cannula relative to the forward and rearward movement of the delivery catheter after the delivery catheter has been positioned against a sampling hub or body of a patient. Such a proximal support element may be a locking or blocking edge or element, a biasing spring or lever, or other physical restraint. In some embodiments, the delivery catheter may enter the body of the patient. Upon withdrawal of the delivery catheter and retention of a forward position by the sampling cannula, a chamber is formed at a proximal end of the sampling cannula and reduced pressure or other extraction methods are applied within a volume of the sampling cannula to draw liquid samples from the adjacent environment into the volume through the port(s) exposed to the adjacent environment which includes the target area.

A method of sampling liquids from within a patient using the described device could include steps of:
  a) inserting a sampling cannula into a target area of a patient, by means of a delivery catheter and within a lumen of the delivery catheter is a sampling cannula having a longitudinal axis, the delivery catheter being moveable over the sampling cannula by retraction or extension of the delivery catheter sheath(s);
  b) moving the delivery catheter towards a target area within the patient causes the delivery catheter to press against the patient or sampling hub thereby causing the sheath(s) of the delivery catheter to retract as it advances forward which exposes the sampling cannula to the target area within the patient;
  c) allowing liquid within the target area of the patient into the sampling cannula; and
  d) withdrawing the liquid from the sampling cannula to create a liquid sample.

The method may be practiced by the sampling device being inserted through the skin into the patient, the sampling device being positioned at a forward location within the patient, the delivery catheter sheath(s) being withdrawn from the forward location, and the sampling cannula advancing to or towards the forward location. A support element within the sampling device supports a proximal end of the sampling cannula so as to resist withdrawal from the forward location by any friction between the delivery catheter and the sampling cannula. In the method, the sampling cannula may have at least one liquid inflow port (or multiple ports) along its longitudinal axis and movement of the delivery catheter sheath away from the distal volume increases exposure of at least one delivery port (or the multiple ports) to liquid within the target area of the patient. In another embodiment of a method, the sampling cannula supports a sampling hub that surrounds a front end of the sampling cannula, the sampling hub providing a sealed insertion port physically insulating the sampling cannula from liquid at the forward position within the patient, and the sampling hub is withdrawn over the sampling cannula before the liquid is withdrawn. The withdrawal of the delivery catheter may be simultaneously or independent of the withdrawal of the sampling hub to expose the sampling cannula to liquid within the patient.

One aspect of the present technology includes a guiding and directing system for lumen-containing medical devices such as catheters, syringes or samplers. The directing system can be used to introduce or remove samples, especially liquid samples from a patient. The patient may be any animal, including humans. The guide, referred to herein as a hub, can perform numerous functions. One primary function is to provide a stable platform through which the medical device can be directed and then withdrawn. The hub is positioned on a surface of the patient, the medical device introduced through a lumen in the hub, a procedure performed, and the medical device and hub withdrawn, together, or the medical device first and later the hub. The hub may be used in multiple procedures, either left in place (typically adhesively secured by tape or gel or dissolving stitch or other temporary securing element) or removed, sterilized and later replaced. The hub may be composed of plastic, elastomeric, metal, composite materials, ceramics, cellulosic materials and/or combinations of these materials. The surface of the patient is an exterior portion of the patient outside of a volume from which liquid is to be sampled, which may be in the vicinity of a vessel (vein or artery) or near any cavity, swelling, mass, liquid volume and the like from which a sample is desired to be taken.

A general description for a sampling hub for directing a medical device towards a target area according to the present invention follows. The hub may have at least some of:
  a) a lumen passing between openings at, near or toward the front end (distal end) or bottom of the hub and the rear end (proximal end), the lumen allowing for passage of an elongate element through the entire lumen, to the target area away from the near end, towards the middle of the hub, past the middle of the hub, or at or near the front of the hub;
  b) the bottom of the hub body comprises a flat, near flat, concave or less preferred a convex surface;
  c) the top of hub body preferably is sloped downwardly so as to provide a thicker hub body at the rear end where the elongate body would enter the lumen, although a relatively horizontal path can be provided, with the medical device tilting or curving down into the patient. A thinner hub body may be present at the front end of the hub body where the elongate element would exit the lumen, although a less preferred embodiment would have a relatively uniformed thickness in the hub from the rear to the front (although some extending elements, such as grips, clips or stabilizing wings may be present extending from the hub body);
  d) the lumen is, as previously indicated, preferably sloped downwardly to enable guidance of the elongate body towards the target area; and
  e) an area surrounding the opening of the lumen at the rear end configured to receive a support for the elongate element, the support for the elongate element having a diameter in the support larger than a diameter of the elongate element.

In another variation on the underlying generic design of the hub, the lumen has a distal end that extends out of the hub and is configured to allow that distal end of the lumen to penetrate skin of the patient. The external component of the distal end of the lumen may be sufficiently small and rigid to be able to penetrate skin without need of the strength or sharpness of the elongate element. The external component may also be soft enough to reside inside the target area for an extended period of time. In this embodiment, the sampling hub will be paired with an insertion needle to aid in the introduction of the external component into the target area. The external component of the lumen may be made of the same or different materials than the other components of the hub.

The hub may be constructed in a number of different design formats that are within the scope of the present generic invention. For example, the simplest way in which the hub can be manufactured is as a single, integral sampling hub (in a single molding step, or with individual sections separately molded then permanently secured together). However, one optional construction within the scope of this invention is to have (at least) two separate segments of the hub which can be integrated during use. One example of this multi-subcomponent hub would be to have a sturdy lumen element, the distal end of that lumen being capable of manual insertion into the patient. The distal end may also be soft enough to reside inside the target area for an extended period of time. In this embodiment, the distal end will be paired with an insertion needle to aid in the introduction of the distal end into the target area. The proximal end of that lumen could be configured to couple with a larger and more substantive hub body. The two subcomponents could be secured together after the lumen had been inserted into the patient. The second hub body component adds substance and stability to the lumen and helps stabilize its insertion.

The bottom of the sampling hub is preferably wider than the top of the sampling hub to provide some stability when positioned against the patient. The bottom of the hub preferably extends outwardly from the hub body to provide at least one and preferably two stabilizing panels or wings. The wings may be flexible in order to allow them to fold upwardly against the hub during its placement on or insertion into the patient and to allow them to fold downwardly to contour to the patient to hold the hub in place. If the flat bottoms (or other bottom configurations) are more flexible, they will themselves conform better to the patient while still applying some pressure to the patient. The greater flexibility will allow single size sampling hub to have utility with a wider range of dimensions on patients. As patients vary in size, this is a desirable feature. The composition of the sampling hub will vary upon selection of its desired physical properties, and its intended durability, whether to be disposable or reusable. Material compositions may be polymers (thermoplastic or thermoset polymers), filled polymers, reinforced polymers, ceramics, composites, metals, rigid paper, reinforced paper, polymer embedded paper, wood and combinations thereof. In one preferred embodiment, the hub is configured where the front end of the hub has a viewing area through which a front end of the elongate element (e.g., the medical device) may be seen during forward movement though the hub. In the embodiments of the device where the distal lumen penetrates the patient's skin and the sampling hub is paired with an insertion needle, this viewing area may also be used to view this point of insertion, observation of the entry area or site for other effects such as trauma or infection or adverse patient reactions (e.g., allergic reactions).

The hub is particularly useful in combination with the above described sampling device wherein the elongate element is carried by a sheath and/or delivery catheter slideable over the elongate element nestled within the hub, with the elongate element extended into the lumen, and the sheath stabilized within the area surrounding the opening of the lumen at the rear end (proximal end) of the hub configured to receive a support for the elongate element. When the sheath/delivery catheter butts against the inner part of the area surrounding the opening of the lumen, the sheath withdraws from over the elongate body or introducing element by forces transmitted against the sheath, but not transmitted to the elongate element.

In one construction, the rear end of the sampling hub may have a flat or relatively flat surface and the area surrounding the opening of the lumen is geometric to receive the medical device, as with a square, rectangular, round, oval, or other geometric recess in the flat surface. The hub may be used in a method for collecting a sample from a target area comprising positioning a front end of a hub sampling device adjacent to or within the target area, the hub sampling device being the device and system described above. In the method, the elongate element (sampling device) may be a collection element or probe and the target area comprises a live patient. The sampling tool enters the live patient through the sampling hub at the target area and a forward tip of the tool extends into the live patient. In some embodiments, the front end of the sampling hub has a viewing area where the front end of the elongate element may be seen and an operator may view the front end of the forward tip of the tool as it penetrates the skin of the patient or progresses towards a target area (if it is not actually seen at the target area). Additionally, this viewing area can be used to inspect the site where the sampling hub lumen penetrates the patient skin to determine if there is any inflammation or harm to the patient. The elongate element may be carried by a sheath slideable over the elongate element, the sheath is nestled within the sampling hub, with the elongate element extended into the lumen, and the sheath is stabilized within the area surrounding the opening of the lumen at the rear end configured to receive a support for the elongate element. As noted above in the method, nestling of the sheath within the sampling hub causes the elongate element to slide within the sheath and extend forward out of the sheath.

The lumen may be constructed to provide preliminary protection to the elongate element from the target area. The tip of the lumen may have a protective, at least partially (if not completely) closed, cover or valve, or series of valves. This valve or valves may also be used to prevent backflow of liquid from the target area into lumen. The valve(s) is naturally in a closed position. The lumen may have a valve(s) thereon, the valve(s) being configured to be opened when an element proceeds through the lumen to exert internal force against the valve(s). Force against the interior of the valve(s) opens moveable elements in the valve(s). These may be flanges, flaps, semicircle, spherical sections, or other segments of the valve(s) that can separate to provide an opening when the elongate element is pressed through the interior of the lumen to provide opening force against the valve(s). While the valve is opened, the newly created opening is completely filled by the elongate element preventing any fluid from entering the lumen of the hub. The open valve(s) may have natural elasticity or elastic memory in the materials to allow or cause the open valve(s) to close when the elongate element is retracted backwards past the valve(s). If there is no natural elasticity or internal forces that would close the valve(s) once the elongate element is retracted, retraction of the lumen may cause friction forces across the open valve(s) that are exerted by the withdrawal (as through tissue) to close the open valve(s).

In the following description of the figures, like or repeated numbers represent like or repeated elements, even when the same numbers are used in different figures. The following is a number-element key to a review of the figures.

ELEMENT NUMBERS

1000—Delivery Catheter
1050—Retractable Parts of the Delivery Catheter
1100—Collection mechanism
1110—Luer lock
1112—Luer Slip
1120—Vacutainer version
1122—Rubber covering of sampling cannula end
1124—Vacutainer Chamber
1130—Reverse syringe
1132—Rubber cover of delivery catheter proximal part
1133—Rubber cover hole
1134—Cover/Reverse Plunger
1135—Large Cover
1136—Empty Space where blood is collected
1137—Reverse plunger with probe attached
1138—Cover Ridge
1139—Finger Tab to slide up Cover
1140—Reverse syringe container access
1142—Door
1144—Slot
1150—Pipette bulb
1152—Capillary Action
1160—Incorporated chemistry
1200—Delivery Catheter Proximal Part
1201—Large Delivery Catheter Proximal Part
1202—Distal end of delivery catheter proximal part
1210—Internal chamber where delivery catheter retracts
1212—Proximal end of internal chamber
1220—Ridge between click mechanisms
1230—Proximal end of the proximal part
1232—Rubber cover holder
1240—Spring
1250—Side Port Embodiment
1252—Side Access Port
1300—Delivery catheter proximal sheath
1310—Internal chamber where delivery catheter retracts
1312—Proximal end of internal chamber of the proximal sheath
1320—Clicking mechanisms
1322—Proximal click
1324—Distal click
1326—Ridge between clicks
1330—Proximal end of proximal sheath
1340—Distal end of proximal sheath
1400—Delivery catheter distal sheath
1402—Proximal end of distal sheath
1410—Distal end of the distal sheath
1412—Opening at the distal end of the distal sheath
1414—Internal chamber for sampling cannula
1420—Clicking mechanisms
1422—Proximal click
1424—Distal click 1430—Venting slots
1440—Cap
1450—Protective Barrier
1460—Guide wire
1462—Distal End of Guide Wire
1464—Proximal End of Guide Wire
1500—Sampling cannula
1510—Proximal end of the sampling cannula
1512—Vacutainer needle
1520—Distal end of the sampling cannula
1530—Rounded tip
1532—Opening in rounded tip
1534—Multiple openings in rounded tip
1540—Sampling Cannula Hole
1541—Through holes
1542—Side holes
1550—Valve on the Side of the Sampling Cannula
1552—Valve folds inwards
1554—Proximal end of the valve folds downwards
1560—Pointed needle tip
1562—Non-coring needle tip
1600—Syringe Embodiment of Delivery Catheter
1610—Syringe Plunger
1612—Proximal End of Syringe Plunger
1614—Rubber Cover Holder Syringe Plunger
1616—Cannula Base Holder
1617—Small Plunger Embodiment
1618—Large Plunger Embodiment
1620—Rubber Stopper for Syringe Plunger
1630—Plunger Housing
1631—Blood Collection Chamber
1632—Cannula base chamber
1633—Cannula chamber
1634—Air holes to vent air in collection chamber
1635—Ridge to prevent further insertion
1636—Air venting path
1637—Distal End of Plunger Housing
1640—Syringe Embodiment Sampling Cannula
1642—Cannula Base
1644—Proximal end of sampling cannula
1646—Distal end of sampling cannula
1650—Cover for Syringe Embodiment
1652—Cover Cavity
1700—Probe
1710—Probe proximal end
1720—Probe distal end
2200—Sampling Hub
2202—Internal chamber for sampling hub lumen
2204—Proximal end chamber for sampling hub lumen
2206—Distal end chamber for sampling hub lumen
2208—Internal probe alignment chamber
2210—Internal chamber for sampling hub proximal valve
2212—Bottom of sampling hub body
2214—Proximal end
2216—Distal end
2240—Traditional sampling hub shape
2242—Distal end sampling hub
2244—Primary finger ridge
2246—Secondary finger ridge
2248—Proximal finger depression
2250—Central finger depression
2252—Distal finger depression
2260—Sampling Hub Securement Device
2262—Wings
2264—Bottom of wings
2270—Sampling Hub Visualization
2272—Clear panels
2274—Visualization through hole window
2280—Two part Catheter
2282—Proximal sampling hub addition
2284—Distal sampling hub insertion component
2285—Proximal end of the distal sampling hub insertion component
2286—Two part locking knob
2288—Distal half alignment ledge
2290—Proximal half alignment ledge receiver
2290—Generic IV Catheter
2400—Sampling Hub Proximal Valve
2410—Split septum
2412—Slit
3000—Sampling Hub Lumen
3010—Lumen proximal end
3020—Lumen distal end
3030—Lumen interior cavity
3032—Open distal end
3034—Closed distal end
3040—Braid
3060—Elastomeric strip
3070—Hydrophobic
3080—Flat lumen
3100—Sampling Hub Lumen Distal Valve
3110—Nitinol clip—horizontal and vertical
3112—Vertical nitinol clip
3116—Horizontal nitinol clip
3118—Horizontal nitinol clip arm
3120—Duckbill
3122—Valve Slit
3130—Dome
3140—duckbill/donut/septum
3142—Duckbill
3144—Donut
3146—Donut probe hole
3148—Distal septum
3152—Proximal septum
3160—Expandable tip
3162—Cap
3164—Spring
3170—Side flap
3172—Single flap
3172—Double flap
4000—Exterior environment barrier A general description of the hub technology enabled herein includes a sampling hub for directing a medical device towards a target area, the hub with:
 a) a hub body having at least a front end, a rear end, a top, and a bottom configured to be facing downwards in respect to the target area;
 b) a lumen passing between openings at the front end or bottom and the rear end, the lumen allowing for passage of an elongate element through the entire lumen;
 c) the rear of the hub body configured to allow the elongate body to enter the lumen, and the hub body at the front end or bottom of the hub body configured to allow the elongate element to exit the lumen
 d) the lumen enables guidance of the elongate element towards the target area.

The distal end of the lumen may extend out of the hub, penetrate the patient's skin, and reside within or adjacent to the target area. The distal end of the lumen may have a valve or series of valves configured to prevent any material from the external environment to enter the lumen. The lumen may collapse to a closed position when the elongate element is not in the lumen, and thus prevents any material from the external environment to enter the distal end of the lumen. The lumen may be internally coated with a hydrophobic or hydrophilic material to prevent any material from the external environment from entering the distal end of the lumen. The distal valve(s) may be mechanically opened by the presence of the elongate element and returned to the closed position either by the removal of the elongate element or by an elastic memory of the valve.

The rear of the sampling hub may contain a barrier between the external environment and the sampling hub lumen. The barrier between the external environment and the sampling hub may contain a force-openable construction where the elongate element can pass through. By the term "force-openable construction" is meant a barrier having a closed (protective) and open position. To change from the closed position to the open position (where the sampler is exposed for use), a force must be applied to the barrier. The force may be applied from within the sampling hub lumen or from outside of the sampling hub lumen. If the barrier is a two-hinge, three-hinge or four-hinge closure, a force, such as that created by pushing the sampler forward, or pushing a parallel, internal post, a push-wire or the like forward against an inside surface of the hinge. Similarly, for an external force, a pull-wire may pass along the outside of the sampling hub lumen, along a surface parallel to the lumen, and extending to a tip where the distal ends of the hinged barrier meet. By pulling on the pull-wire, force is transmitted that will lift the hinges.

The hub may contain wings to provide stability to the hub when on the contact surface. The area surrounding the opening of the lumen at the rear end of the hub may be configured, structured, designed or shaped to receive a support for the elongate element, the support for the elongate element having a diameter larger than a diameter of the elongate element. The hub may be in two parts. The lumen may be contained within a the smaller part of the hub and the smaller part fits and then locks into a larger part of the hub to hold the smaller part of the hub in place. The internal lumen may have an angle shift to allow the lumen to exit the front or bottom of the hub at an angle more parallel to the surface of the target area than the angle where the elongate element was introduced into the internal lumen. The bottom surface may have an adhesive material to adhere the hub to the surface of the patient. The front end of the hub may have a viewing area through which a front end of the elongate element and/or the distal portion of the lumen may be seen.

The hub may have a rear end of a flat surface and the area surrounding the opening of the lumen is a geometric recess in the flat surface.

A method for collecting a sample from a target area according to the present technology may include steps of positioning a front end of a hub sampling device inside of or adjacent to the target area, the hub sampling device comprising:
  a) a hub body having at least a front end, a rear end, a top, and a bottom configured to be facing downwards in respect to the target area;
  b) a lumen passing between openings at the front end or bottom and the rear end, the lumen allowing for passage of an elongate element through the entire lumen;
  c) the rear of the hub body configured to allow the elongate body to enter the lumen, and the hub body at the front end or bottom of the hub body configured to allow the elongate element to exit the lumen
  d) the lumen enables guidance of the elongate element towards the target area.

The area surrounding the opening of the lumen at the rear end may be configured to receive a support for the elongate element, the support for the elongate element having a diameter larger than a diameter of the elongate element; the elongate element comprising a sampling tool; and the method further including passing the elongate element through the lumen and into the target area.

The method may have the elongate element as a collection element and the target area could In element of the elongate body enters the live patient through the sampling hub at the target area and a forward tip of the elongate body extends into the live patient. The method may use the front end of the hub with a viewing area through which the point where the lumen or elongate element penetrates the patient's skin may be seen while the hub is in place and during operation of the sampling method. The elongate element may be carried by a sheath slideable over the elongate element, the sheath is nestled within the hub, with the elongate element extended into the lumen, and the sheath is stabilized within the area surrounding the opening of the lumen at the rear end configured to receive a support for the elongate element. Nestling of the sheath within the hub causes the elongate element to slide within the sheath and extend forward out of the sheath. The distal end of the hub lumen may contain a valve or series of valves to prevent material from entering the lumen and the elongate element opens the valve to access the target area and the valve closes when the elongate element is withdrawn.

FIG. 1 describes an embodiment of the device. An aspect of an embodiment of the present invention is a sampling hub with an in-dwelling lumen 3000 secured in a plastic catheter hub 2200. The external hub 2200 also includes a sealed insertion port 2400 to prevent bacterial contamination of the in-dwelling catheter lumen 3000. A second component of an embodiment is a delivery catheter which fits through the sealed insertion port 2400 and slides within the larger hollow in-dwelling lumen 3000 during operation. The hollow lumen of this delivery catheter 1000 houses a sampling cannula 1500 which holds the blood to be sampled. In certain embodiments, the sampling stick is secured to a modular sampling component 1200 that can draw blood for a variety of applications and using a variety of mechanisms. In other certain embodiments, the sampling stick can act as a probe to prevent backflow of blood into the catheter lumen 3000 in between sampling periods.

Figure 2:
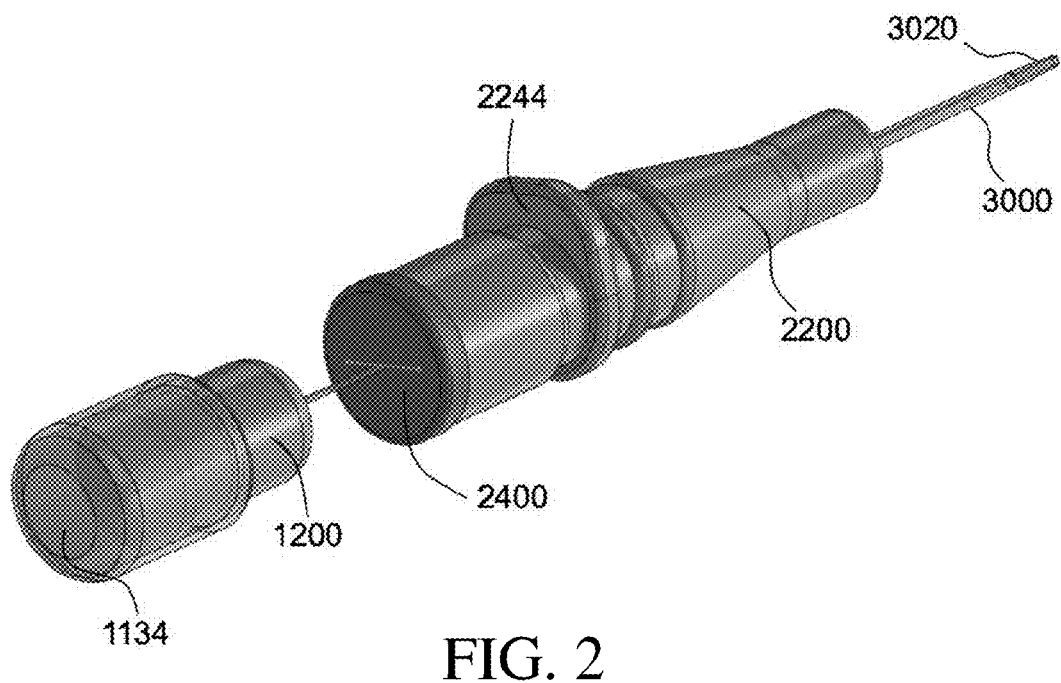
FIG. 2 shows a perspective view of the complete device according to a representative embodiment.
Figure 3:
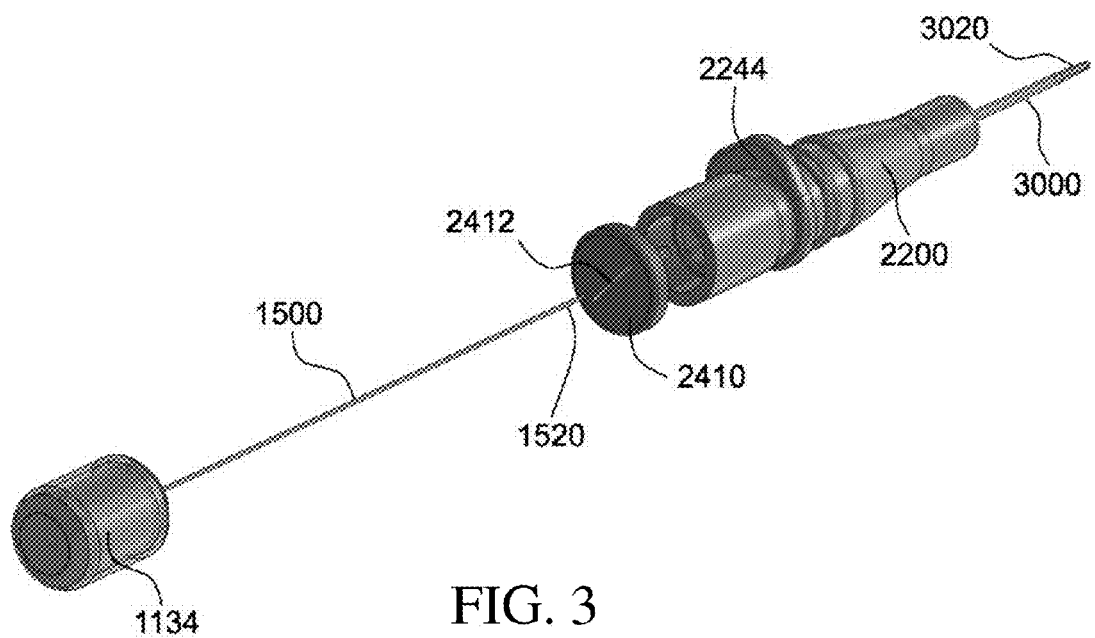
FIG. 3 shows a perspective view of the device components deconstructed according to a representative embodiment.
Figure 4:
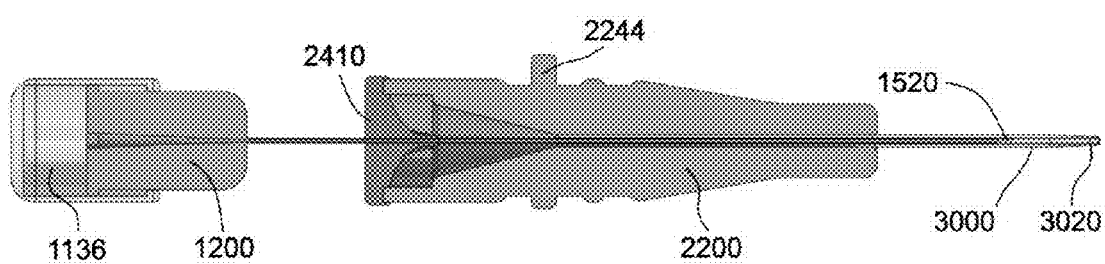
FIG. 4 shows a cross sectional view of the in-dwelling catheter assembly according to a representative embodiment.

An embodiment of the assembly of the present invention is illustrated in FIG. 2, a perspective view of the complete device and FIG. 3, an exploded perspective view of the device. The catheter has a hollow in-dwelling lumen 3000, which resides inside the patient's vein for the duration of the sampling period. The catheter is assembled with the plastic hub 2200, which holds the in-dwelling lumen 3000 in place and provides a stabilization point for the nurse using the ridged finger grip 2244. A sealed insertion port 2400 is assembled to the proximal edge of the plastic catheter hub 2200, and minimizes bacterial contamination of the catheter lumen 3000. The sampling cannula 1500, another hollow tube, is inserted through the sealed insertion port 2400 and through the lumen 3000 to sample blood from the distal end. The sampling cannula 1500 is combined with a modular sampling device 1200 which can draw up and store blood through the sampling cannula to be used for a variety of blood analyte tests. FIG. 4 shows a cross-section of the embodiment described in FIG. 3. In this figure the distal tip of the sampling cannula 1520 is partially inserted in the lumen of the sampling hub 3000.

Figure 5A:
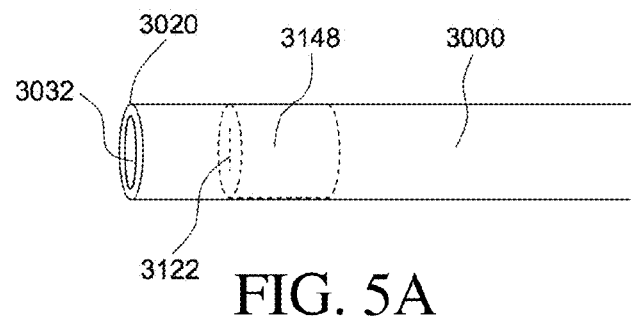
FIG. 5A shows a side view of the distal valve of the sampling hub lumen as a split septum according to a representative embodiment.
Figure 5B:
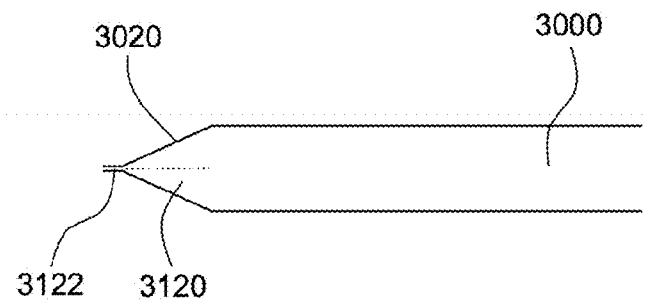
FIG. 5B shows a side view of the distal valve of the sampling hub lumen as a duckbill valve according to a representative embodiment.
Figure 5C:
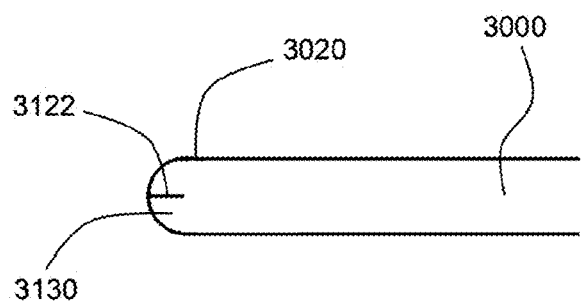
FIG. 5C shows a side view of the distal valve of the sampling hub lumen as a dome biscupid valve according to a representative embodiment.
Figure 5D:
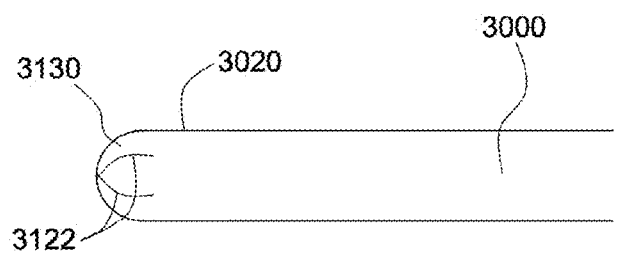
FIG. 5D shows a side view of the distal valve of the sampling hub lumen as a dome tricuspid valve according to a representative embodiment.
Figure 5E:
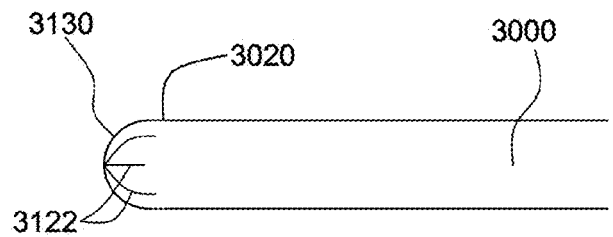
FIG. 5E shows a side view of the distal valve of the sampling hub lumen as a dome quadricuspid valve according to a representative embodiment.
Figure 5F:
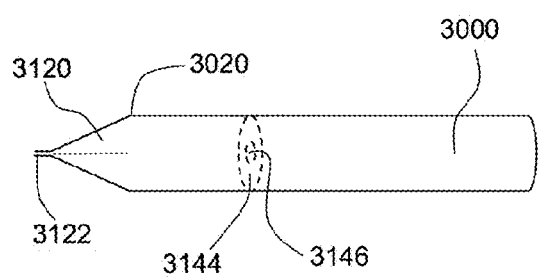
FIG. 5F shows a side view of the distal valve of the sampling hub lumen as a duckbill-donut combination valve according to a representative embodiment.
Figure 5G:
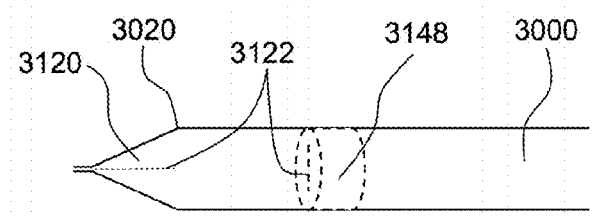
FIG. 5G shows a side view of the distal valve of the sampling hub lumen as a duckbill-split septum combination valve according to a representative embodiment.
Figure 5H:
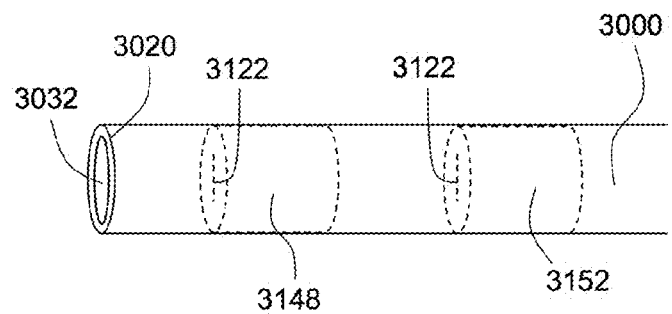
FIG. 5H shows a side view of the distal valve of the sampling hub lumen as a double split-septum combination valve according to a representative embodiment.
Figure 5I:
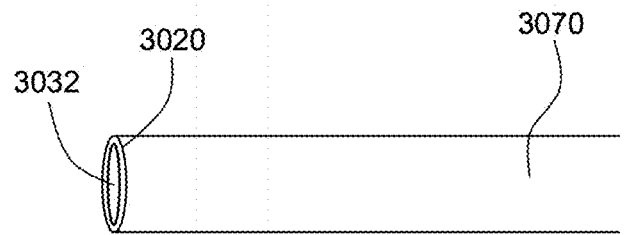
FIG. 5I shows a side view of the distal tip of the sampling hub lumen as a hydrophobic coated lumen according to a representative embodiment.
Figure 5J:
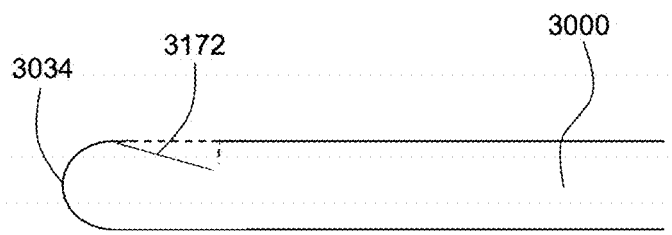
FIG. 5J shows a side view of the distal valve of the sampling hub lumen as a single side valve according to a representative embodiment.
Figure 5K:
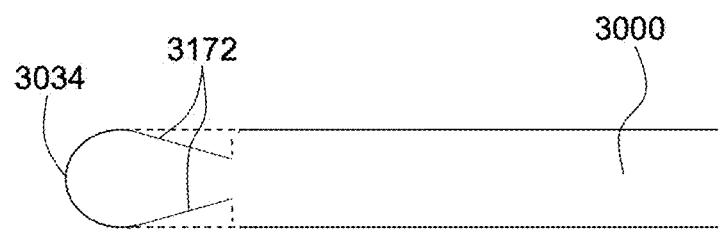
FIG. 5K shows a side view of the distal valve of the sampling hub lumen as a double side valve according to a representative embodiment.
Figure 5L:
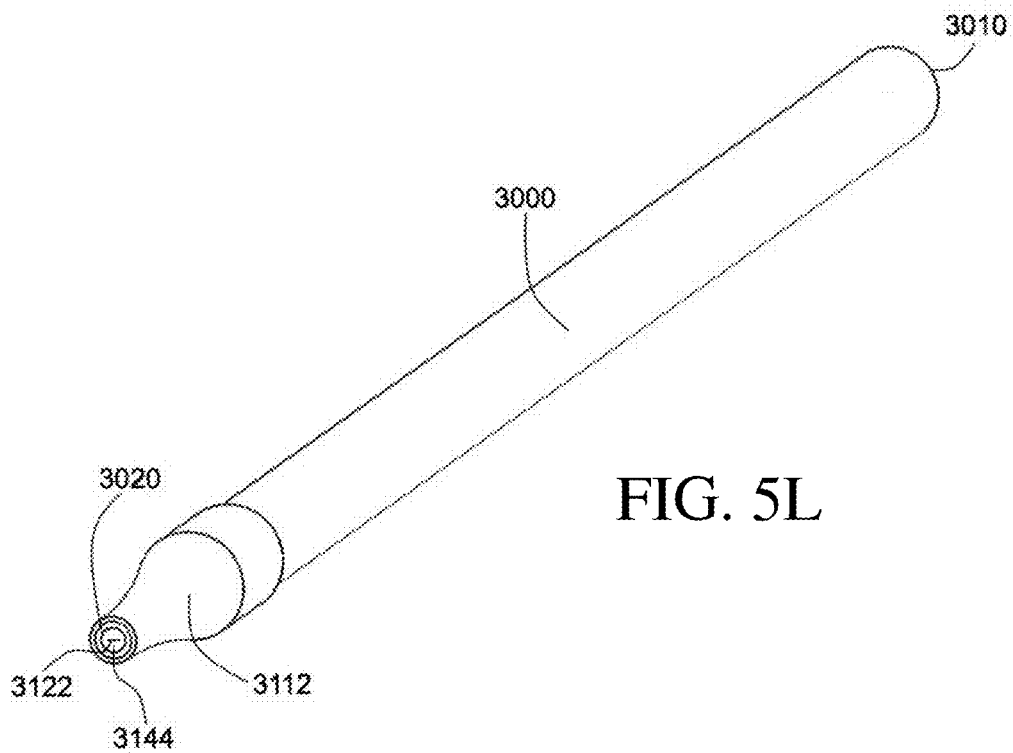
FIG. 5L shows a perspective view of the distal valve of the sampling hub lumen as a vertical clip valve according to a representative embodiment.
Figure 5M:
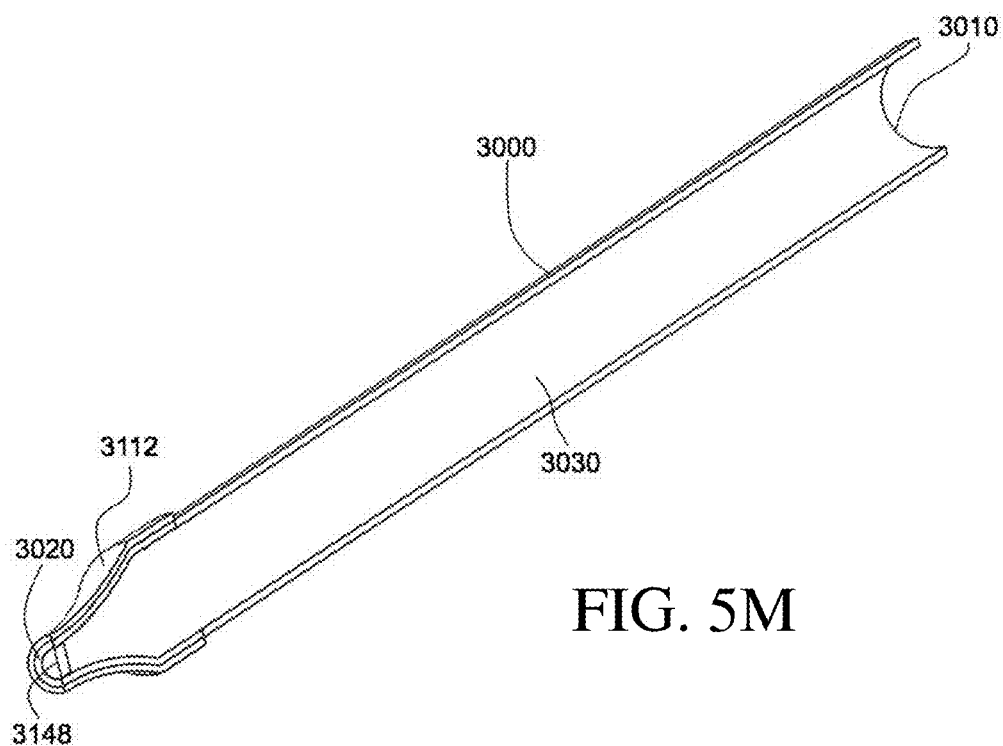
FIG. 5M shows a cross section view of the distal valve of the sampling hub lumen as a vertical clip valve according to a representative embodiment.
Figure 5N:
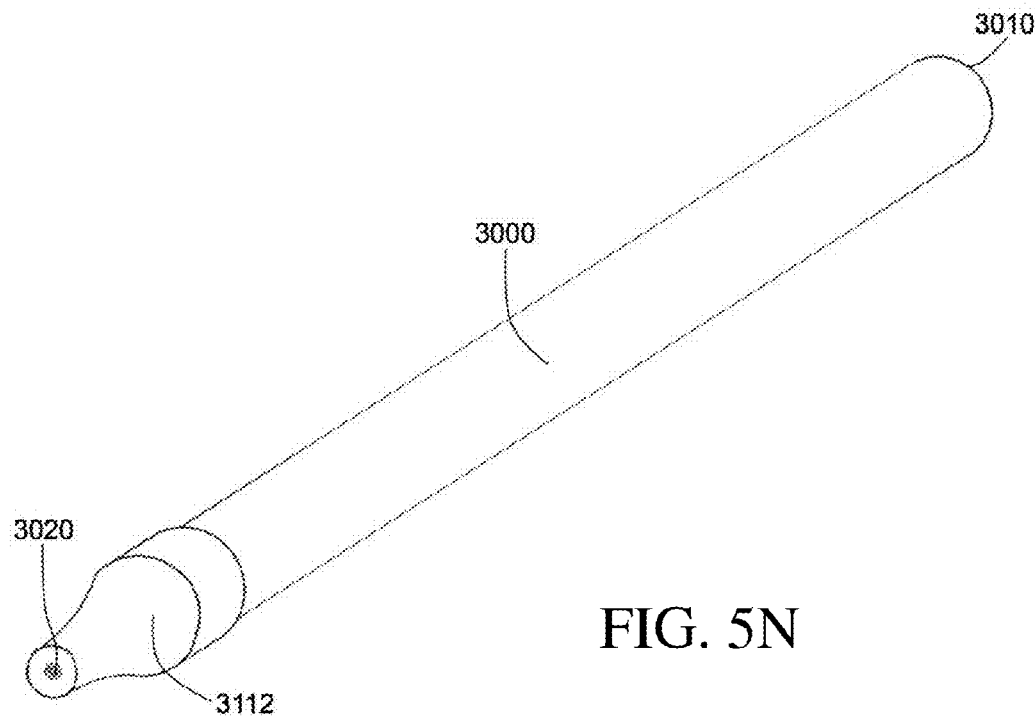
FIG. 5N shows a perspective view of the distal valve of the sampling hub lumen as a vertical clip closed off valve according to a representative embodiment.
Figure 5O:
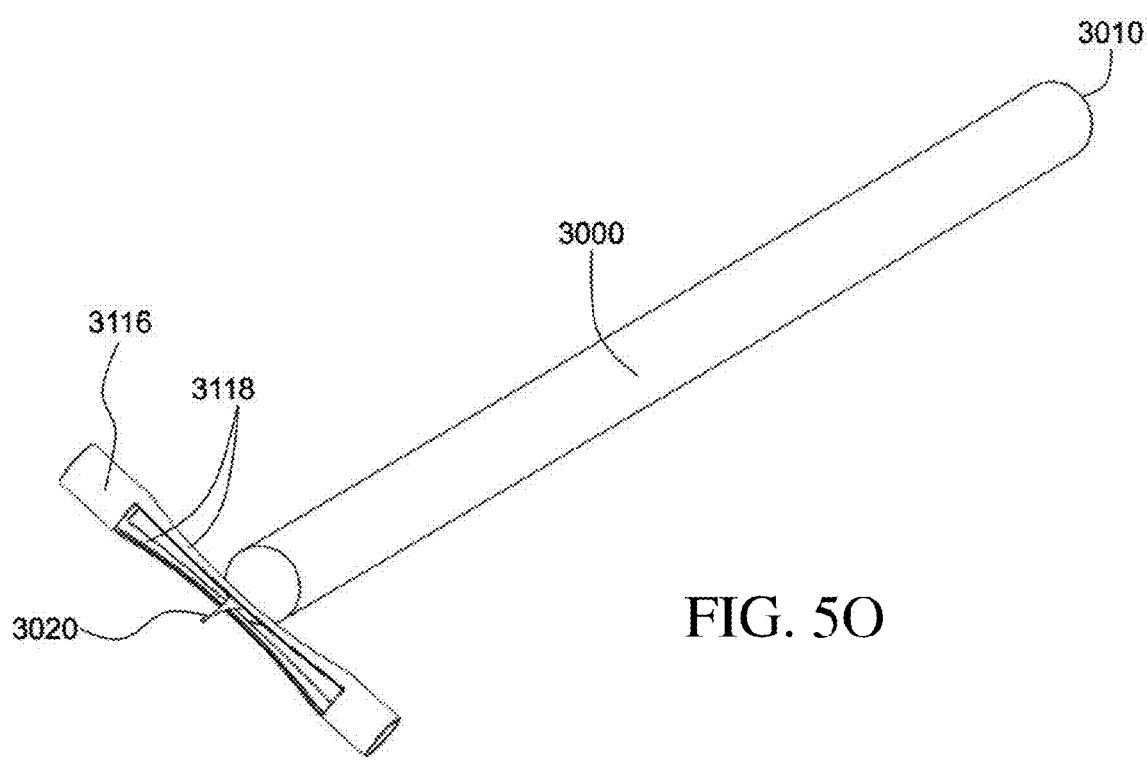
FIG. 5O shows a perspective view of the distal valve of the sampling hub lumen as a horizontal clip valve according to a representative embodiment.
Figure 5P:
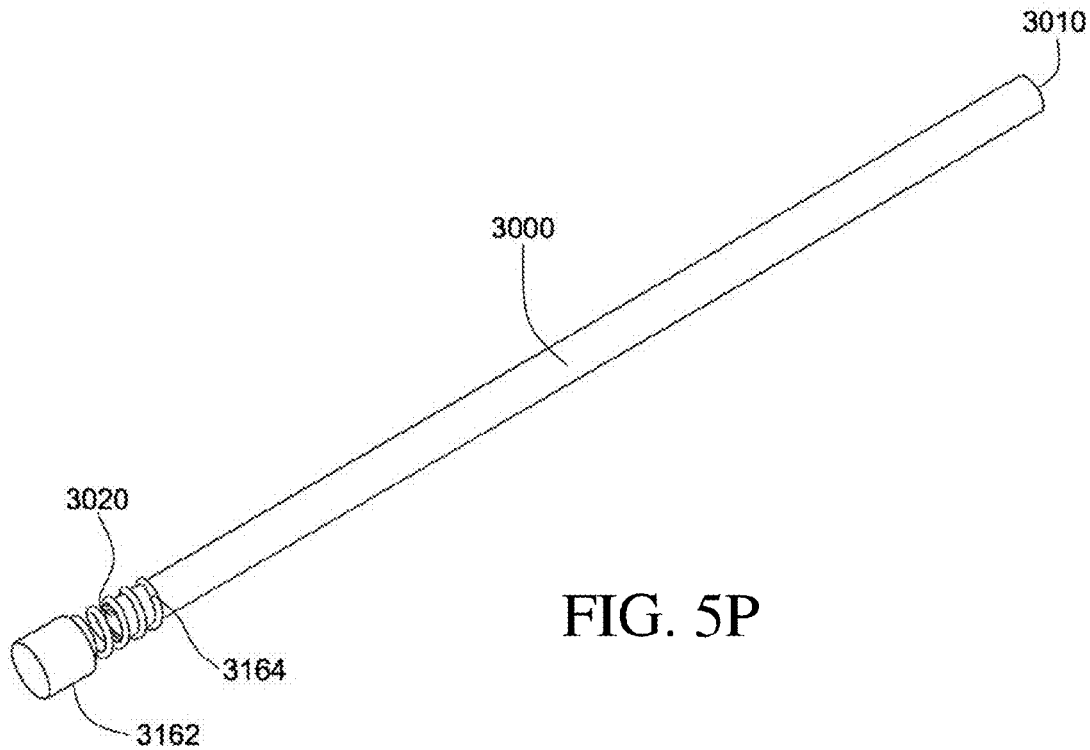
FIG. 5P shows a perspective view of the distal valve of the sampling hub lumen as an expanded spring cap valve according to a representative embodiment.
Figure 5Q:
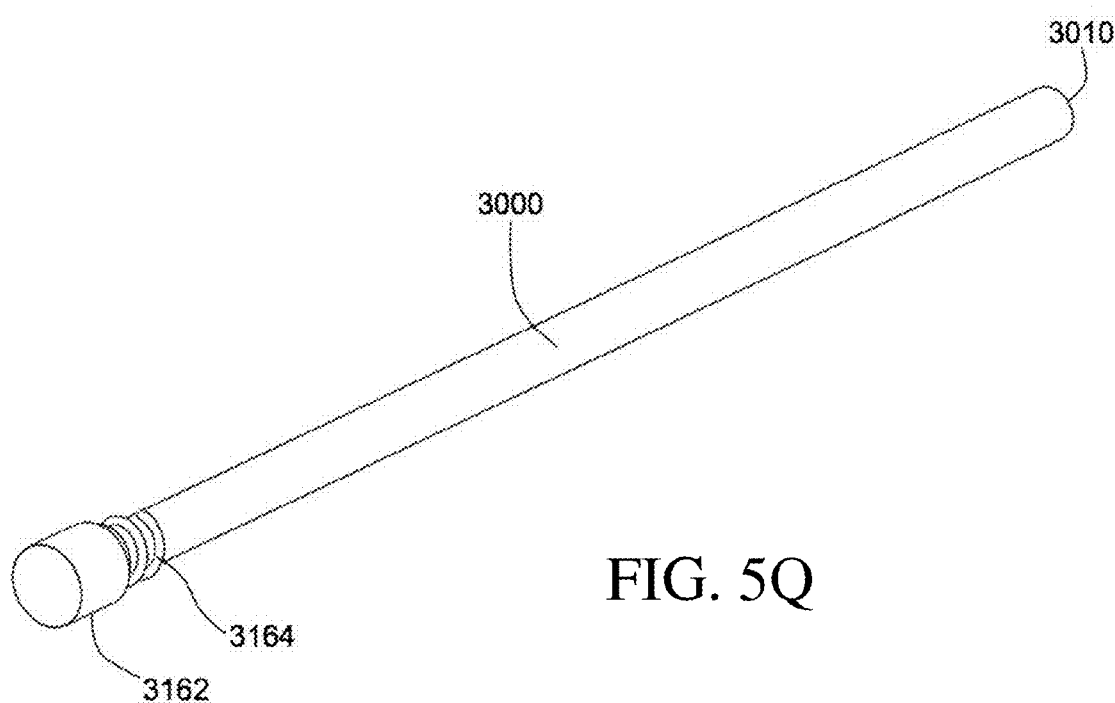
FIG. 5Q shows the distal valve of the sampling hub lumen as a compressed spring cap valve according to a representative embodiment.

The distal valve 3100 on the inner lumen 3000 of the sampling hub 2200 has many possible embodiments. FIG. 5A details an open lumen 3032 housing a split septum 3148 with a slit 3122 on the distal end 3020 of the lumen. FIG. 5B shows a duckbill valve 3120. FIG. 5C-5E show possible embodiments of a dome valve 3120. FIG. 5F houses an additional donut valve 3144 with an opening 3146 that expands around the sampling cannula 1500 as it is inserted. FIG. 5G introduces a series of valves and has a duckbill valve 3120 at the distal end of the lumen 3020 and a split septum 3148 which is proximal to the duckbill valve 3120. FIG. 5H shows a second proximal split septum 3152. FIG. 5I shows a hydrophobic coating 3070 on the lumen to act as a flow control valve. FIG. 5J-5K have a closed lumen tip 3034 and side valve(s) 3172 that opens to allow liquid to flow into the lumen 3000. FIG. 5L-5N show different embodiments of using a nitinol clip 3112 in the longitudinal direction to seal the distal end of the lumen 3020. FIG. 5O shows an alternative use of a horizontal nitinol clip 3116 having arms 3118 which hold the distal end of the lumen 3020 closed. FIG. 5P-5Q shows a spring 3164 and a cap 3162 which can be pushed open by the sampling cannula 1500.

Figure 6A:
FIG. 6A shows a side view of the distal tip of the sampling cannula with smooth through holes according to a representative embodiment.
Figure 6B:
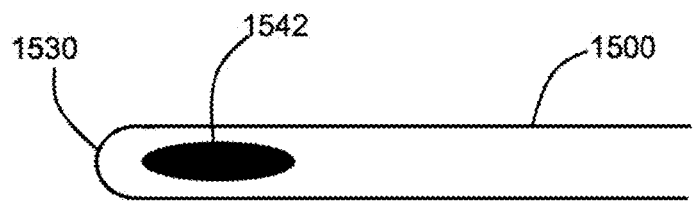
FIG. 6B shows a side view of the distal tip of the sampling cannula with a smooth side hole according to a representative embodiment.
Figure 6C:
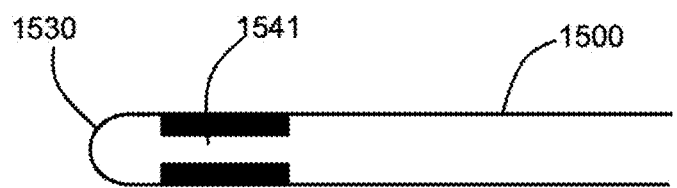
FIG. 6C shows a side view of the distal tip of the sampling cannula with rectangular through holes according to a representative embodiment.
Figure 6D:
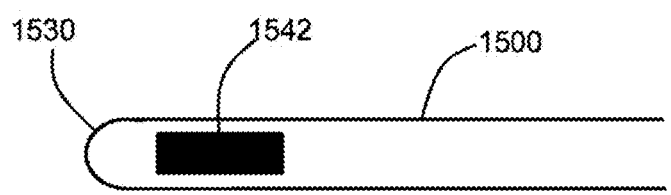
FIG. 6D shows a side view of the distal tip of the sampling cannula with a rectangular side hole according to a representative embodiment.
Figure 6E:
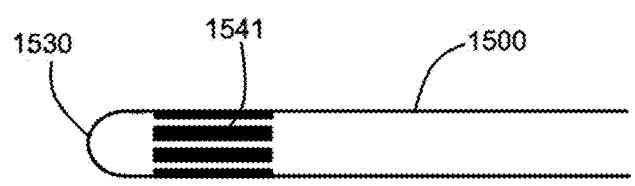
FIG. 6E shows a side view of the distal tip of the sampling cannula with vertical slit holes according to a representative embodiment.
Figure 6F:
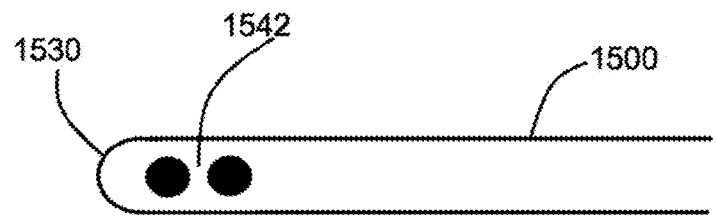
FIG. 6F shows a side view of the distal tip of the sampling cannula with circular holes according to a representative embodiment.
Figure 6G:
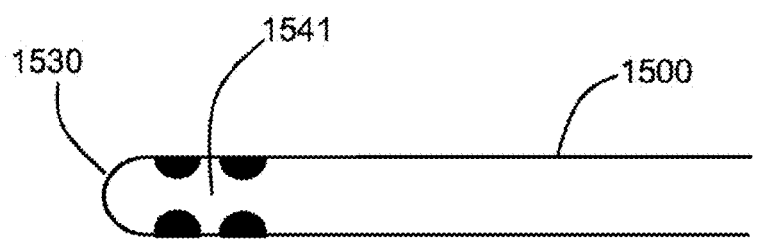
FIG. 6G shows a side view of the distal tip of the sampling cannula with circular through holes according to a representative embodiment.
Figure 6H:
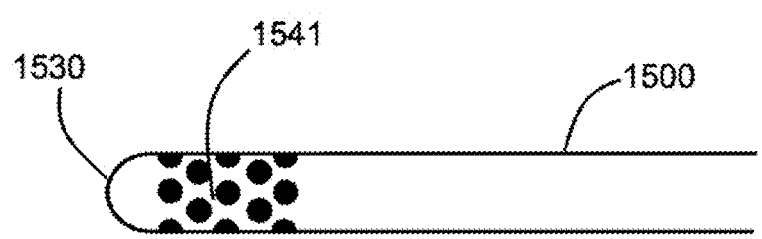
FIG. 6H shows a side view of the distal tip of the sampling cannula with micro holes according to a representative embodiment.
Figure 6I:
FIG. 6I shows a side view of the distal tip of the sampling cannula with smooth through holes and tip hole according to a representative embodiment.
Figure 6J:
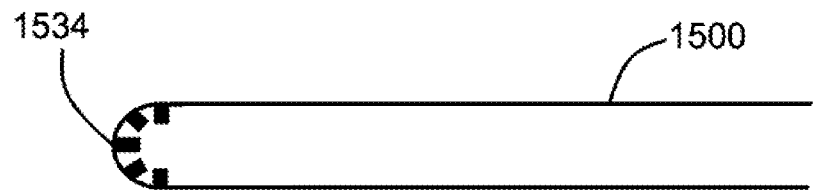
FIG. 6J shows a side view of the distal tip of the sampling cannula with multiple tip holes according to a representative embodiment.
Figure 6K:
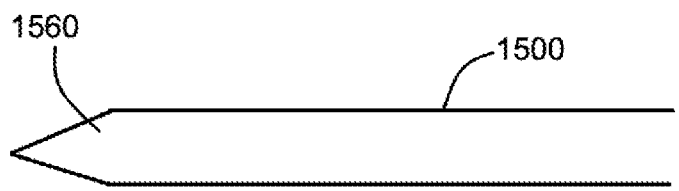
FIG. 6K shows a side view of the distal tip of the sampling cannula with a needle tip according to a representative embodiment.
Figure 6L:
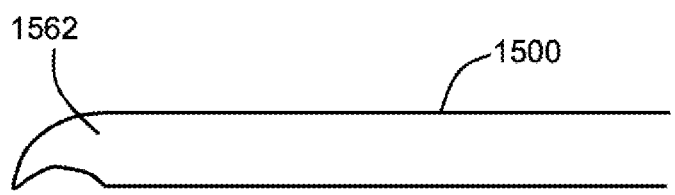
FIG. 6L shows a side view of the distal tip of the sampling cannula with a non-coring needle tip according to a representative embodiment.
Figure 6M:
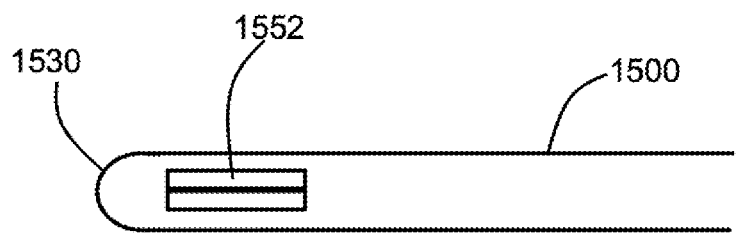
FIG. 6M shows a side view of the distal tip of the sampling cannula with inward folding valve according to a representative embodiment.
Figure 6N:
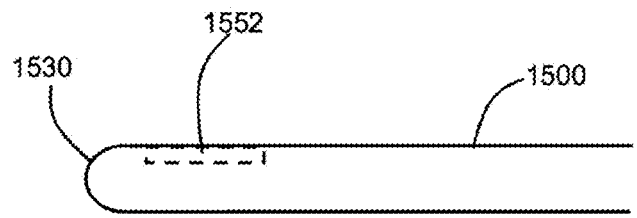
FIG. 6N shows a side view of the distal tip of the sampling cannula with the inward folding valve in position 1 according to a representative embodiment.
Figure 6O:
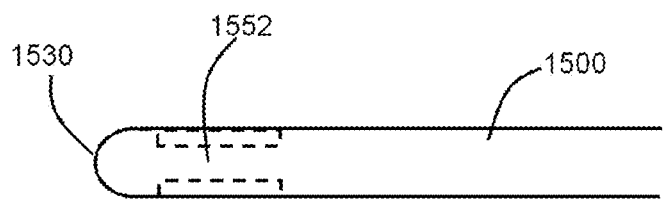
FIG. 6O shows a side view of the distal tip of the sampling cannula with side view of two inward folding valves in position 1 according to a representative embodiment.
Figure 6P:
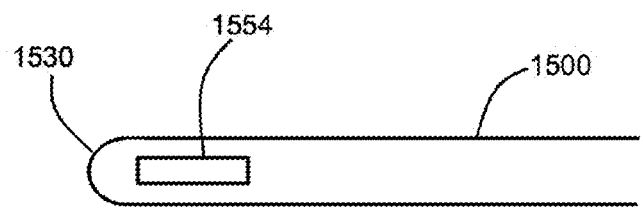
FIG. 6P shows a side view of the distal tip of the sampling cannula with proximal folding valve in position 1 according to a representative embodiment.
Figure 6Q:
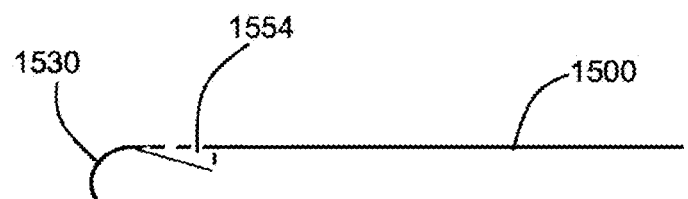
FIG. 6Q shows a side view of the distal tip of the sampling cannula with proximal folding valve in position 2 according to a representative embodiment.
Figure 6R:
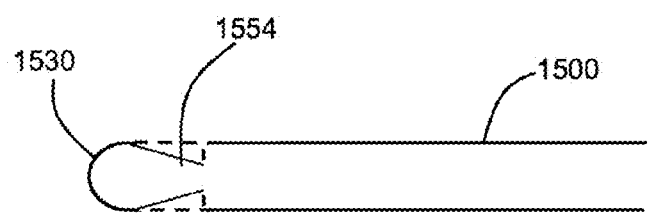
FIG. 6R shows a side view of the distal tip of the sampling cannula with two proximal folding valves in position 2 according to a representative embodiment.

Referring now to FIG. 6A-6R, which show various embodiments of the distal end of the sampling cannula 1520. FIG. 6A-6H are different embodiments of the sampling cannula 1500 with a rounded distal tip 1530. These embodiments have side through holes 1541 and holes that are only on one side 1542. FIG. 6I has an opening 1532 on the distal tip. FIG. 6J shows multiple openings 1534 on the distal tip. FIG. 6K has a sharp needle tip 1560 and FIG. 6L has a non-coring needle tip 1562. FIG. 6M-6R show two different types of valves. FIG. 6M-6O show an inward folding side valve 1552 that can be located on either one or both sides of the sampling cannula 1500. FIG. 6P-6R shows a side valve where the proximal end folds inward 1554.

Figure 7A:
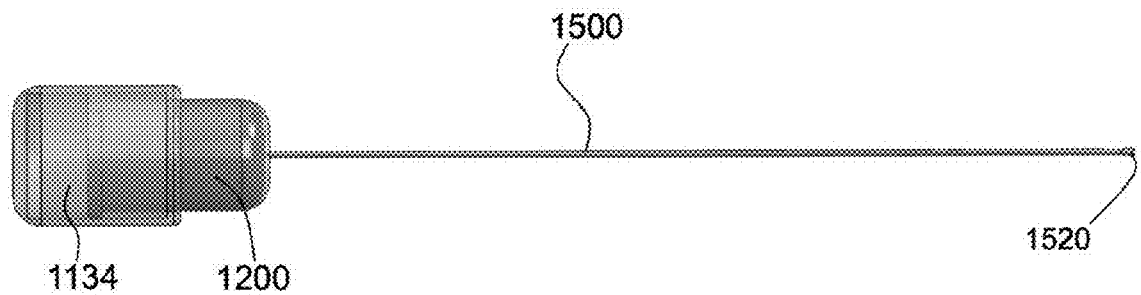
FIG. 7A shows side views of the sampling module for smaller volumes of blood collection according to representative embodiments.
Figure 7B:
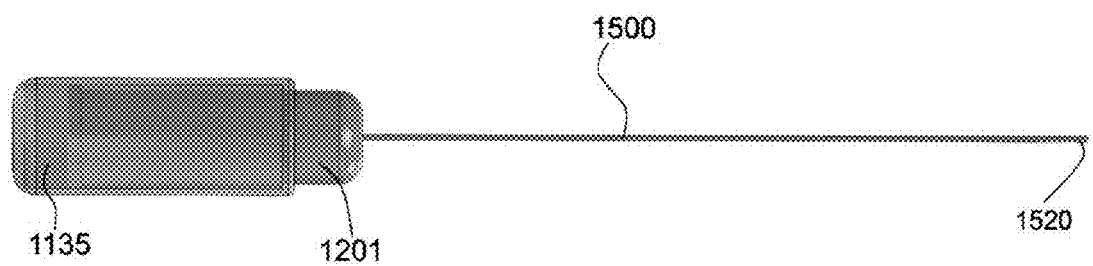
FIG. 7B shows side views of the sampling module for larger volumes of blood collection according to representative embodiments.
Figure 7C:
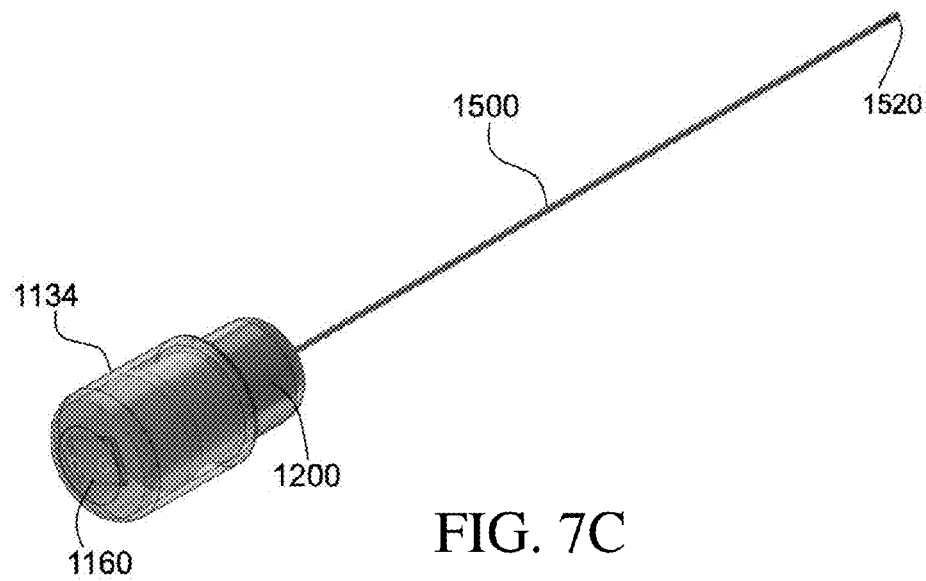
FIG. 7C shows a perspective view for a sampling module containing a built-in blood chemistry test according to a representative embodiment.

Referring now to FIGS. 7A-7C, three sampling modules (delivery catheters) 1000 embodiments are represented. FIG. 7A demonstrates the sampling cannula lumen and sampling cannula distal end 1520 are common for all three embodiments. The sampling module 1000 is the varying feature in each figure. The first embodiment: small sampling module is the smallest of the three embodiments and is composed of two components. The first embodiments: small sampling barrel 1134 fits over the first embodiments: small sampling plunger 1200 and creates a vacuum suction when pulled that draws blood into the sampling cannula lumen 1500. The second embodiment: large sampling module is the largest of the three embodiments and is composed of two components. The second embodiments: large sampling barrel 1135 fits over the second embodiments: large sampling plunger 1201 and creates a vacuum suction when pulled that draws blood into the sampling cannula lumen 1500. This larger size allows for greater volumes of blood to be collected for various testing purposes. The third embodiment: blood chemistry test sampling module 1160 contains a testing area on the proximal end of the third embodiment: blood chemistry test sampling barrel 1200 and is composed of two components. The third embodiments: blood chemistry test sampling barrel 1200 fits over the third embodiments: blood chemistry test sampling plunger 1134 and creates a vacuum suction when pulled that draws blood into the sampling cannula lumen 1500. The proximal testing unit is composed of a modular assay strip 1160 and a modular connection to assay reader 1160 which represent a connection port of the third embodiment: blood chemistry test sampling barrel to a chemistry test device.

Figure 8:
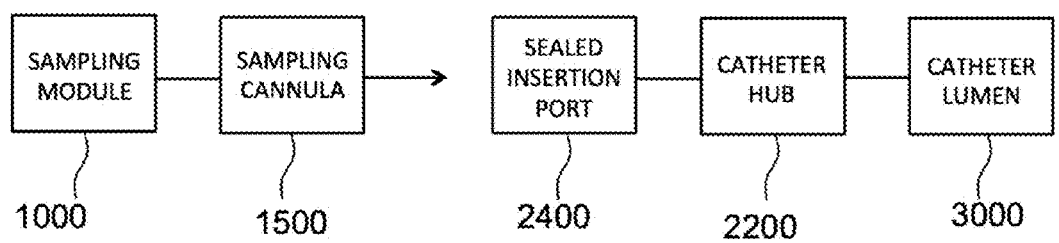
FIG. 8 shows a block diagram for the overall sampling method.

FIG. 8 represents a block diagram demonstrating the component's embodiments and their uses. The sampling cannula lumen 1500 is connected to the sampling module 1100. This combined overall component is used in conjunction with the sampling hub 2200 and its connected components. The sealed insertion port 2410 is joined to the proximal end of the sampling hub 2114. The lumen 3000 is located on the distal end of the sampling hub 2216 to create the overall sampling hub component of the device. Within the sampling cannula 1500, the sampling module 1000 is connected at its distal end to the sampling stick lumen 1520, which is inserted through the sealed insertion port 2400 and through the sampling hub 2200 until its distal end 1520 passes through the catheter lumen 3000 and the distal tip of the in-dwelling lumen 3020.

Figure 9A:
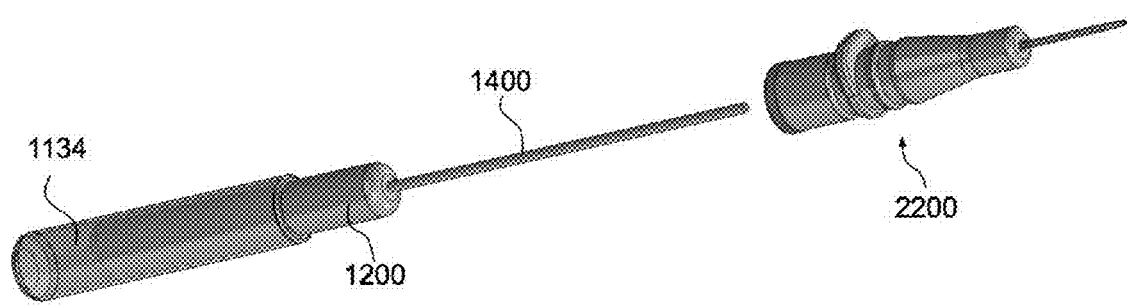
FIG. 9A shows a perspective view of a second alternative design to ease insertion of the sampling stick according to a representative embodiment.
Figure 9B:
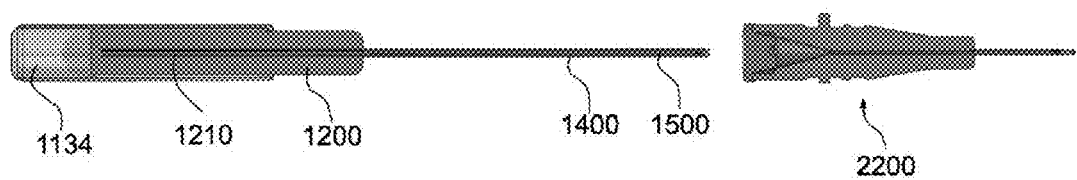
FIG. 9B shows another perspective view of a second alternative design to ease insertion of the sampling stick according to a representative embodiment.

Referring now to FIGS. 9A and 9B, a perspective view of a second alternative design to ease insertion of the sampling cannula, FIG. 9A is an alternative embodiment of the assembly of the sampling stick with cover. This embodiment incorporates a delivery catheter 1000 that covers the sampling cannula 1500 prior to insertion. The cross-sectional view in FIG. 9B shows the sampling module plunger for covered version 1200, which has a sampling stick cover storage area 1210. This provides an area for when the sampling stick sheath 1400 is forced backwards by the interior of the catheter hub 2200. The sampling cannula sheath 1400 will have enough resistance to continue to sheath the sampling cannula for covered version 1500 as the sampling stick sheath 1400 moves through the sealed insertion port 2400. The interior of the sampling hub 2200 will provide the necessary force to retract the sampling cannula sheath 1400 into the sampling cannula cover storage area 1210, exposing the tip of the sampling cannula 1500 and allowing movement through the in-dwelling lumen 3000. Upon removal of the sampling cannula 1500 from the sampling hub 2200, the resistance holding the sampling cannula sheath 1400 will diminish and return the sampling cannula sheath 1400 back to its covered position, protecting the sampling stick 1500.

Figure 10:
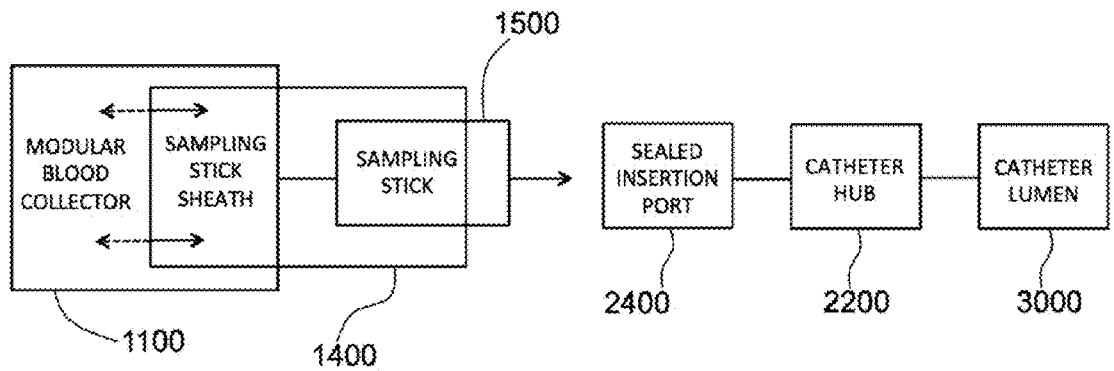
FIG. 10 shows a block diagram for a second alternative design.

Referring now to FIG. 10, a block diagram for the second alternative design, this representative embodiment incorporates a sealed sampling stick sheath 1400 that surrounds the sampling cannula 1500 to ease insertion through the sealed insertion port 2400. During the sampling procedure, both the sampling cannula 1500 and sampling cannula sheath 1400 are inserted through the sealed insertion port 2400 and into the sampling hub 2200. Upon further insertion, the sampling hub 2200 comes in contact with and unsheathes the sampling cannula cover 1400. Further, the sampling stick 1500 enters the sampling hub lumen 3000 without resistance from the sampling hub insertion port 2400. The connected modular blood collector 1100 applies force on the sampling cannula 1500 during this action. Upon full insertion of the sampling cannula 1500, the sampling cannula sheath 1400 is fully retracted into the modular blood collector 1100.

Figure 11A:
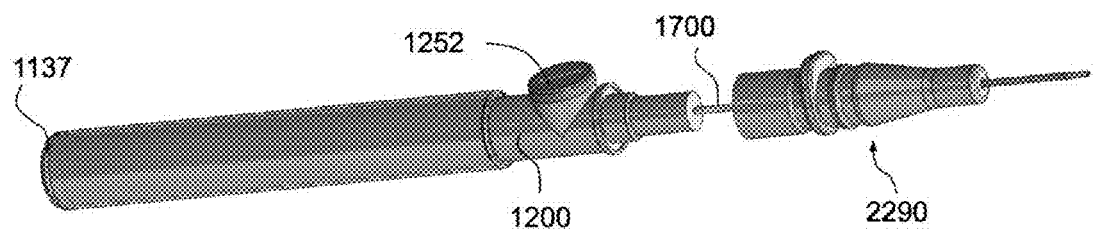
FIG. 11A shows a perspective view of a third alternative design of a blood sampling catheter according to a representative embodiment.
Figure 11B:
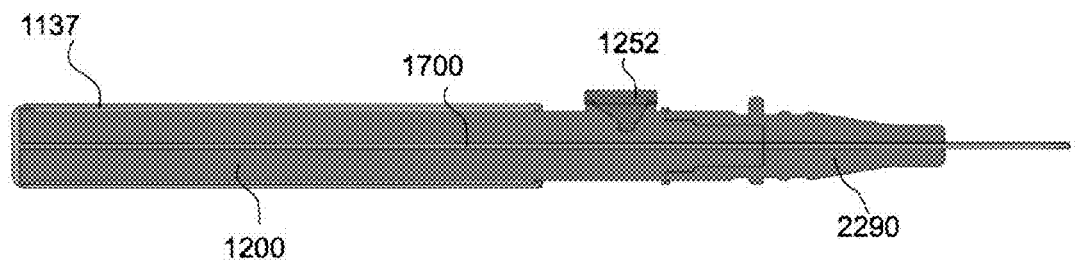
FIG. 11B shows another perspective view of a third alternative design of a blood sampling catheter according to a representative embodiment.

Referring now to FIGS. 11A and B, a perspective and cross-sectional view of a third alternative design of a blood sampling catheter, FIGS. 11A-B represent an alternative embodiment of the design that eliminates air inside a generic IV catheter 2290. The probe 1700 is a solid component that remains inserted through the center of the catheter 2290 at all times. Only when a sample is being drawn and the probe 1700 is deployed will the interior of the generic IV catheter 2290 become vacant. The distal end of the probe stick 1720 inserts into the generic IV catheter 2290 and provides support and a side sealed insertion port 1252 for sampling blood. The probe 1700 is connected to the base of the probe plunger 1137 so that when deployed, the probe 1700 will pull out of the generic IV catheter 2290 and leave a clear pathway through the in-dwelling catheter lumen 3000 and into the probe 1700 for sampling. The probe plunger 1137 is designed to pull the probe 1700 back just far enough to allow blood to reach the side access port 1252. Upon collection of blood, the probe plunger 1137 and probe 1700 will be repositioned inside the generic IV catheter 2290, removing any blood or debris from the interior cavities.

Figure 12:
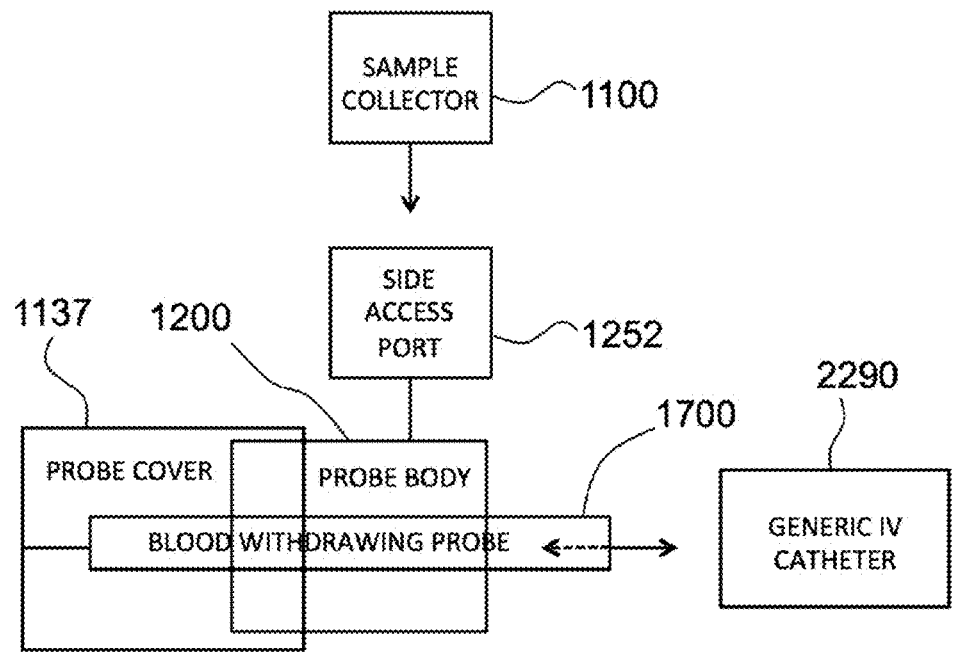
FIG. 12 shows a block diagram for a third alternative design.

Referring now to FIG. 12, block diagram for the third alternative design, this probe sampling system is installed into a generic IV catheter 2290 during the sampling period. When installing this probe sampling system, the probe body 1200 is inserted into and attached to the generic IV catheter 2290. When the probe sampling system is not being used to sample blood, the solid probe 1700 is fully inserted into the generic IV catheter 2290 and past its lumen tip. During sampling, the probe cover 1137 is deployed/pulled back, therefore pulling back the probe 1700 back through the lumen and body of the generic IV catheter 2290 and into the probe body 1200. During this action, negative pressure created by the solid probe 1700 draws blood from the vascular system through the generic IV catheter 2290 and into the probe body 1200. In order to withdraw blood from the system, a sample collector 1100 is inserted into a side access port 1252, which is connected to the internal lumen of the probe body 1200. Following withdrawal of blood from the probe body 1200 by the sampling collector 1100, the probe cover 1137 is returned to its undeployed forward position, thereby pushing the connected probe 1700 through the body and lumen of the generic IV catheter 2290. During this action, the solid probe 1700 expels all blood from the probe sampling system.

Figure 13A:
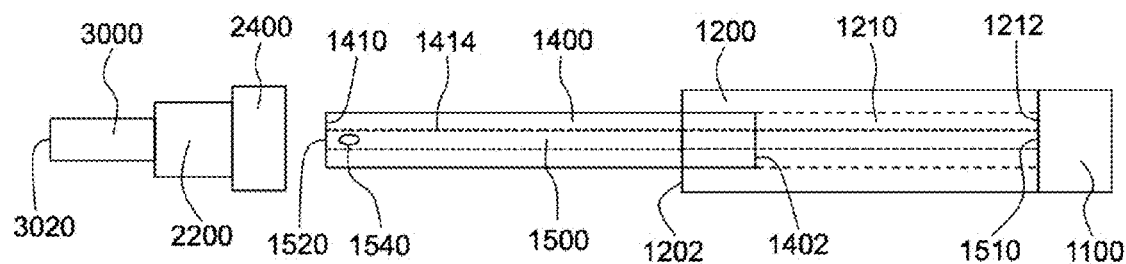
FIG. 13A shows the delivery catheter with sampling hub during operation in position 1.

FIG. 13A is a side view of a delivery catheter 1000 according to the present technology in a position (Position 1) outside of the sampling hub 2200 and adjacent to the sampling hub proximal valve 2400. The delivery catheter 1000 is comprised of a proximal part 1200 and a distal sheath 1400. The proximal part 1200 houses an inner chamber 1210 with a proximal end 1212 where the distal sheath 1400 can retract into. The distal sheath 1400 has both a distal 1410 and a proximal 1402 end. This distal sheath contains an internal chamber 1414 that a sampling cannula 1500 fits through. The sampling cannula 1500 has a lumen with a distal 1520 and a proximal 1510 end. The sampling cannula 1500 has a side hole(s) 1540 to allow fluid to access its lumen. The proximal end of the sampling cannula 1510 and delivery catheter 1212 connect to a collection mechanism 1100 where fluid can be stored. The sampling hub has a lumen 3000. The distal end of the lumen 3020 is also shown.

Figure 13B:
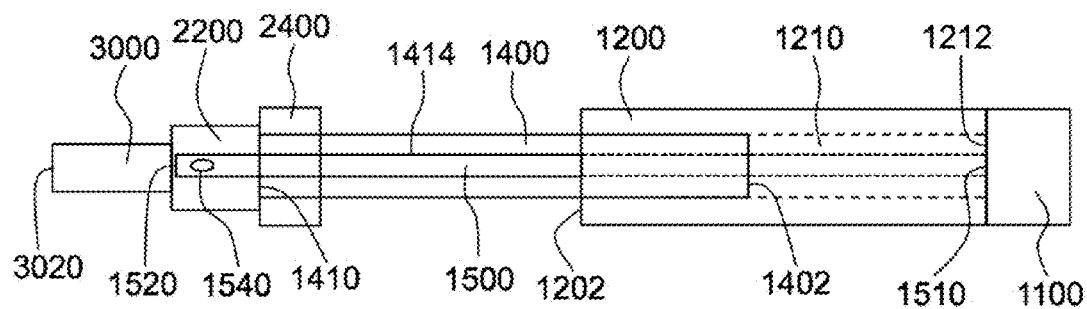
FIG. 13B shows the delivery catheter with sampling hub during operation in position 2.

FIG. 13B is a side view of a delivery catheter 1000 according to the present technology in a position (Position 2) half way inserted into the sampling hub 2200. This figure is a general outline of the sampling hub 2200 with the deliver catheter 1000 halfway inserted. The distal sheath of the delivery catheter 1400 is penetrating the sampling hub proximal port 2400. When the distal sheath 1400 penetrates the catheter proximal valve 2400 it begins to retract into the proximal part chamber 1210. The sampling cannula 1500 continues forward into the sampling hub body 2200 and lumen 3000.

Figure 13C:
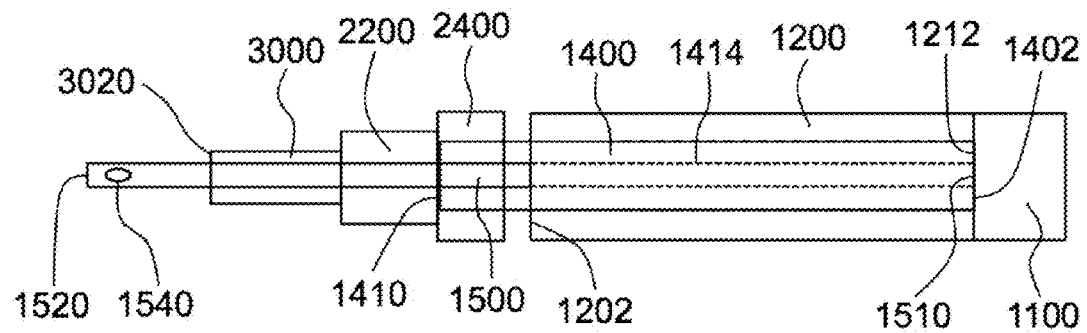
FIG. 13C shows the delivery catheter with sampling hub during operation in position 3.

FIG. 13C is a side view of the delivery catheter 1000 according to the present technology in a position (Position 3) wherein the distal sheath of the delivery catheter 1400 penetrates the catheter proximal port 2400 and the cannula 1500 is entirely through the sampling hub lumen 3000. This figure is a general outline of the sampling hub 2200 with the delivery catheter 1000 and the sampling cannula 1500 fully inserted.

Figure 14A:
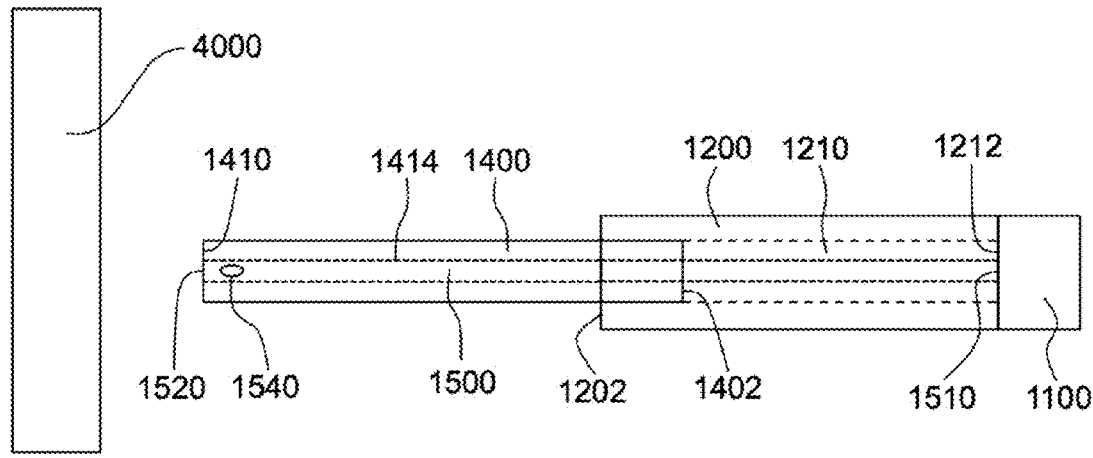
FIG. 14A shows the delivery catheter entering an environment through a barrier during operation in position 1.

FIG. 14A is general figure showing the delivery catheter 1000 with an environmental barrier 4000 in position 1.

Figure 14B:
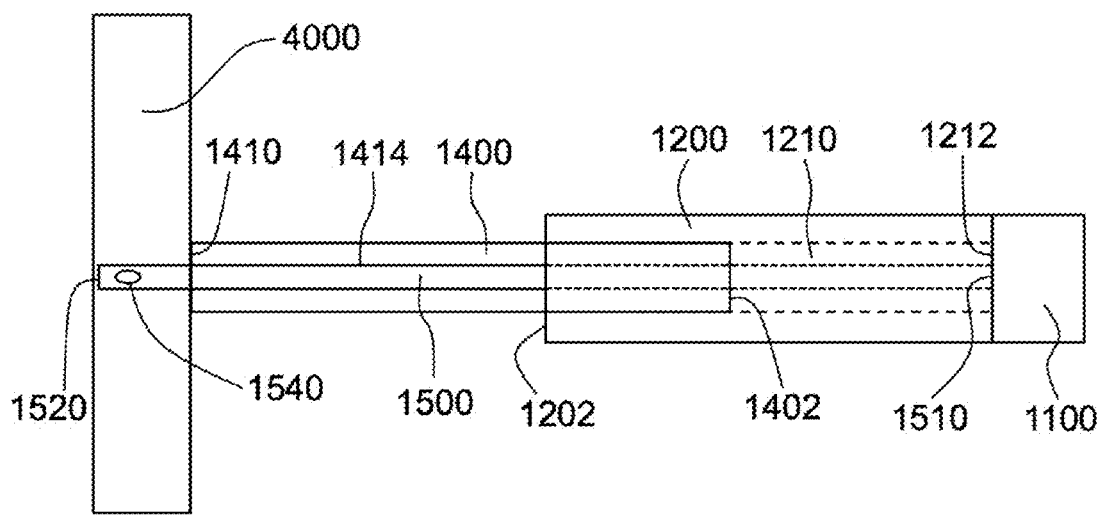
FIG. 14B shows the delivery catheter entering an environment through a barrier during operation in position 2.

FIG. 14B is general figure showing delivery catheter 1000 with an environmental barrier 4000 in position 2.

Figure 14C:
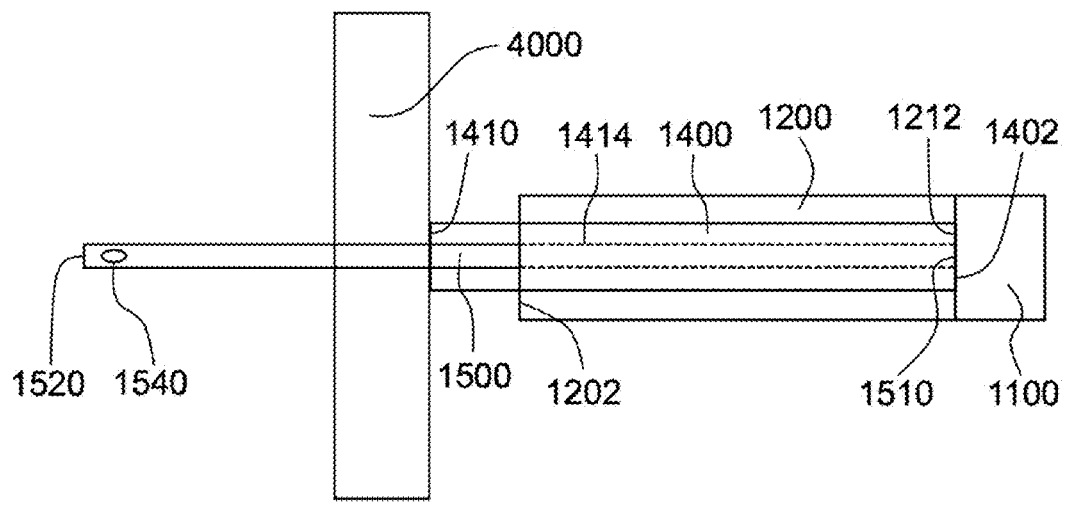
FIG. 14C shows the delivery catheter entering an environment through a barrier during operation in position 3.

FIG. 14C is general figure showing delivery catheter 1000 with an environmental barrier 4000 in position 3.

Figure 15A:
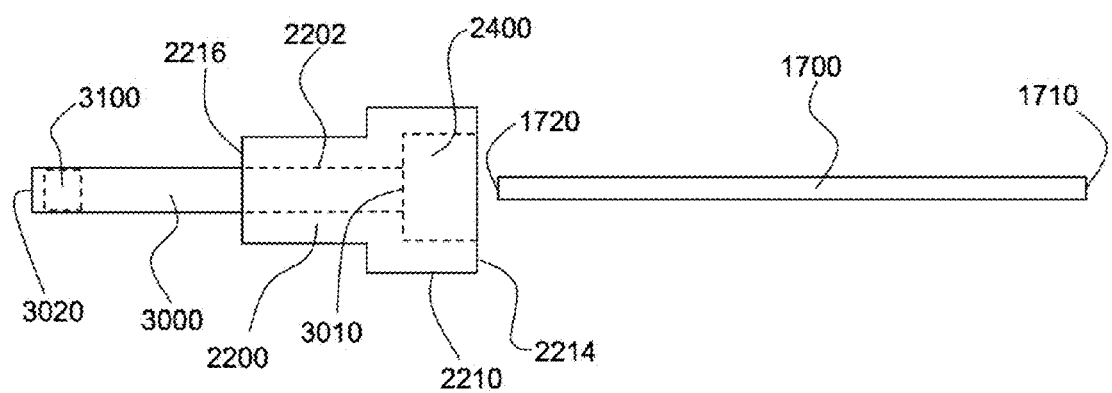
FIG. 15A shows a metal probe going through sampling hub during operation during operation in position 1.

FIG. 15A is general figure showing sampling hub 2200 with a distal valve 3100 and probe 1700 in position 1. The probe has both a distal end 1720 and proximal 1710 end. This figure also shows the distal end 2216 and proximal 2214 ends of the sampling hub 2200 and the distal end 3020 and proximal 3010 end of the sampling hub lumen 3000.

Figure 15B:
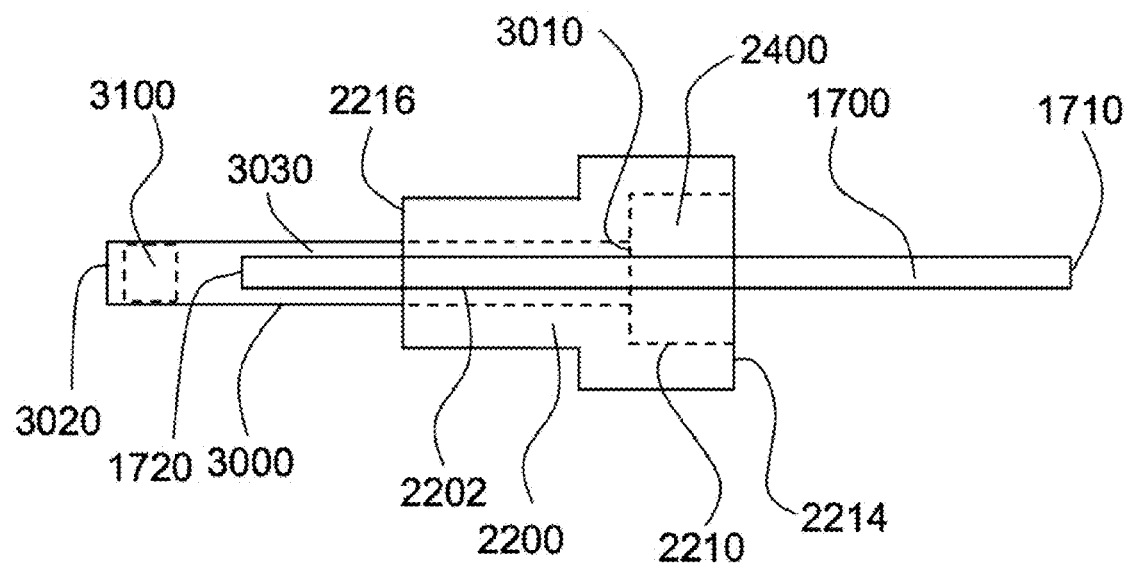
FIG. 15B shows a metal probe going through sampling hub during operation during operation in position 2.

FIG. 15B is general figure showing sampling hub 2200 with a distal valve 3100 and probe 1700 in position 2.

Figure 15C:
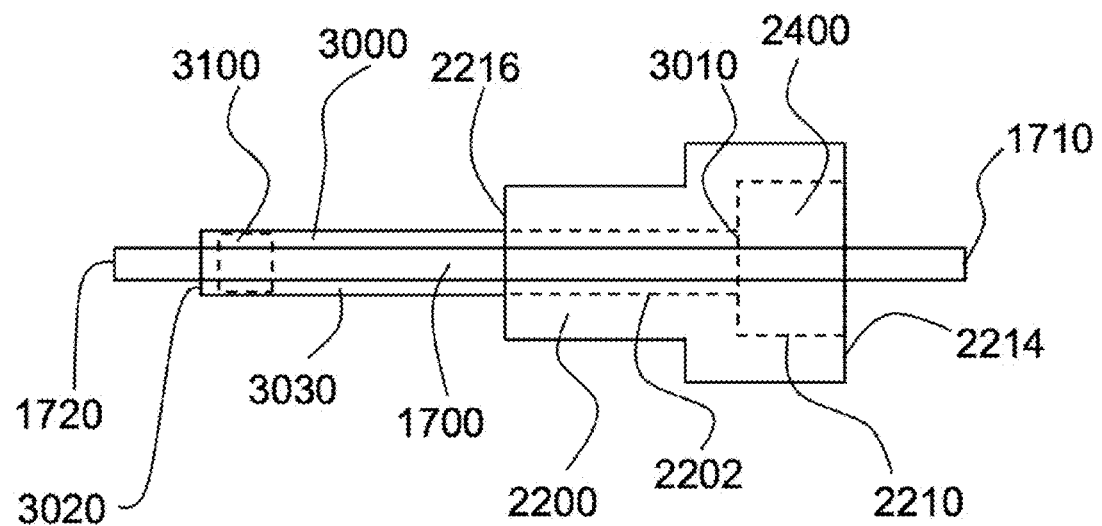
FIG. 15C shows a metal probe going through sampling hub during operation during operation in position 3.

FIG. 15C is general figure showing sampling hub 2200 with a distal valve 3100 and probe 1700 in position 3 with the distal end of the probe 1720 past the distal valve 3100 and the distal end of the sampling hub lumen 3020.

Figure 16A:
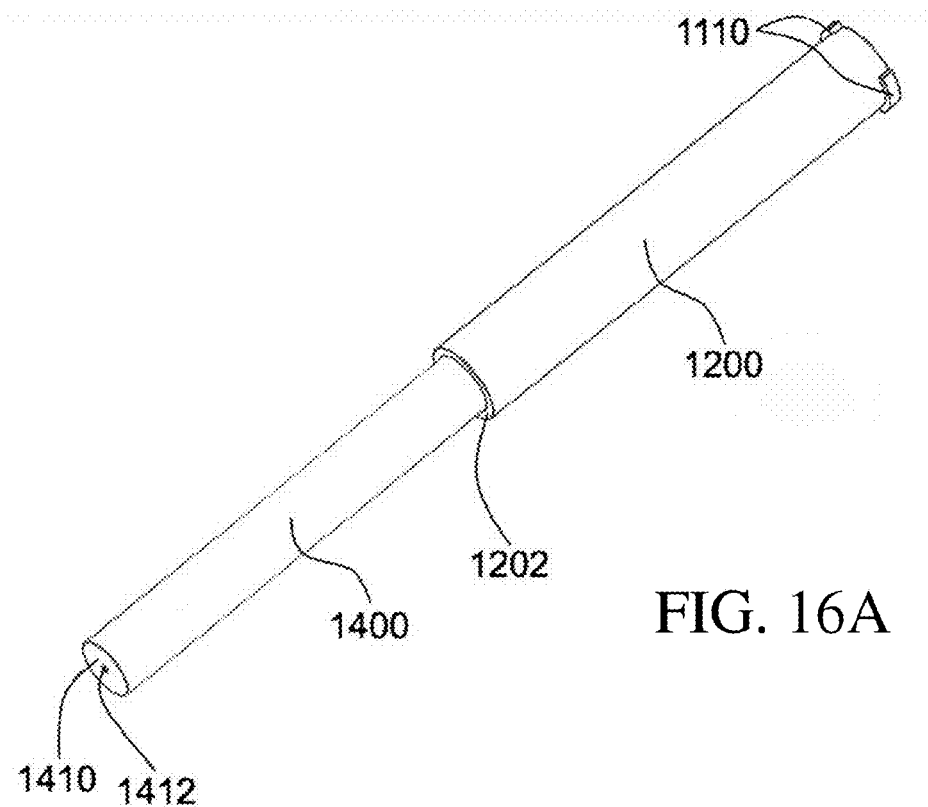
FIG. 16A shows a preferred embodiment of the delivery catheter.

FIG. 16A is a perspective view of the outside of the delivery catheter. A luer lock 1110 is opposite the distal end 1410 of the distal sheath 1400.

Figure 16B:
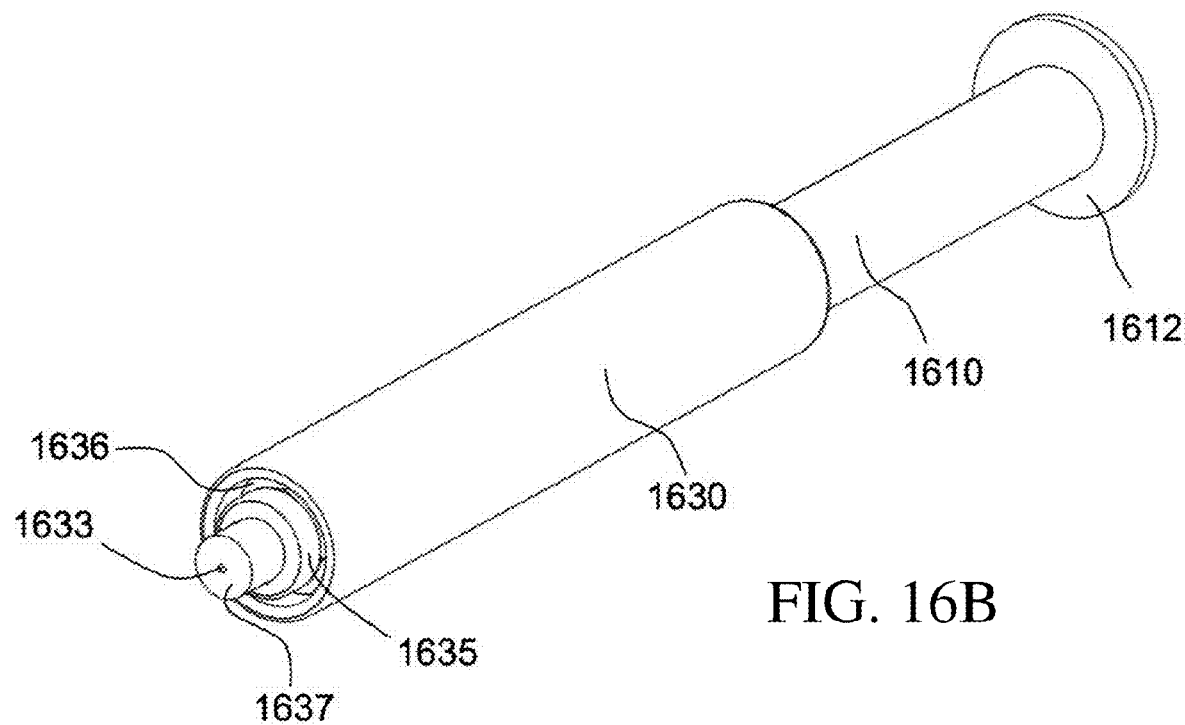
FIG. 16B shows a syringe embodiment of the delivery catheter.

FIG. 16B is an alternative syringe-like embodiment of delivery catheter 1000 within the broadest scope of the present technology. The syringe plunger 1610 and plunger housing 1630 telescope forward to progress the cannula through the distal end of the chamber 1633. The figure also depicts the proximal end of the plunger 1612 and the distal end of the housing 1637. The housing 1630 contains an air vent path 1636 to let air out as the plunger 1610 is depressed. The housing also has a ridge 1635 to prevent to housing 1630 from begin further inserted into another environment.

Figure 16C:
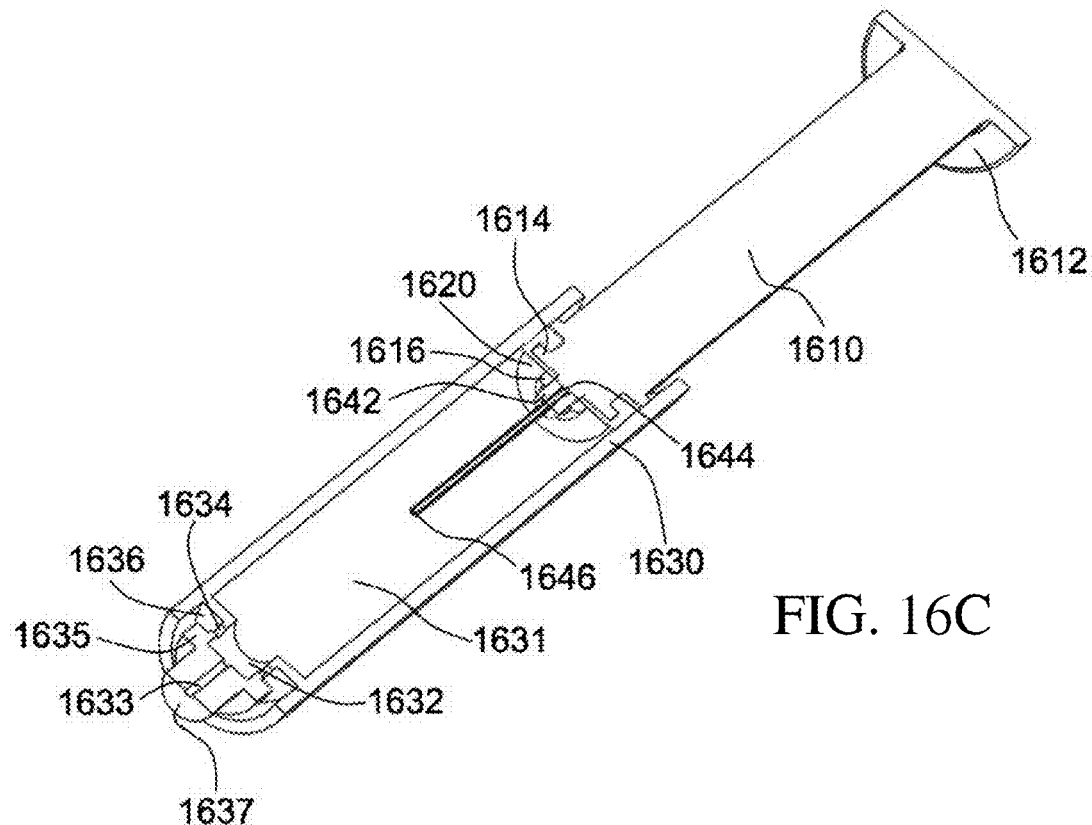
FIG. 16C shows a cross section of a syringe embodiment during operation in position 1.

FIG. 16C is a cross section of the syringe embodiment of FIG. 16B (in nominal Position 1) where the proximal end of the sampling cannula 1644 is attached to the plunger 1610 by the cannula base 1642 fitting inside the holder 1616 on the plunger. The distal end of the cannula 1646 is also shown. The plunger is covered by a rubber seal 1620 to maintain the vacuum seal. The plunger is also ridged 1614 at the end so the rubber cover 1620 remains attached to it. The housing 1630 has an internal chamber for the plunger 1631. The housing contains air holes 1634 to allow air to flow out of the internal chamber 1631. The housing also has an internal chamber 1632 designed to fit the cannula base 1642.

Figure 16D:
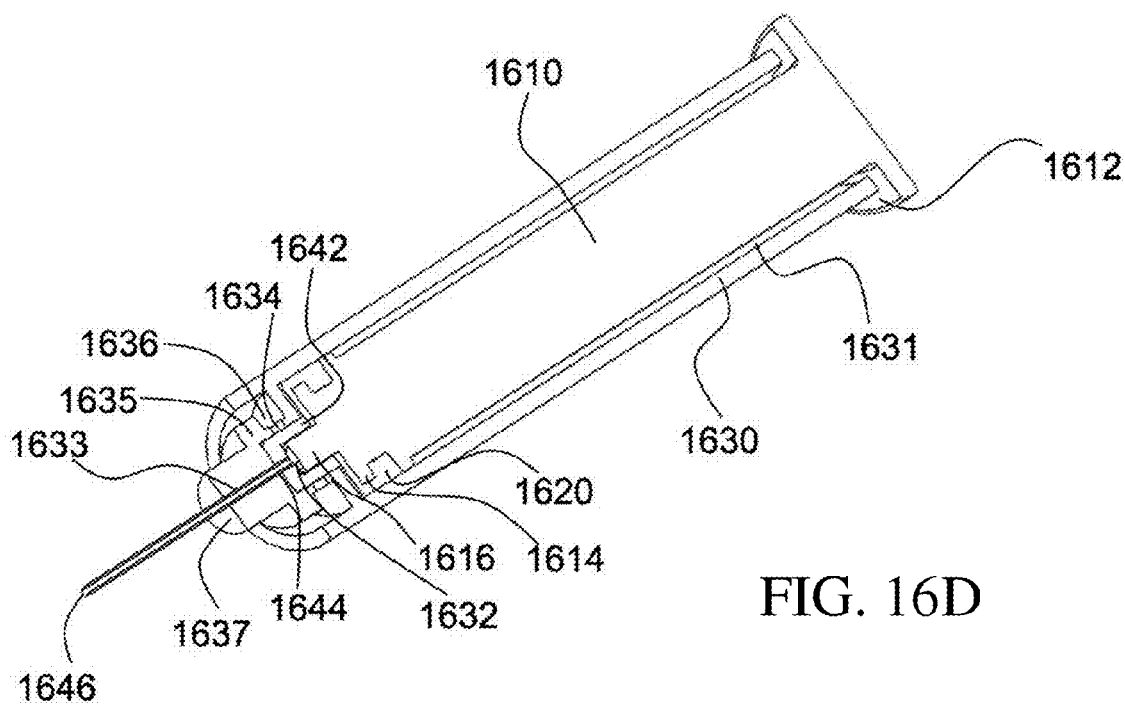
FIG. 16D shows a cross section of a syringe embodiment during operation in position 2.

FIG. 16D is a cross section of the syringe embodiment wherein a plunger 1610 is fully depressed and the sampling cannula and its cannula base 1642 are fixed into position.

Figure 16E:
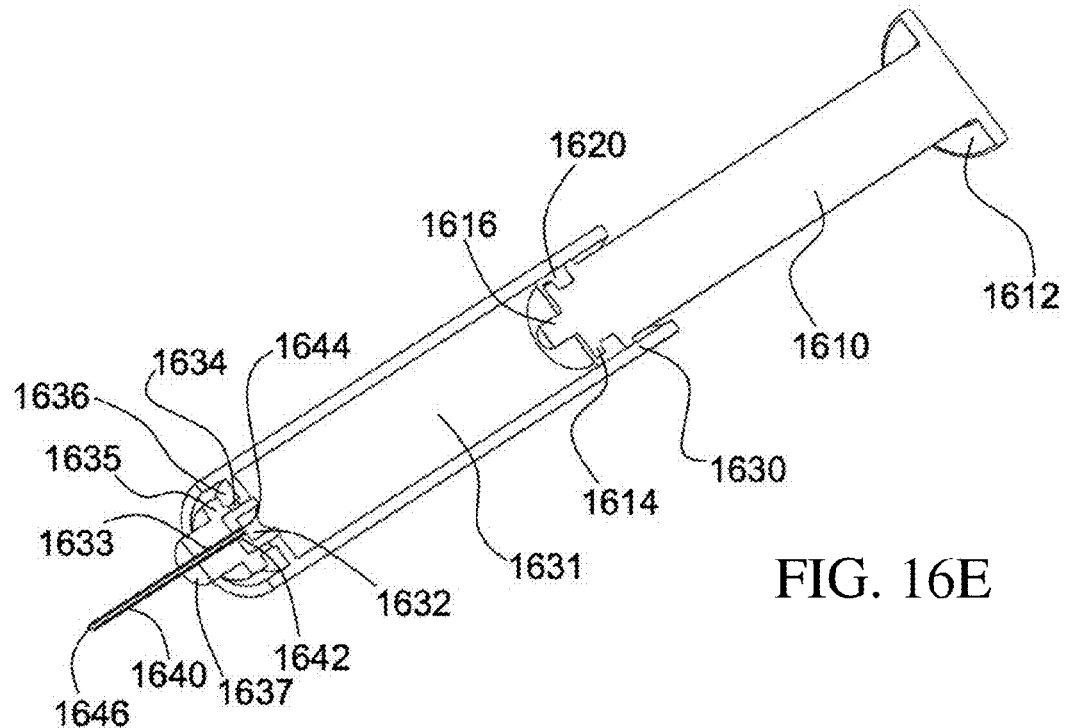
FIG. 16E shows a cross section of a syringe embodiment during operation in position 3.

FIG. 16E is a cross section of the syringe embodiment of FIG. 16B wherein a plunger 1610 is pulled back to withdraw blood into the syringe container 1631. The sampling cannula 1640 and its base 1642 stay fixed in position.

Figure 17:
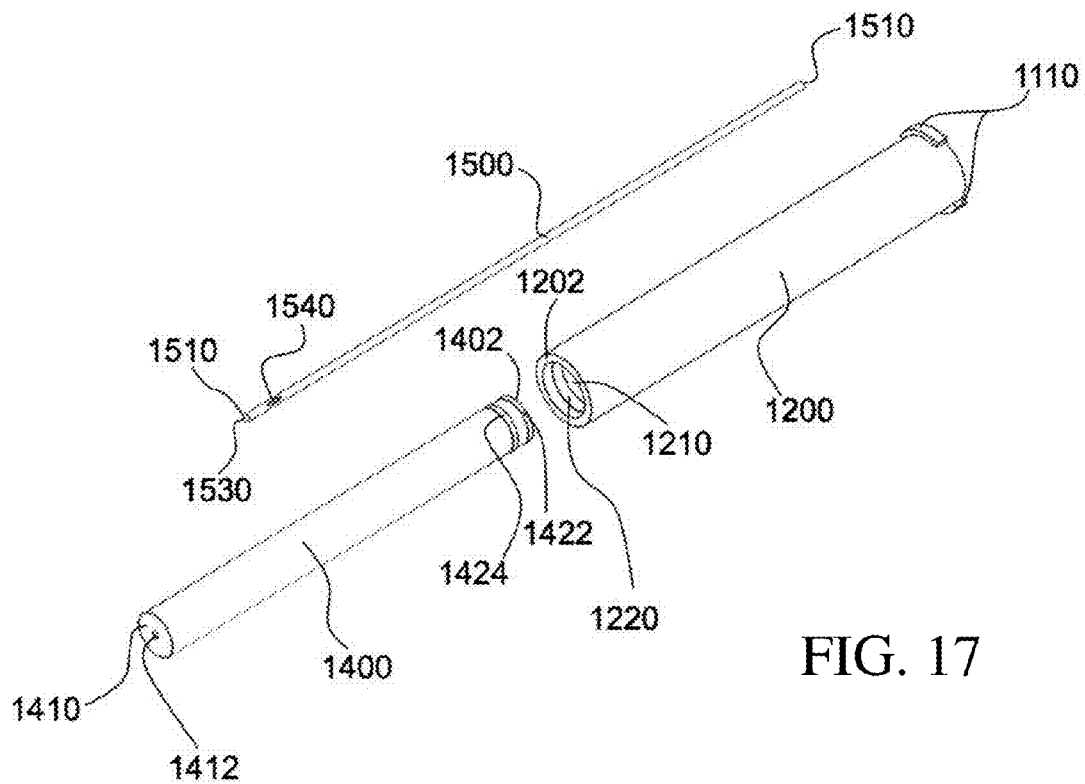
FIG. 17 shows an exploded view of the outside of delivery catheter and its components.

FIG. 17 is an exploded perspective view of the outside of a sampling cannula 1500 within the generic scope of the present technology. The rounded tip of the sampling cannula 1530 would protrude through the opening at the end of the distal sheath 1412 when the distal sheath 1400 is retracted. The distal sheath 1400 contains ridges 1422 and 1424 that interact with the ridges 1220 of the proximal part 1200 to create some resistance to the distal sheath retraction. This force ensures the distal sheath penetrates an environmental barrier before it retracts into the proximal part 1200.

Figure 18A:
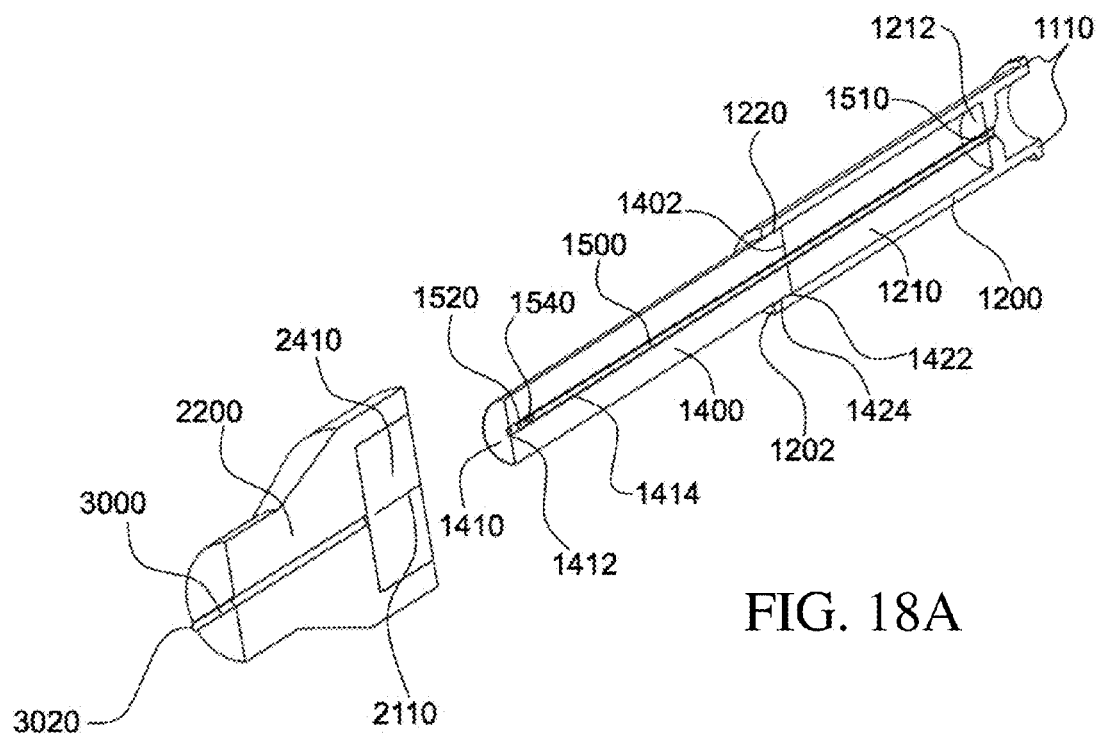
FIG. 18A shows a cross section of a delivery catheter in position 1.
Figure 18B:
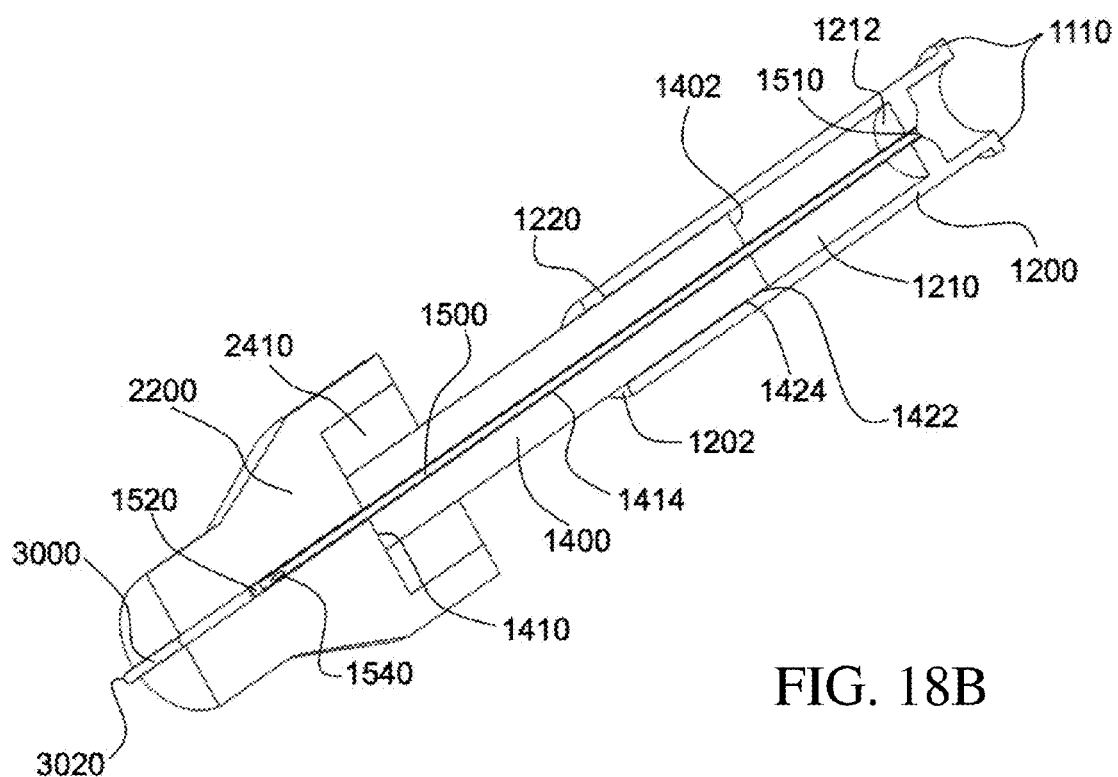
FIG. 18B shows a cross section of a delivery catheter in position 2.
Figure 18C:
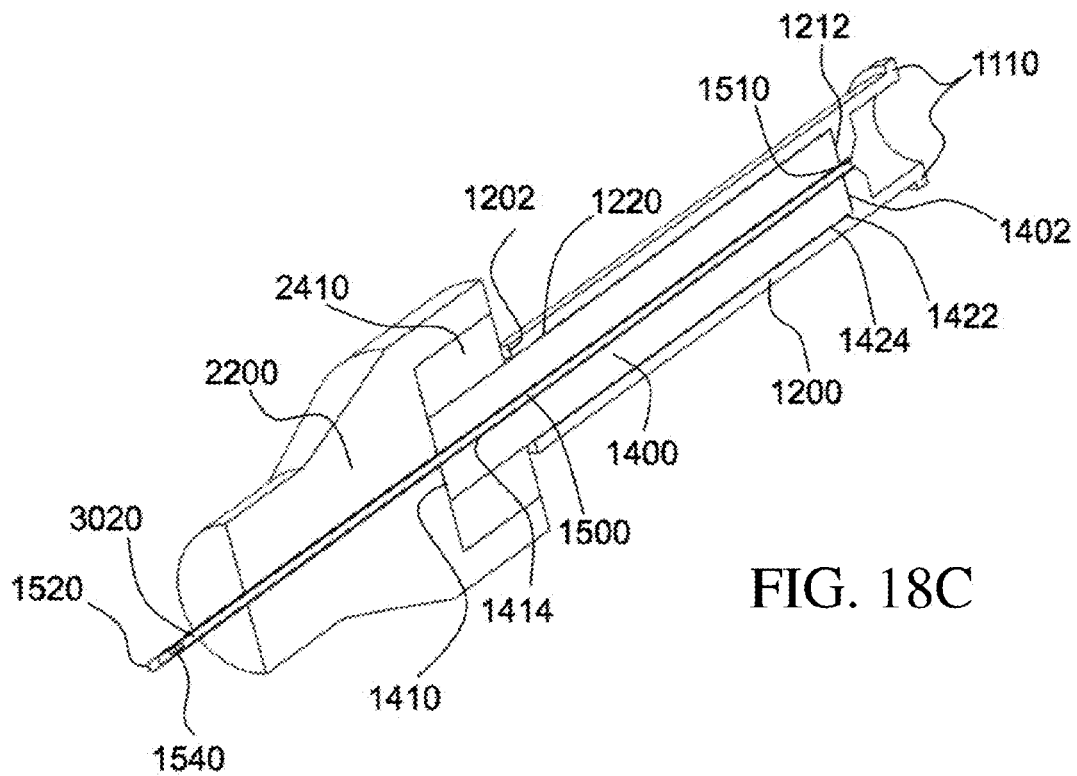
FIG. 18C shows a cross section of a delivery catheter in position 3.

FIGS. 18A, 18B and 18C show more detailed cross-sectioned views of FIGS. 13A, 13B, and 13C, in nominal positions 1, 2 and 3, respectively, with the elements described in the keys herein, and the relative position of elements shown with respect to the Title positions of the Figures.

FIGS. 19A-H shows a range of side views of various (but not exclusive) embodiments of the delivery catheter 1000 designs with various functional characteristics. This is a perspective view of all the parts that make up the preferred embodiment of the delivery catheter.

Figure 19A:
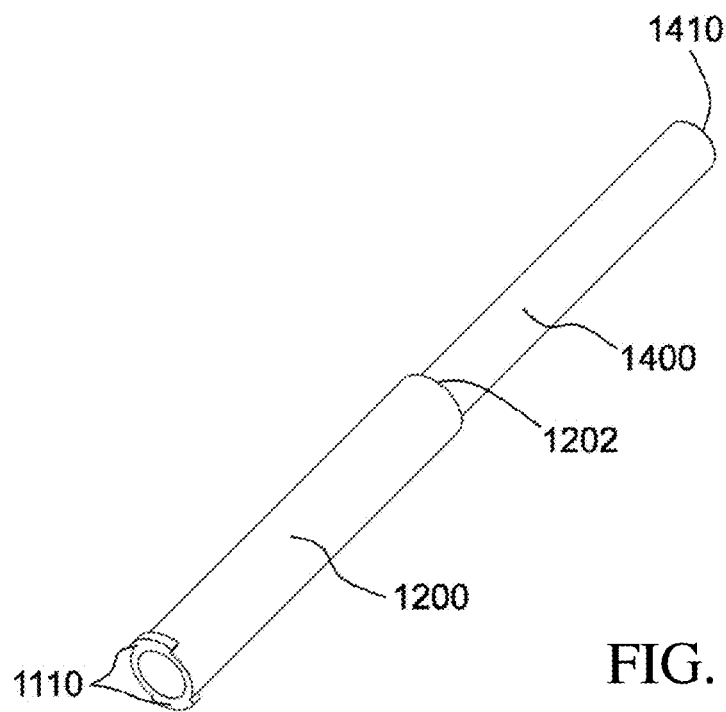
FIG. 19A shows a perspective view of an embodiment of the delivery catheter liquid collection method featuring a luer lock.

FIG. 19A shows a Luer lock connector 1110.

Figure 19B:
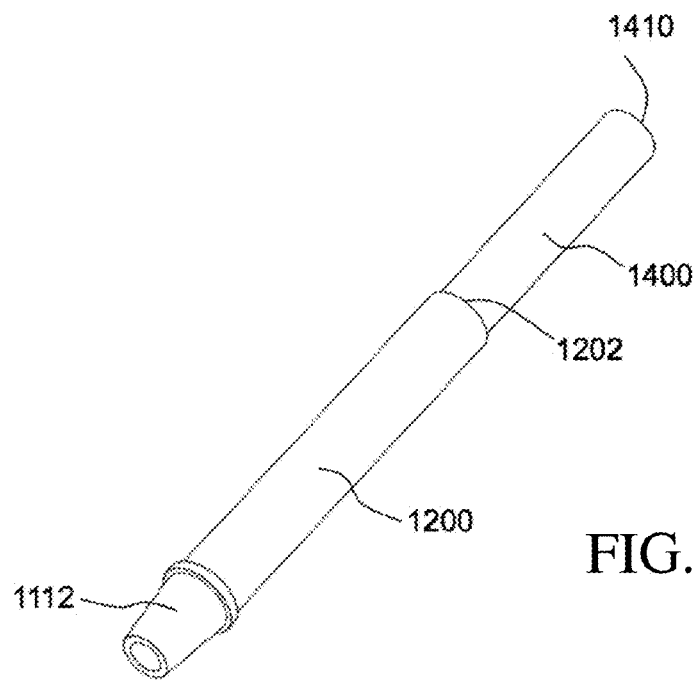
FIG. 19B shows a perspective view of an embodiment of the delivery catheter liquid collection method featuring a luer slip.

FIG. 19B shows a Luer Slip connector 1112.

Figure 19C:
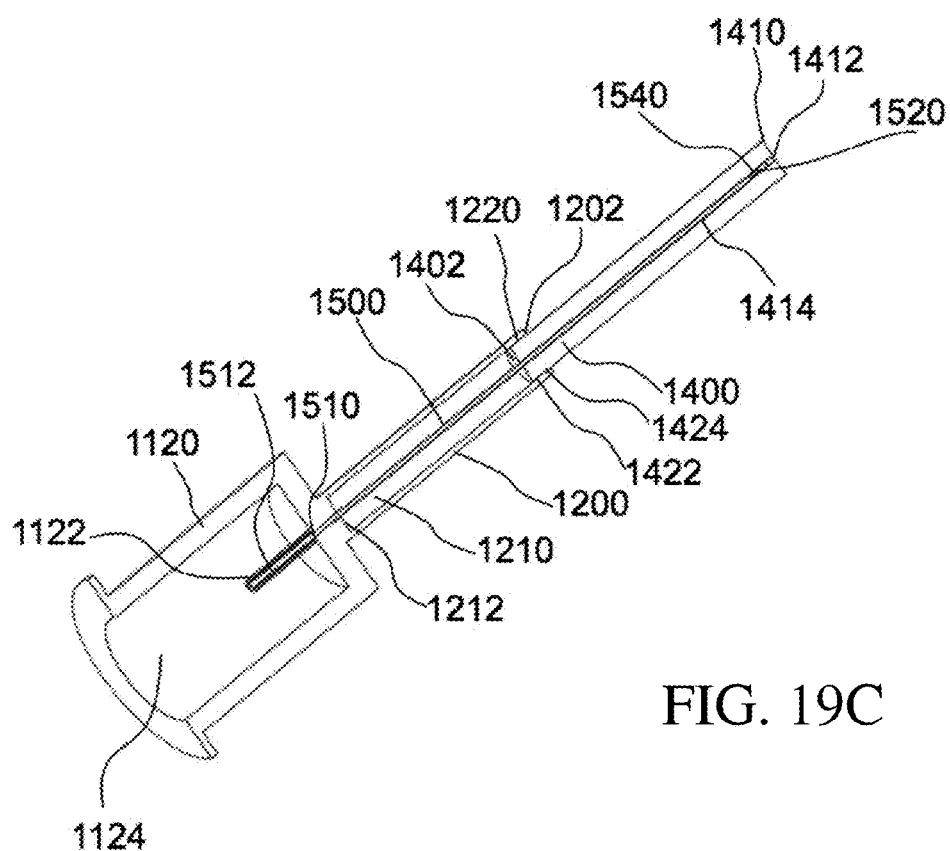
FIG. 19C shows a cross section view of an embodiment of the delivery catheter liquid collection method featuring a vacutainer collection device.

FIG. 19C shows a proximal end of the cannula 1510 as a sharp needle covered by a rubber housing 1122. This embodiment houses a traditional collection tube chamber housing 1120 and an internal space 1124 to receive a collection tube.

Figure 19D:
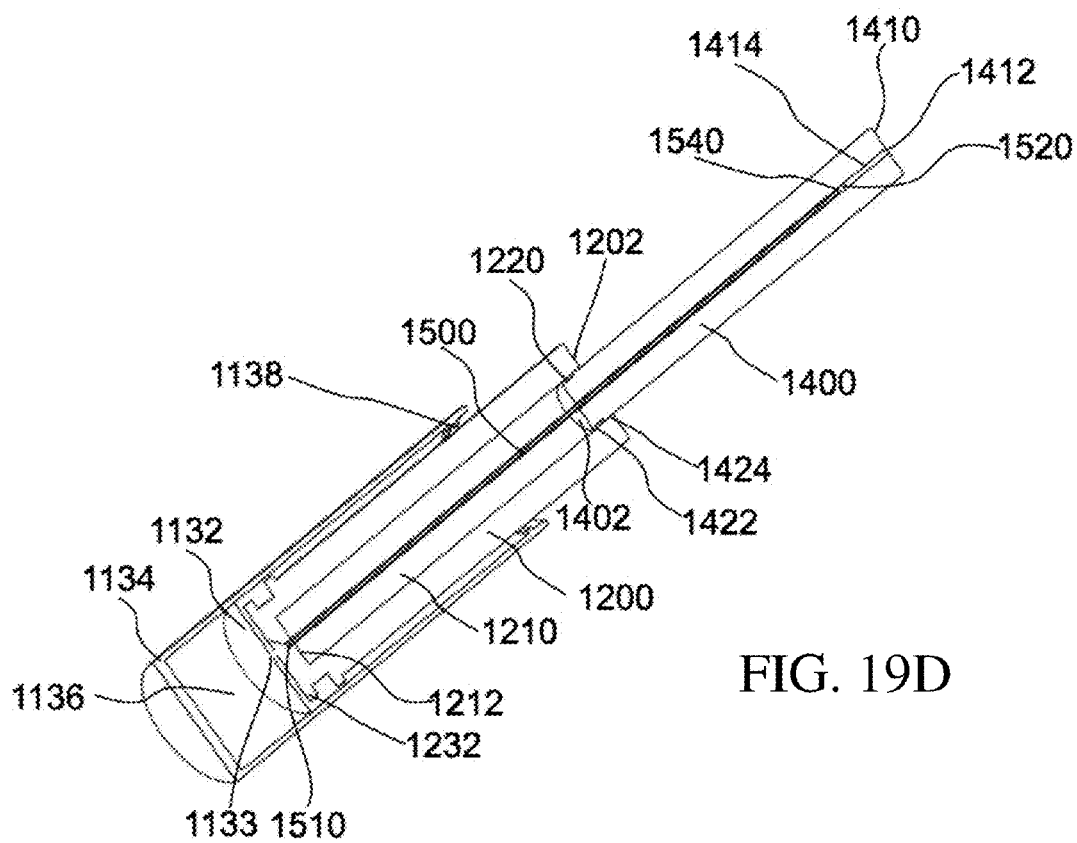
FIG. 19D shows a cross section view of an embodiment of the delivery catheter liquid collection method featuring a reverse syringe.

FIG. 19D shows a reverse syringe configuration of a delivery catheter 1000 concept within the generic scope of the present technology. The proximal part 1200 has a proximal ridged end 1232 configured to hold a rubber cover 1132. This rubber cover maintains the vacuum as the cover 1134 is pulled back. The vacuum causes blood to flow through the hole in the rubber cover 1133 and into the inner chamber where liquid can be held 1136. The cover has a distal ridge 1138 to prevent it from being completely removed from covering the proximal part 1200.

Figure 19E:
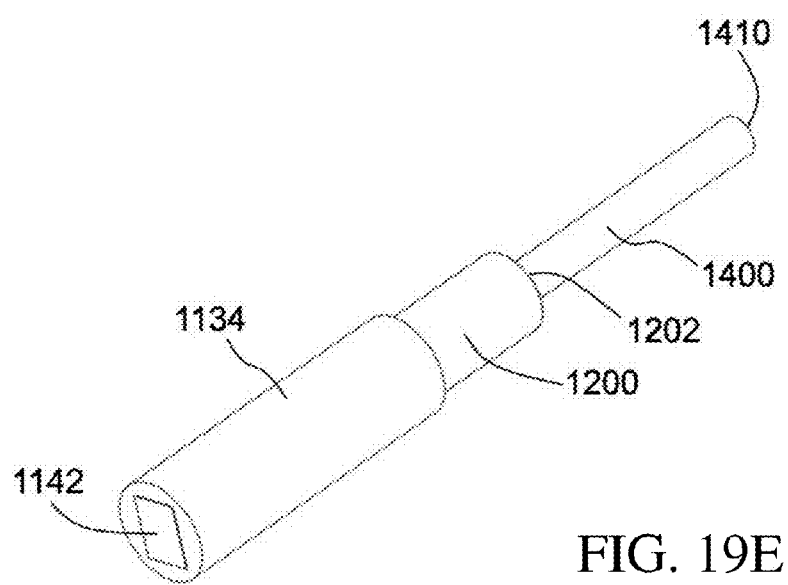
FIG. 19E shows a perspective view of an embodiment of the delivery catheter liquid collection method featuring a reverse syringe with back opening.

FIG. 19E shows a reverse syringe configuration of a delivery catheter 1000 within the generic scope of the present technology with a door 1142 on the back through which access to a liquid sample can be made.

Figure 19F:
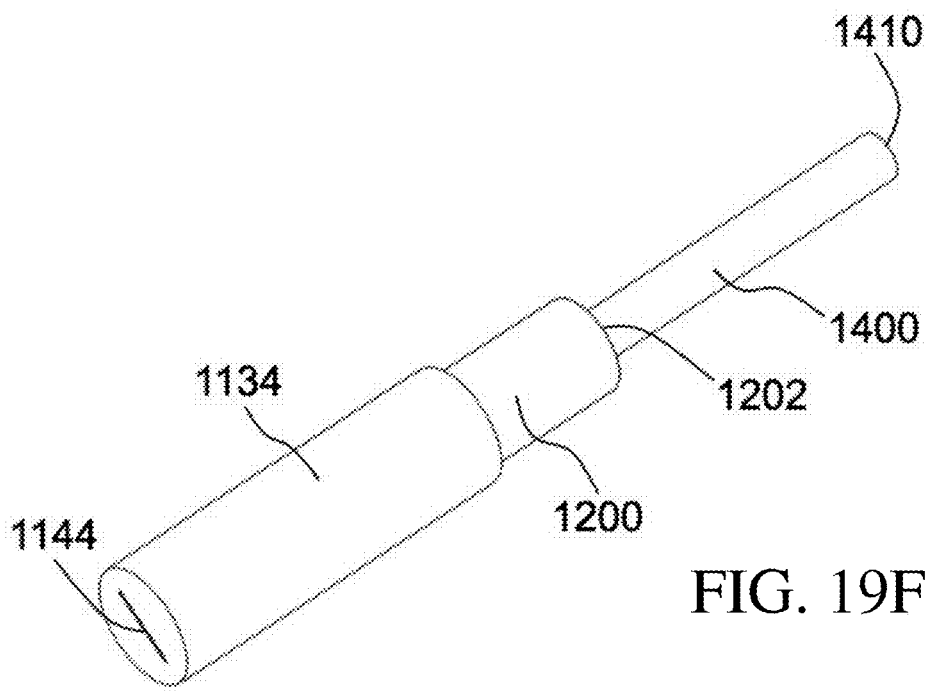
FIG. 19F shows a perspective view of an embodiment of the delivery catheter liquid collection method featuring a reverse syringe with back slit.

FIG. 19F shows a reverse syringe configuration of a delivery catheter 1000 within the generic scope of the present technology with a slot 1144 on the back for sample access. An object could be inserted through the slot 1144 and a vacuum will still be maintained.

Figure 19G:
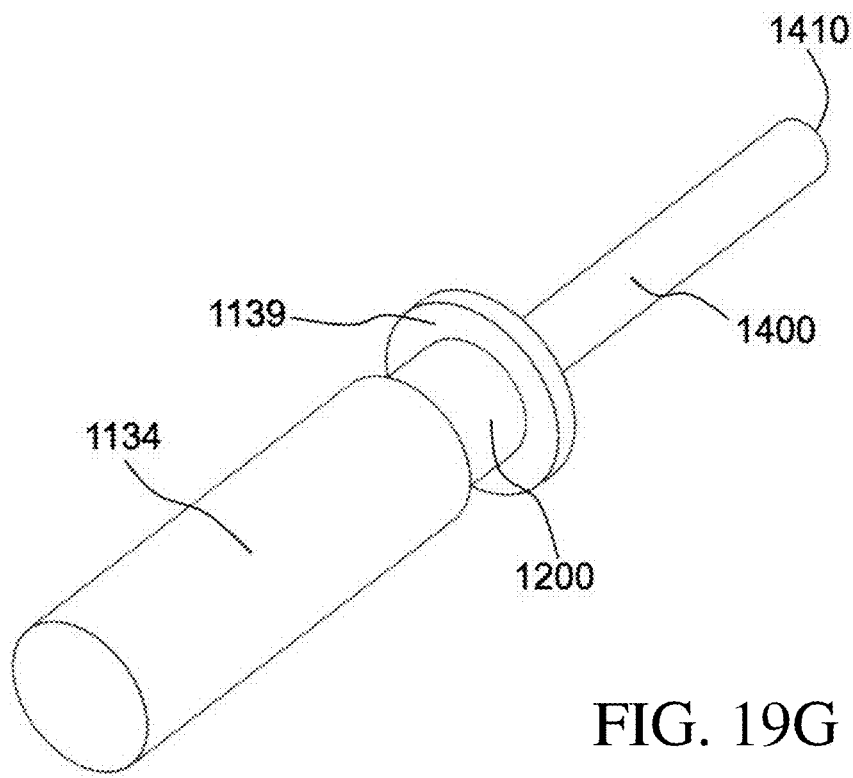
FIG. 19G shows a perspective view of an embodiment of the delivery catheter liquid collection method featuring a reverse syringe with push finger slide cover.

FIG. 19G shows a reverse syringe configuration of a delivery catheter 1000 within the generic scope of the present technology with a finger slide 1139 which can be used to push up the cover 1134.

Figure 19H:
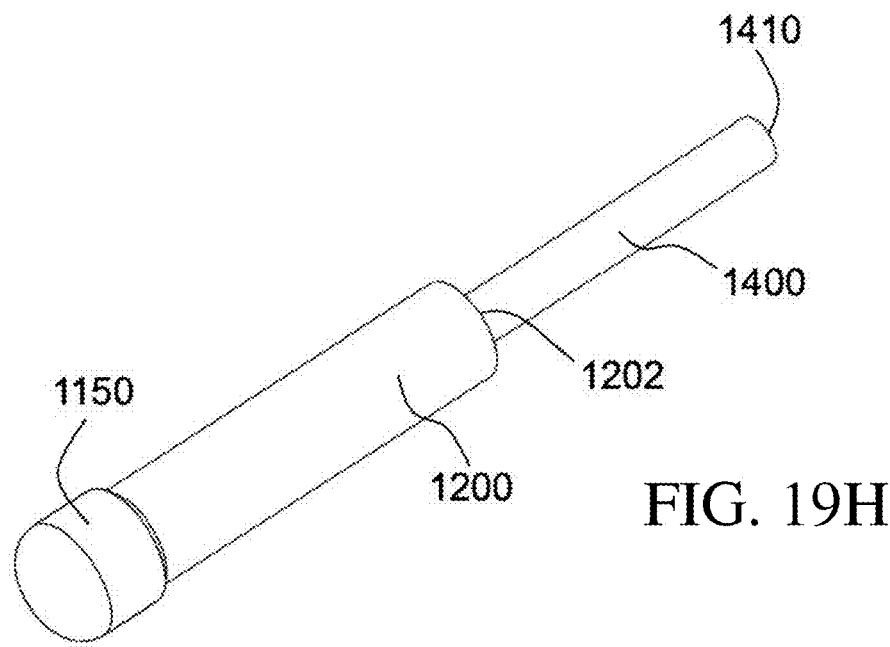
FIG. 19H shows a perspective view of an embodiment of the delivery catheter liquid collection method featuring a pipette bulb style device.

FIG. 19H shows a delivery catheter with a pipette bulb 1150.

Figure 19I:
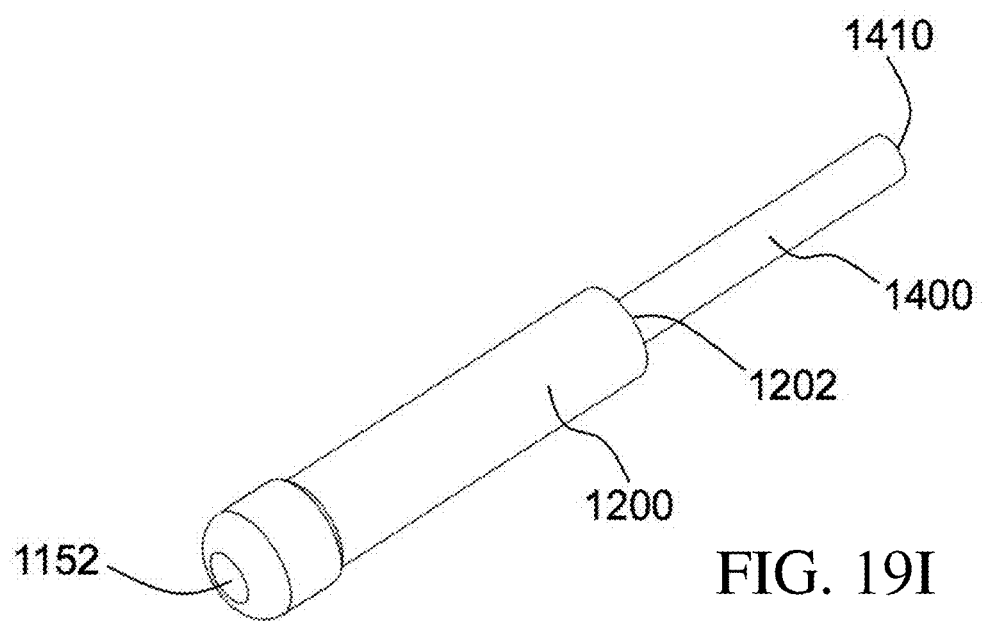
FIG. 19I shows a perspective view of an embodiment of the delivery catheter liquid collection method featuring a capillary action style device.

FIG. 19I shows an air permeable membrane 1152 on the proximal end of the delivery catheter. When the sampling cannula is inserted into the distal region of the patient, capillary action will cause the cannula to fill with liquid.

Figure 20:
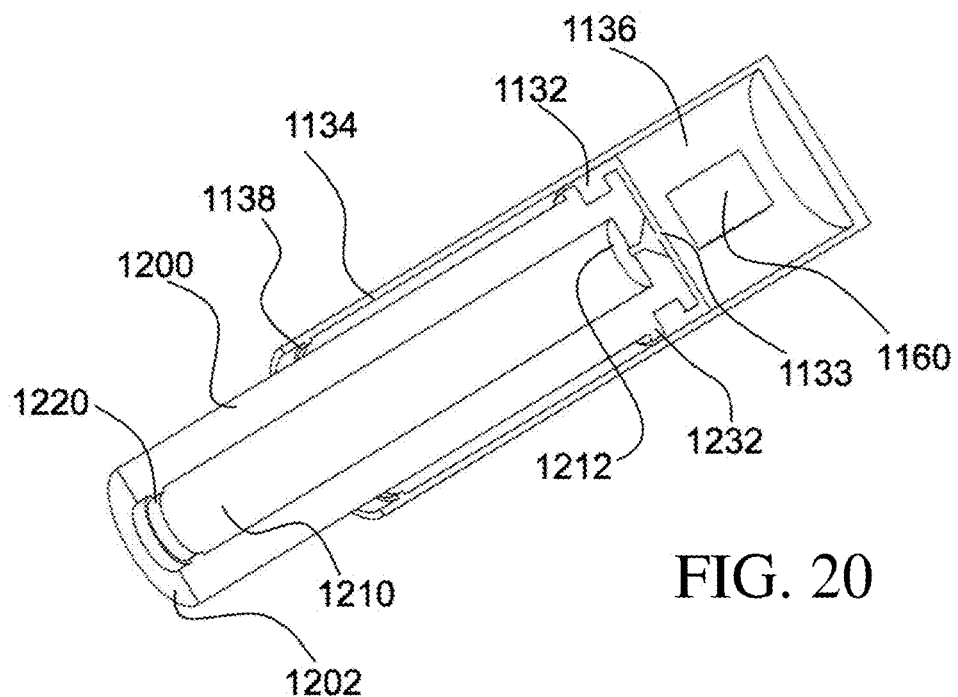
FIG. 20 shows the delivery catheter with a chemistry test incorporated into the proximal end of the device.

FIG. 20 shows a delivery catheter 1000 embodiment incorporating a specialized chemistry test component 1160 directly into the proximal end of the blood collection mechanism 1136. Any type of analyte, pH responsive, fluorescing, dye reactive, chemically reactive, resistance responsive (e.g., with electrodes not shown extending out), and other chemical testing systems and modalities known within the art may be used.

Figure 21A:
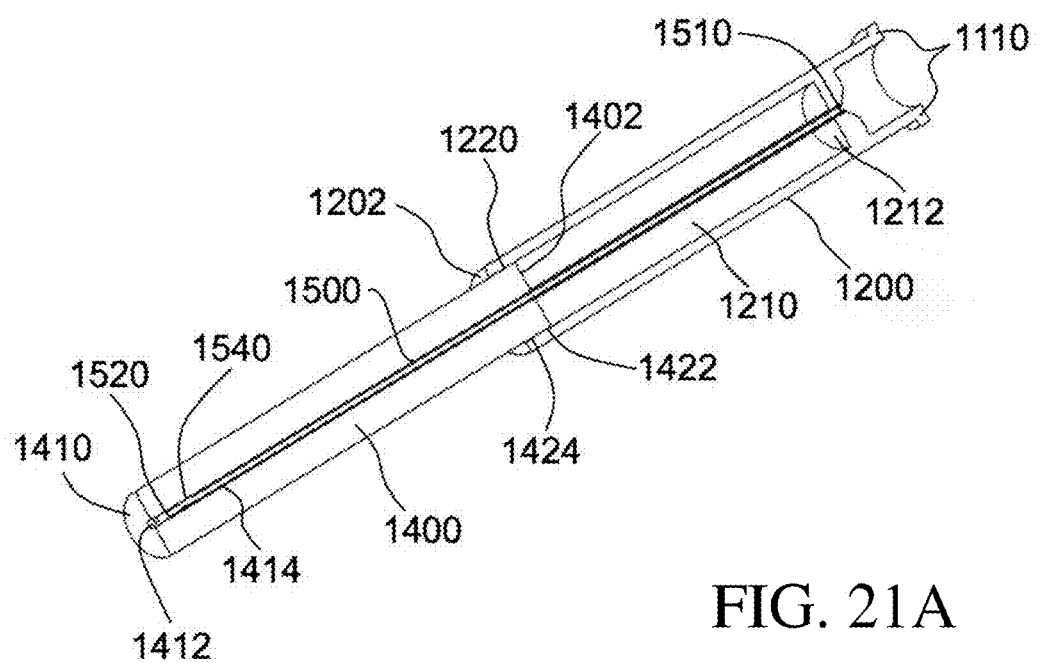
FIG. 21A shows a cross section view of a preferred embodiment of the delivery catheter.

FIG. 21A shows a cross section of the preferred embodiment of the distal sheath of the delivery catheter 1400.

Figure 21B:
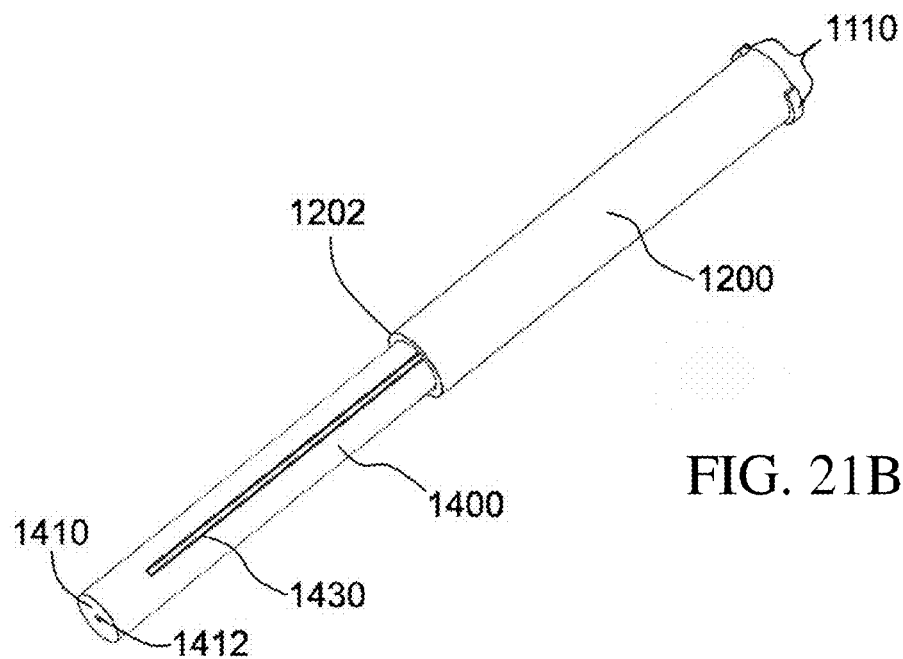
FIG. 21B shows a perspective view of the delivery catheter with air vents.

FIG. 21B shows an embodiment of the distal sheath of the delivery catheter 1400 with air vents 1430 on side to allow air to escape from the internal chamber of the proximal part.

Figure 21C:
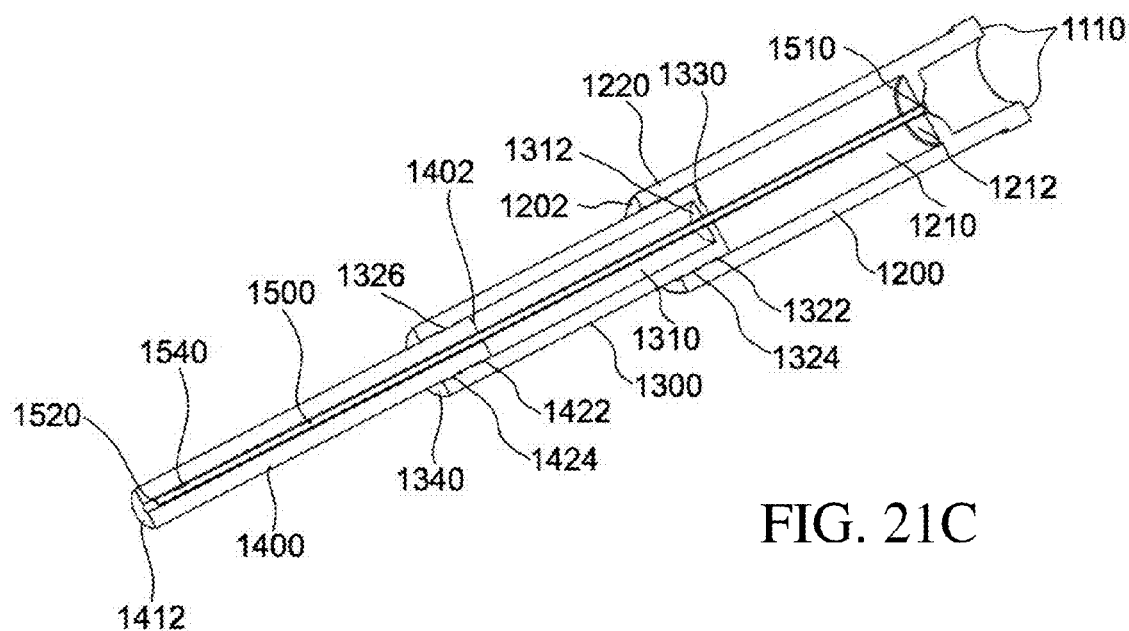
FIG. 21C shows a cross section view of an embodiment of the delivery catheter with two sheaths.

FIG. 21C shows an embodiment of the delivery catheter 1000 with a middle sheath 1300 and a distal sheath 1400. In this construction the middle sheath contains both a distal ridge 1326 and two proximal ridges 1324 and 1322 with the more distal ridge 1324 being slightly larger. The middle sheath has an internal chamber 1310 to hold the distal sheath. The proximal end of the internal chamber 1312 and the sheath itself 1330 is closed to prevent the distal sheath 1400 from entering the internal chamber of the proximal part 1210.

Figure 21D:
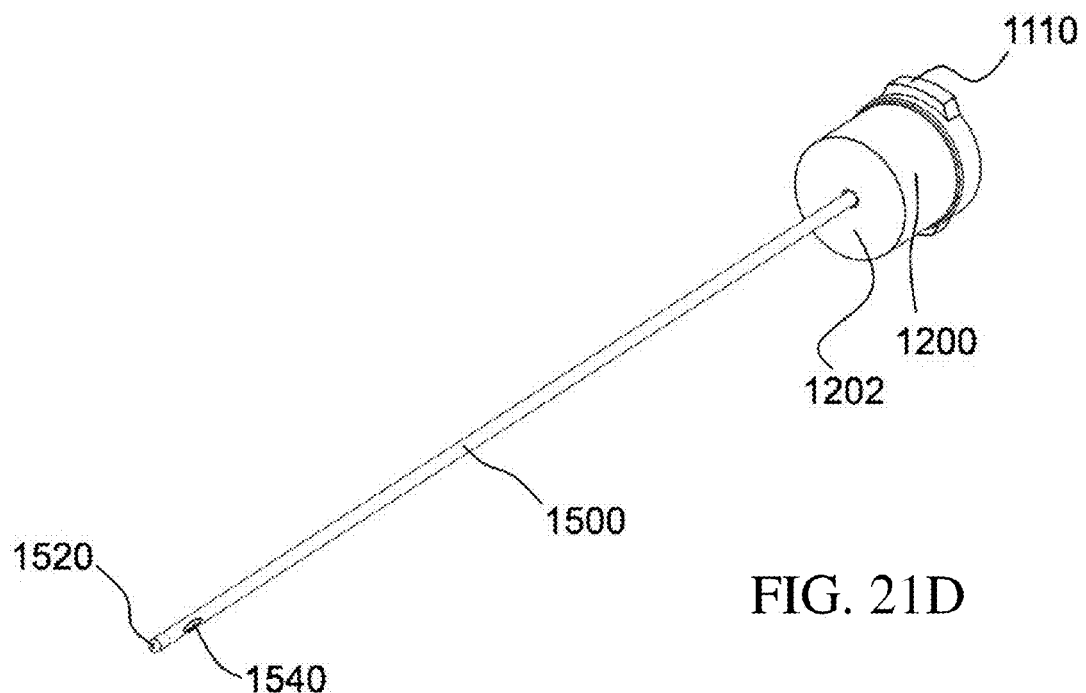
FIG. 21D shows a perspective view an embodiment of the sampling cannula without a sheath.

FIG. 21D has a shortened proximal part 1200 and no retracting sheath.

Figure 21E:
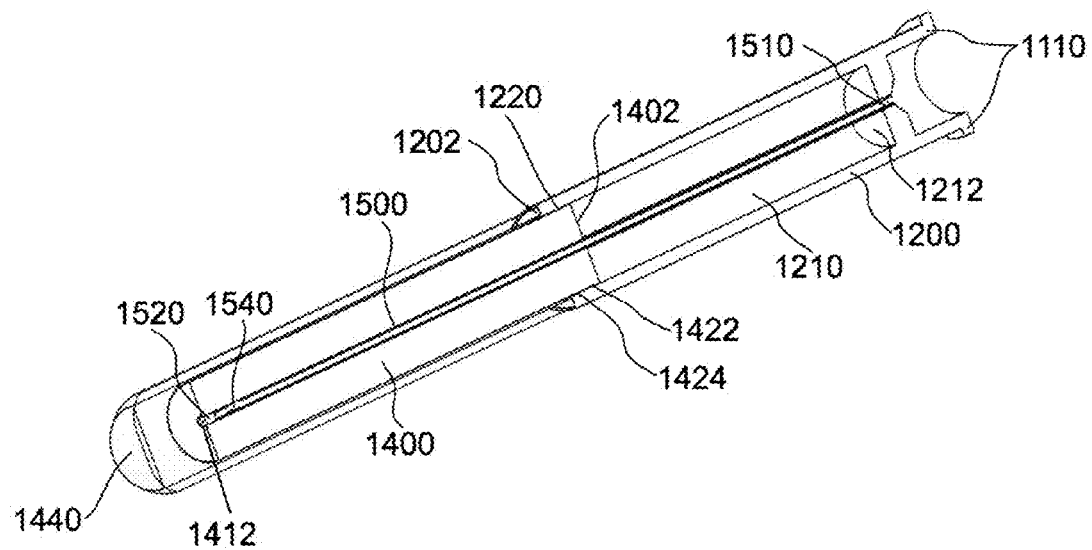
FIG. 21E shows a cross section view of embodiment of the delivery catheter with a protective cover over the distal end.

FIG. 21E shows a cap 1440 that covers the distal sheath 1400. The cap 1440 is removed prior to operation.

Figure 21F:
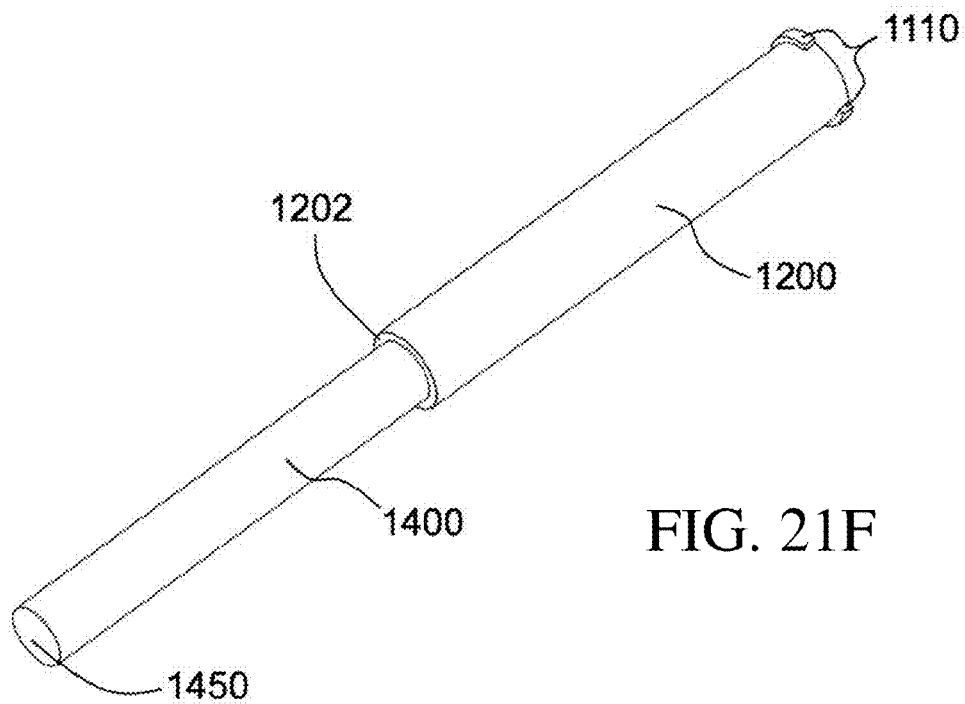
FIG. 21F shows a perspective view an embodiment with a sterile barrier cover on the distal end of the delivery catheter.

FIG. 21F shows an embodiment of the distal sheath 1400 with a barrier 1450 that covers the distal opening in the distal sheath 1400. This barrier 1450 is penetrated by the sampling cannula during the operation of the delivery catheter.

Figure 21G:
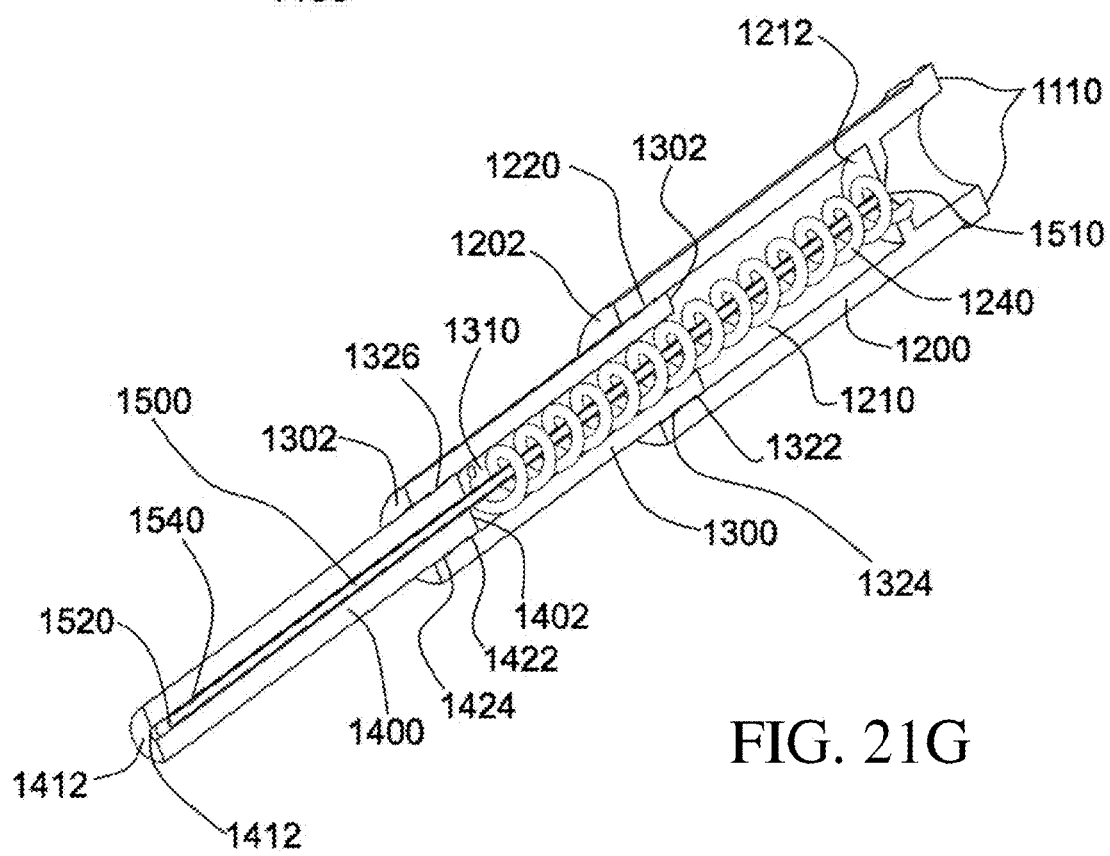
FIG. 21G shows a cross section view of an embodiment featuring an internal spring within the delivery catheter.

FIG. 21G shows an embodiment of a three part delivery catheter with an internal spring 1240. This spring is compressed during operation and ensures the middle 1300 and distal 1400 sheaths re-extend over the sampling cannula 1500 after use.

Figure 21H:
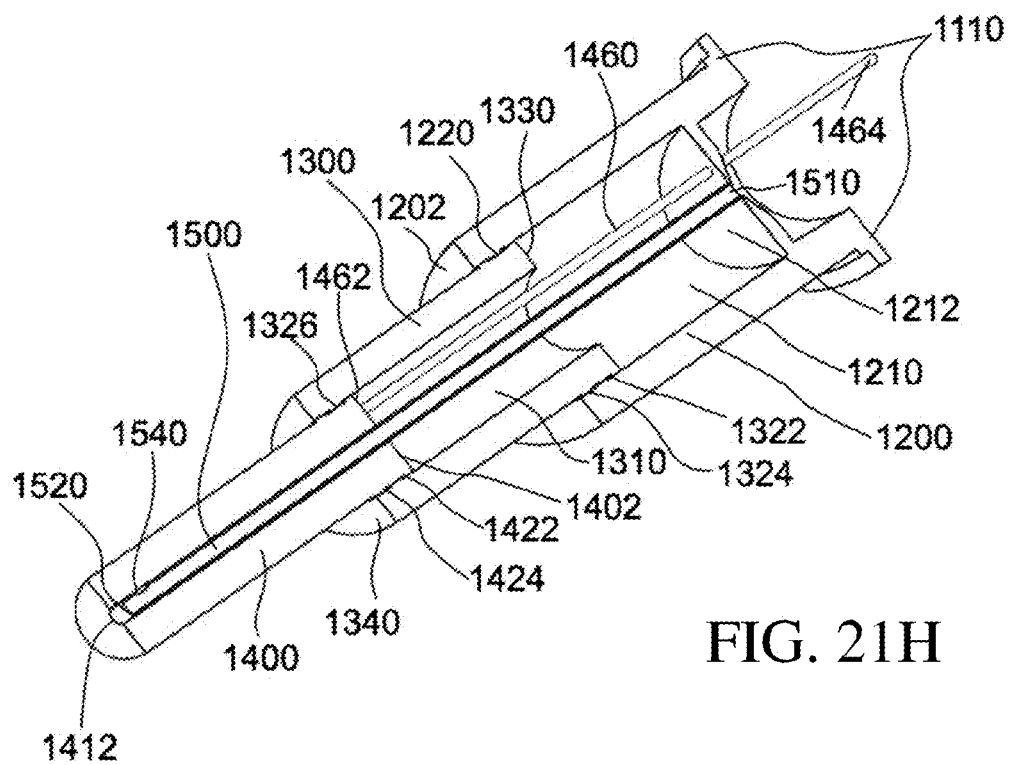
FIG. 21H shows a cross section of an embodiment featuring a guide wire within the delivery catheter.

FIG. 21H shows an embodiment of a three part delivery catheter with an internal guide wire 1460. The distal end of the wire 1462 connects to the proximal end of the distal sheath 1402. The proximal end of the wire 1464 can be manipulated to re-extend or retract the parts of the delivery catheter.

Figure 22:
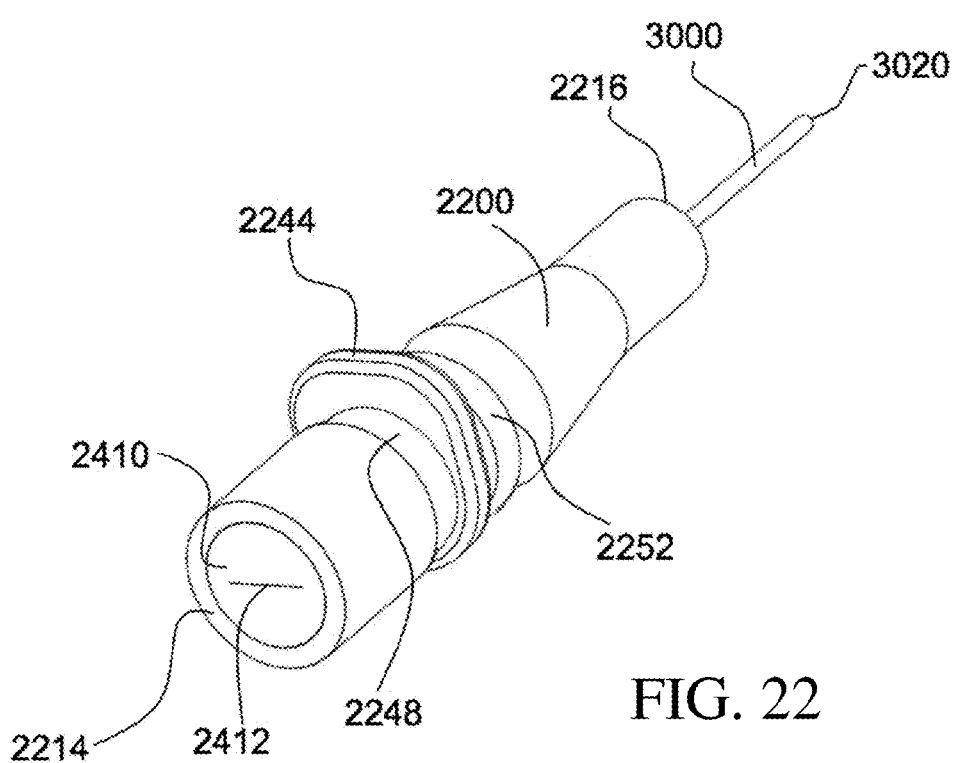
FIG. 22 shows a perspective view of an embodiment of the sampling hub.

FIG. 22 shows an embodiment of the sampling hub 2200 with a finger grip 2244 and a distal grove 2252 to hold the part. The sampling hub lumen 3000 extends past the distal part of the sampling hub 2216. The sampling hub 2200 has a secondary finger depression 2248 for improved grip. The proximal end of the sampling hub 2214 contains a valve that creates a barrier between the outside environment and the inside of the sampling hub. In this embodiment the valve is a split septum 2410 with a slit 2412 that allows it to be opened upon interaction with an external object.

Figure 23:
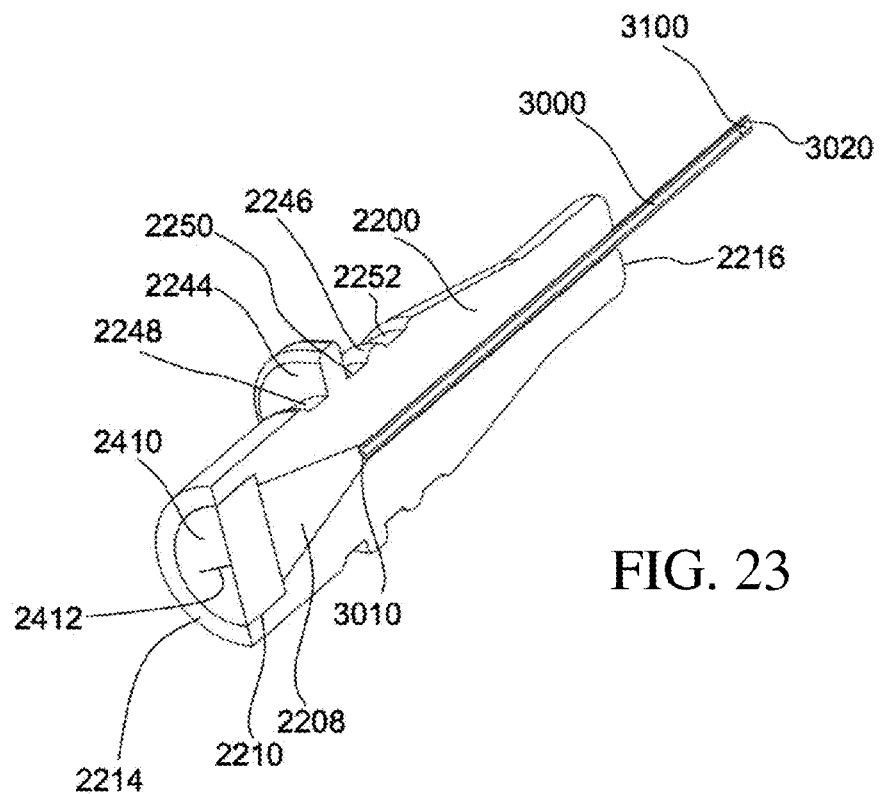
FIG. 23 shows a cross section of an embodiment of the sampling hub.

FIG. 23 shows a cross section of the sampling hub 2200. The sampling hub has a proximal 2214 and a distal 2216 end. The distal end of the lumen 3020 contains a valve 3100 which prevents backflow of liquid. The sampling hub also contains an alignment chamber 2208 to ensure a foreign body inserted through the septum slit 2412 can be aligned to pass through the lumen 3000. The sampling hub 2200 also has an additional finger depression 2250 for maximal grip.

Figure 24:
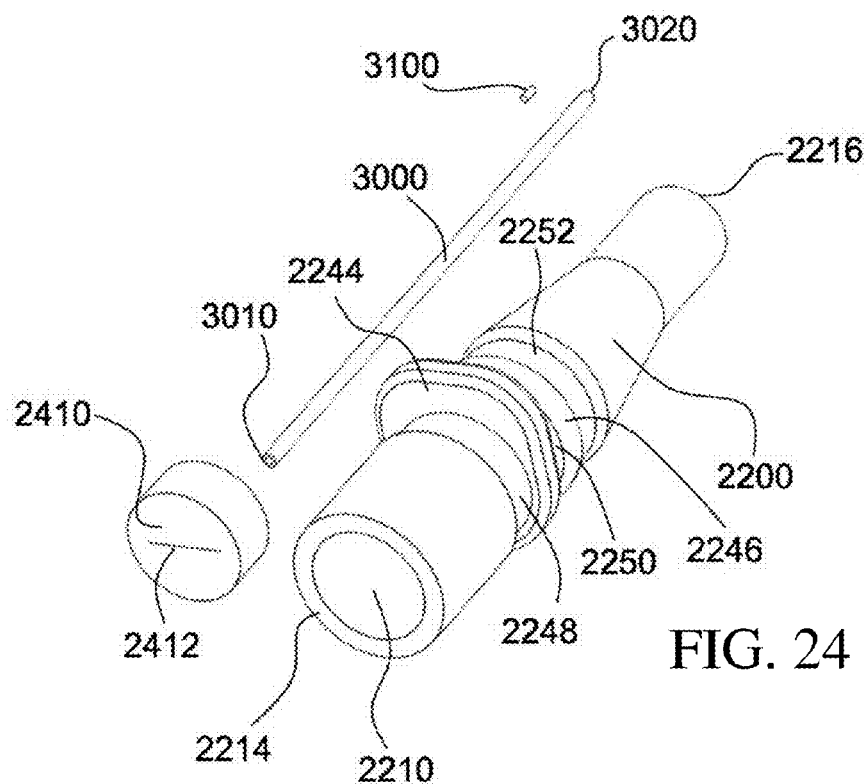
FIG. 24 shows a perspective exploded view of an embodiment of the sampling hub.

FIG. 24 is an exploded view of the sampling hub 2200. The distal valve 3100 is depicted here as a separate part, but could be directly incorporated into the lumen 3000.

Figure 25A:
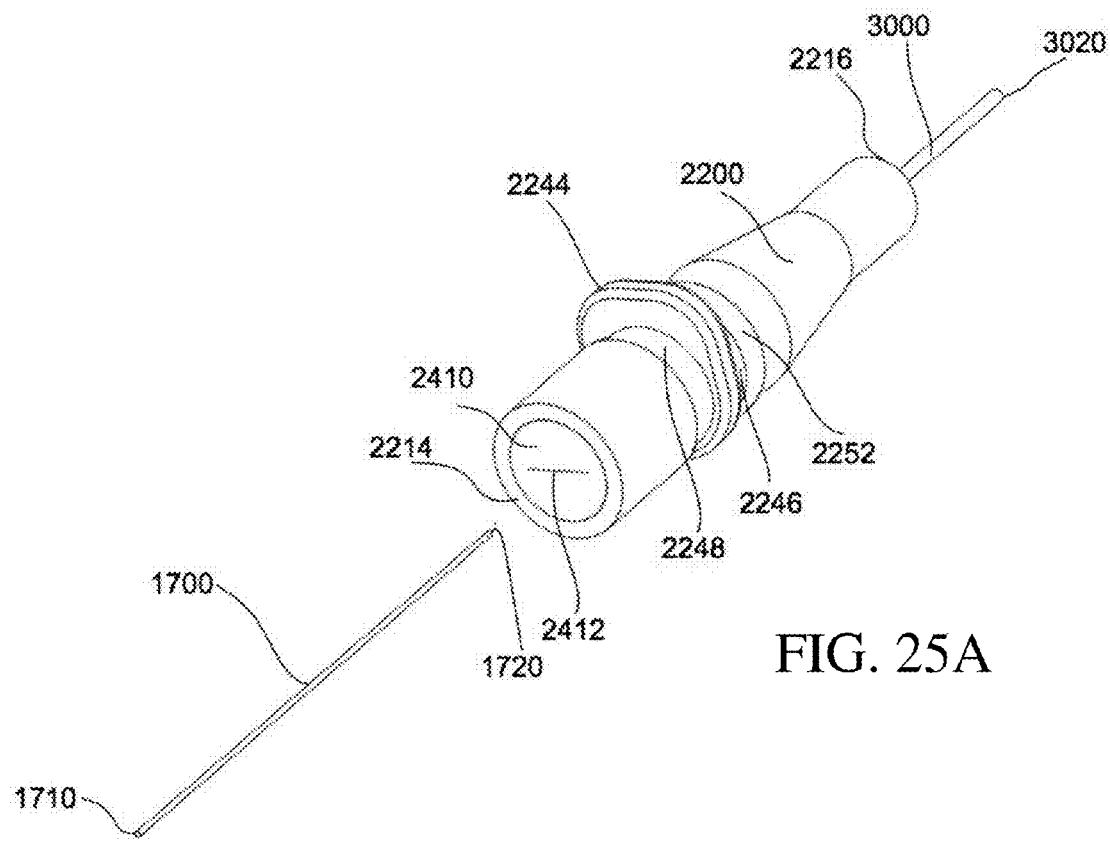
FIG. 25A shows a perspective view of an embodiment of the sampling hub with a probe or cannula being inserted through it during operation in position 1.
Figure 25B:
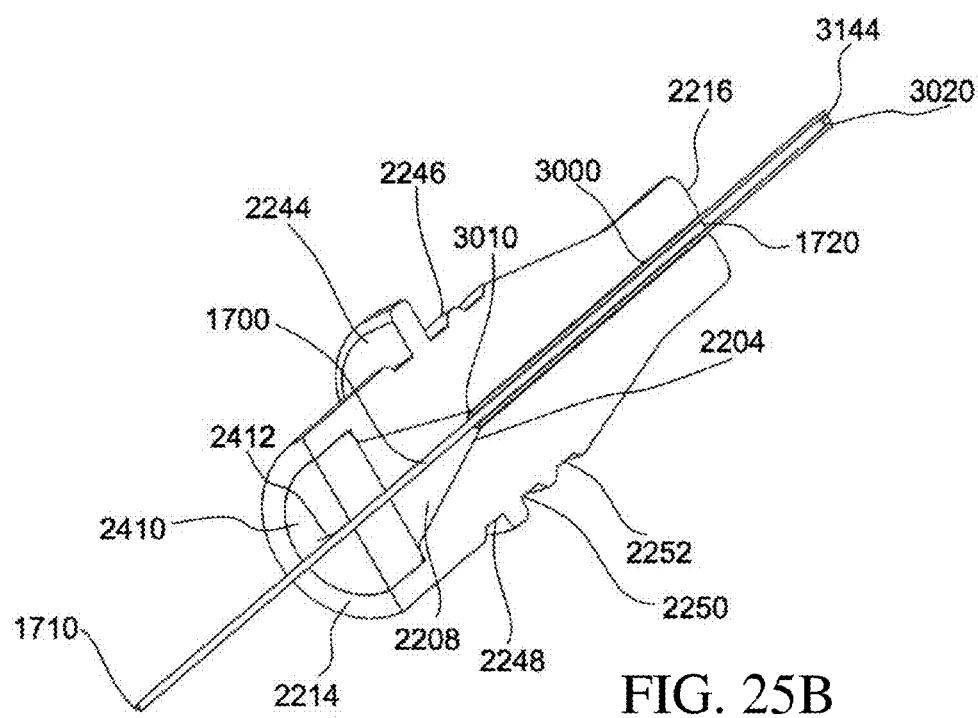
FIG. 25B shows a cross section view of an embodiment of the sampling hub with a probe or cannula being inserted through it during operation in position 2.
Figure 25C:
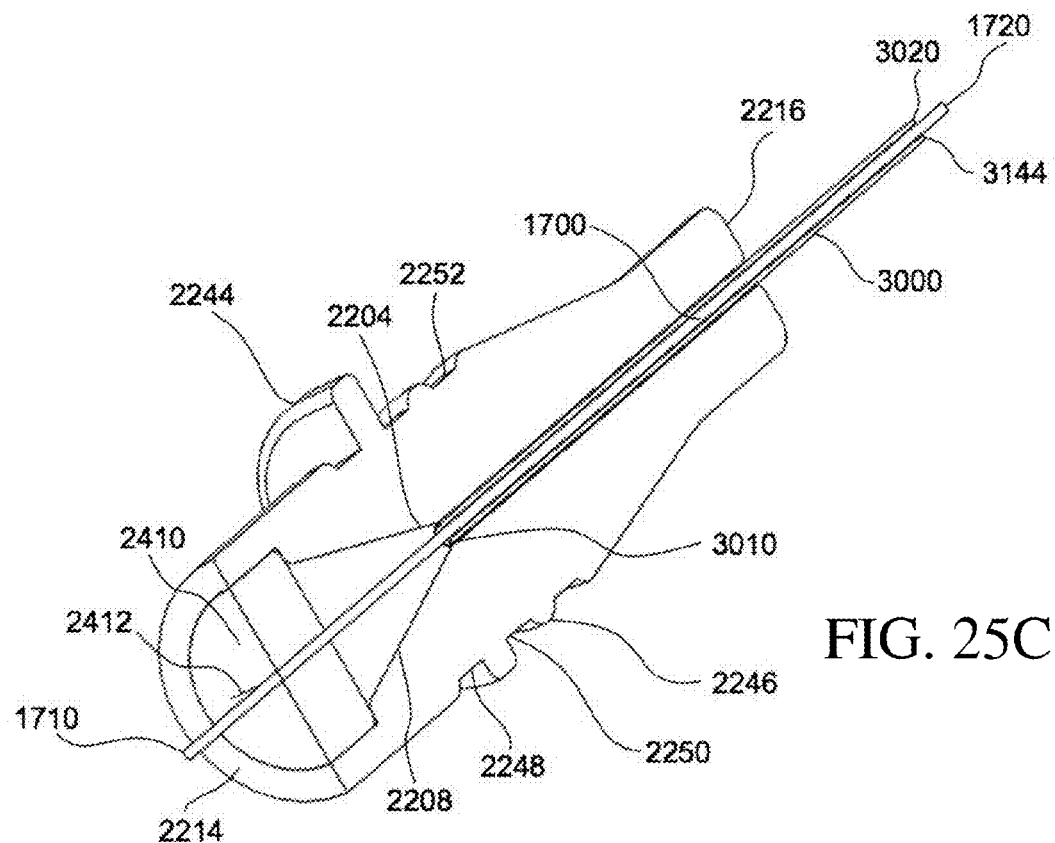
FIG. 25C shows a cross section view of an embodiment of the sampling hub with a probe or cannula being inserted through it during operation in position 3.

FIGS. 25A, 25B and 25C show more detailed views of FIGS. 15A, 15B, and 15C, in nominal positions 1, 2 and 3, respectively, with the elements described in the keys herein, and the relative position of elements shown with respect to the Title positions of the Figures.

Figure 26:
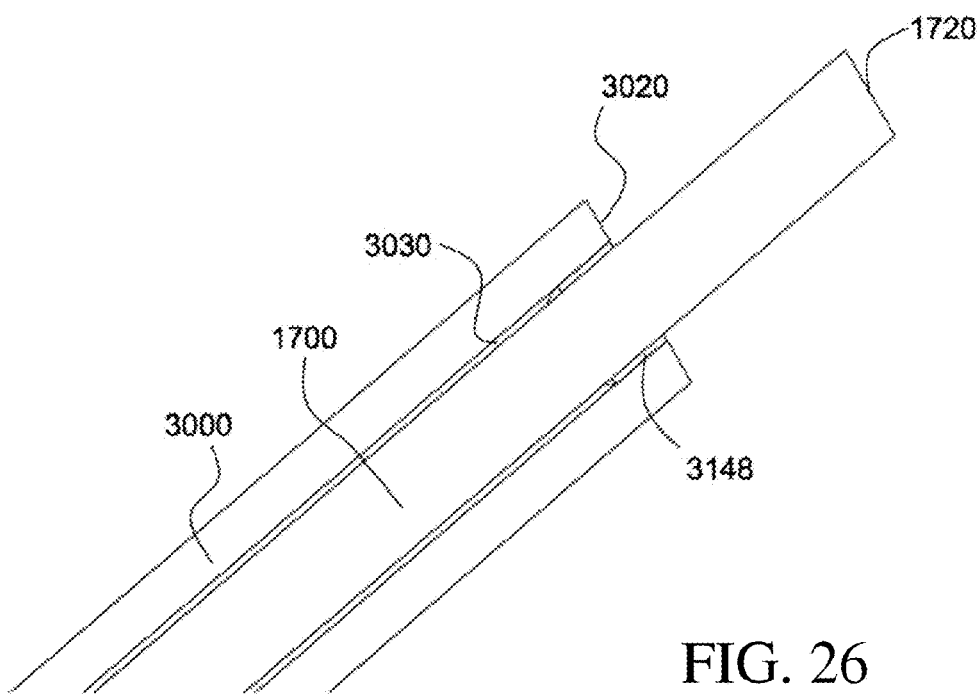
FIG. 26. shows a close up cross section view of the sampling up lumen in position 3.

FIG. 26 shows a close up of the distal portion of the sampling hub lumen 3000 when the system is in position 3. The distal end of the probe 1720 is extended past the distal end of the lumen 3020 and through the distal lumen valve, which is shown here as a split septum 3148.

Figure 27A:
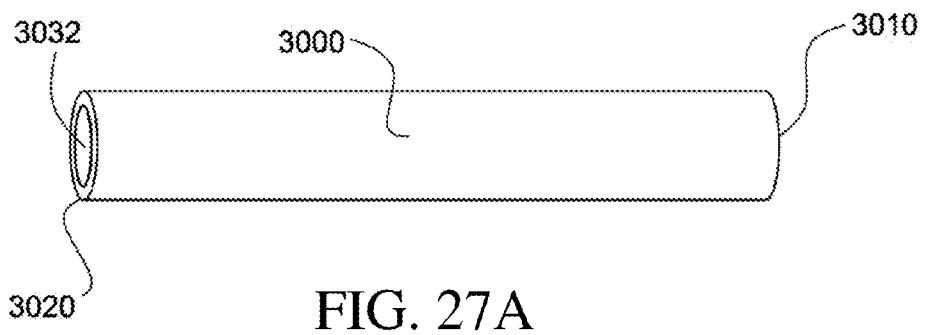
FIG. 27A shows an embodiment of the sampling hub lumen.

FIG. 27A shows the sampling hub lumen 3000 with an opening in the distal end 3032.

Figure 27B:
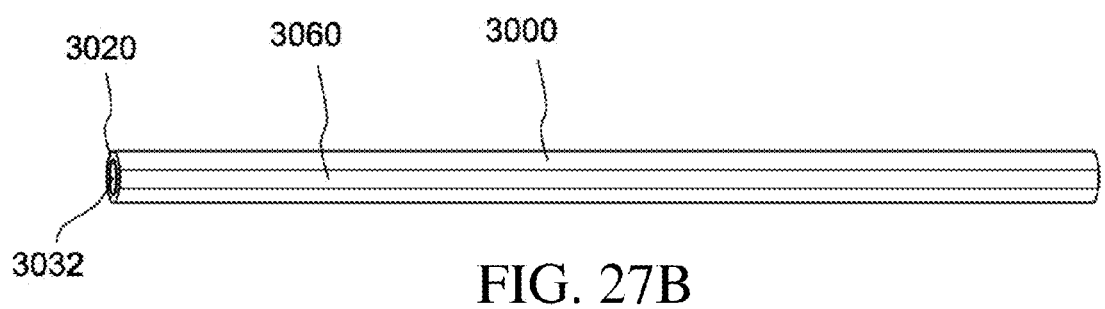
FIG. 27B shows an embodiment of the sampling hub lumen with a non-expanded elastomeric lumen.

FIG. 27B shows the sampling hub lumen 3000 with an elastomeric strip 3060 throughout the longitudinal side of the lumen. The elastomeric strip can be expanded which increases the inner diameter of the sampling hub lumen 3000.

Figure 27C:
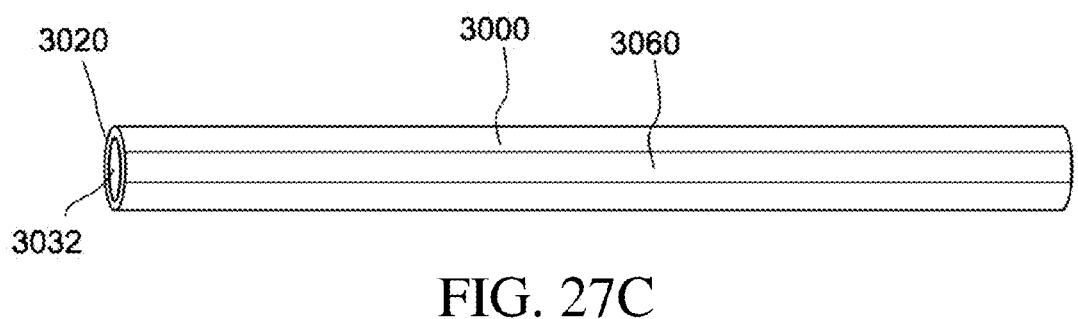
FIG. 27C. shows an embodiment of the sampling hub lumen with an expanded elastomeric lumen.

FIG. 27C shows the elastomeric strip 3060 expanded and an increased lumen diameter.

Figure 27D:
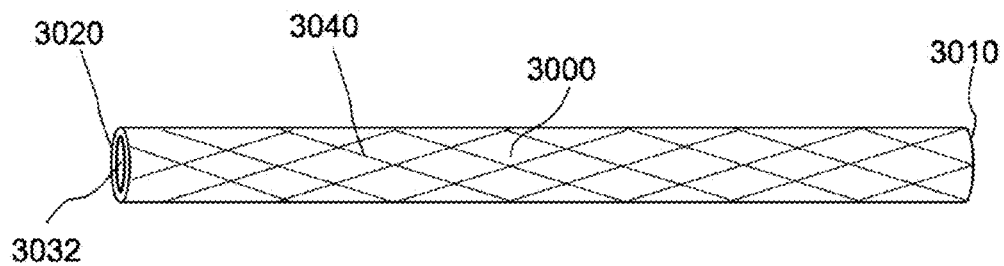
FIG. 27D shows an embodiment of the sampling hub lumen with a non-expanded braided lumen.

FIG. 27D shows a braid 3040 throughout the sampling hub lumen 3000.

Figure 27E:
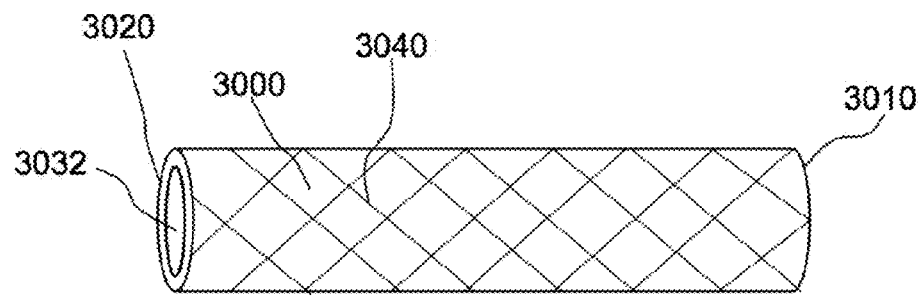
FIG. 27E shows an embodiment of the sampling hub lumen with an expanded braided lumen.

FIG. 27E shows a shortened lumen 3000 with an increased diameter. In this figure the braid 3040 is expanded which causes the change in geometry.

Figure 27F:
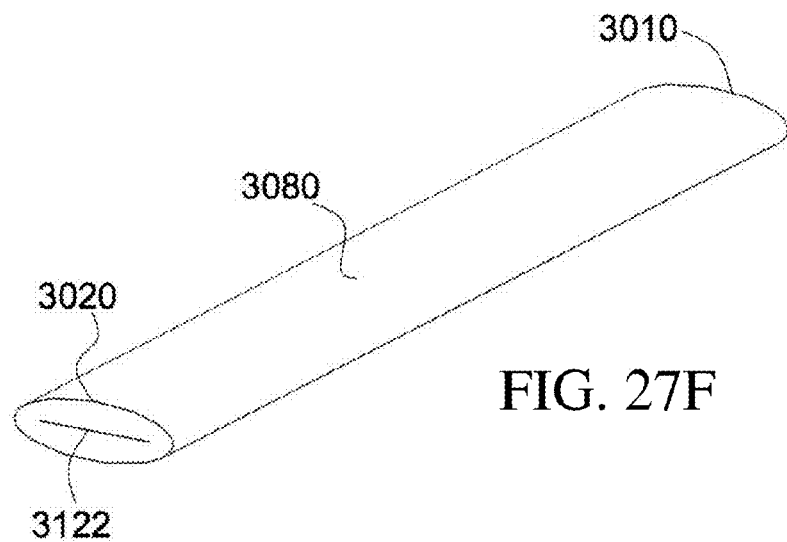
FIG. 27F shows an embodiment of the sampling hub lumen with a non-expanded flat lumen.

FIG. 27F shows a flat lumen 3080. The distal 3020 and proximal 3010 ends of this lumen contains a slit 3122.

Figure 28:
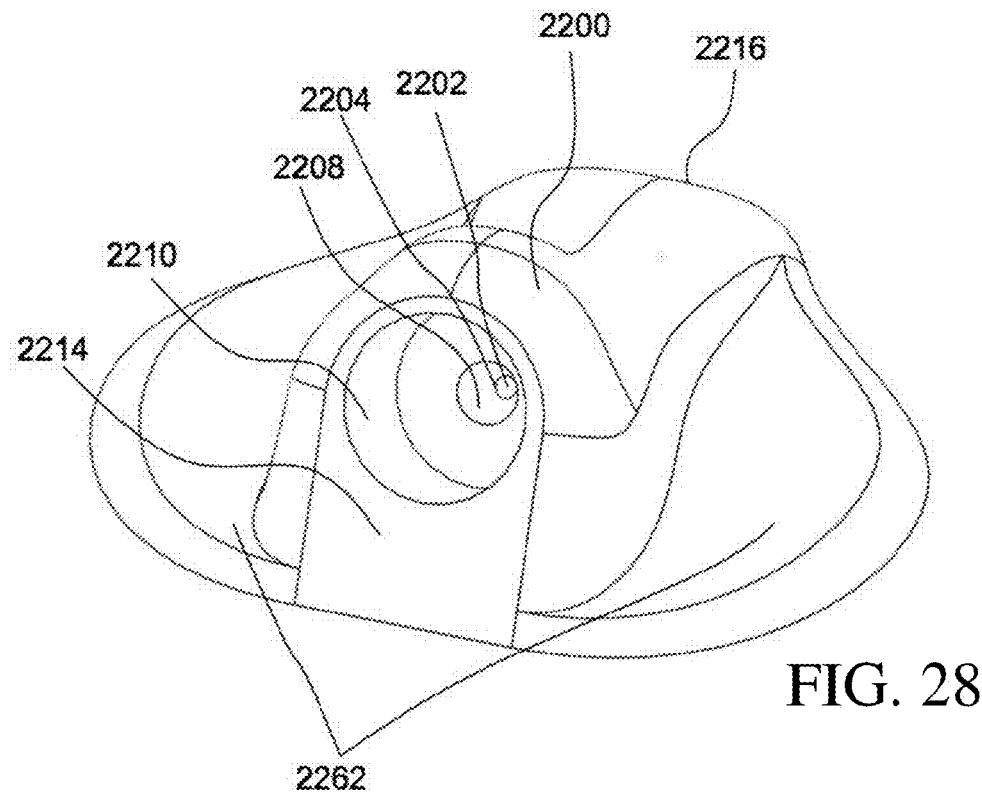
FIG. 28 shows a perspective view of an embodiment of the sampling hub with support wings.

FIG. 28 shows a sampling hub 2200 with support wings 2262 incorporated for added support. The geometry of the catheter body is such as to prevent mistaking the described sampling hub with other catheter embodiments currently on the market. An internal chamber 2202 can house a lumen with its proximal end 2204 against the internal probe alignment chamber 2208. These elements are accessed through an internal chamber for a proximal valve 2210 which creates a barrier with the external environment. In the preferred embodiment this barrier may be a split septum. There is a downward slope from the proximal catheter end 2214 to the distal catheter end 2216.

Figure 29:
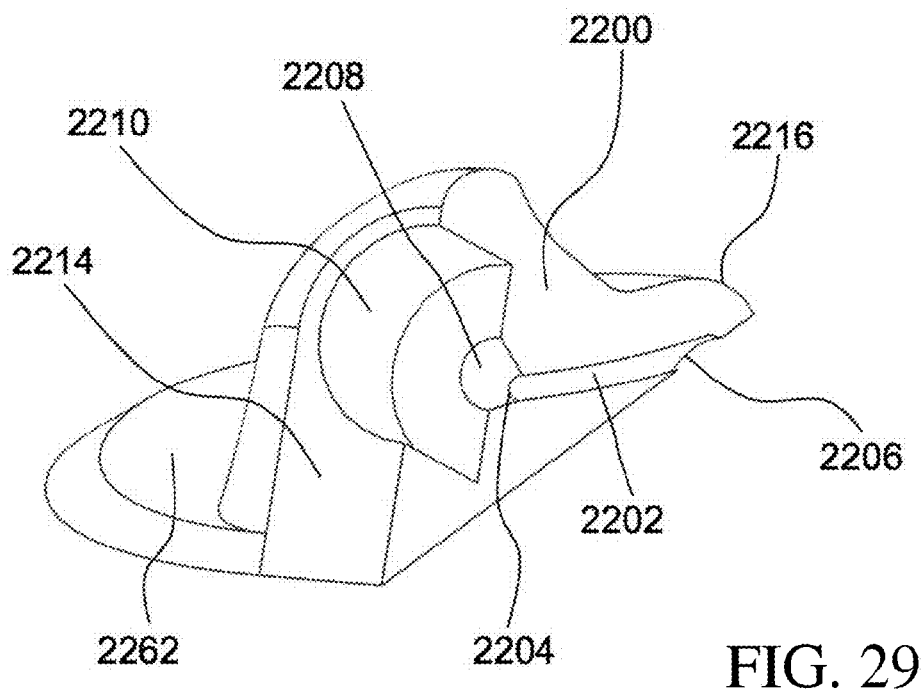
FIG. 29 shows a cross section view of an embodiment of the sampling hub with support wings and bottom catheter exit point.

FIG. 29 shows a cross-section of the sampling hub 2200. The distal end of the lumen chamber 2206 exits the sampling hub at its bottom. This figure clearly displays the downward guidance slope of the internal chamber 2202 from the internal probe alignment chamber 2208 to the distal end chamber for catheter lumen 2206.

Figure 30:
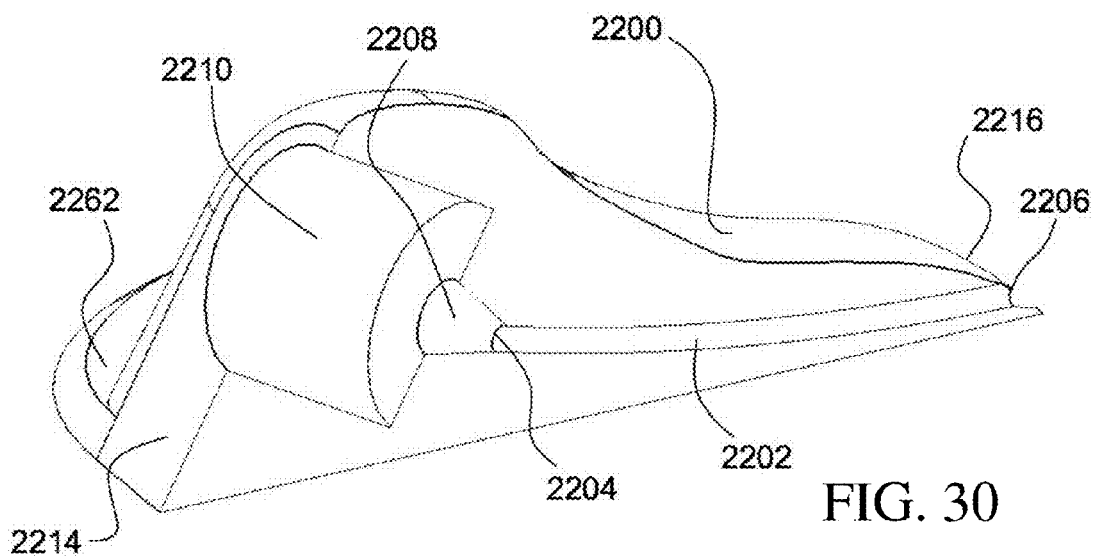
FIG. 30 shows a cross section view of a cross section view of the sampling hub with wings and distal catheter exit point.

FIG. 30 shows a cross-section of the sampling hub 2200. The distal end of the lumen chamber 2206 exits the sampling hub at its distal end. This figure clearly displays the downward guidance slope of the internal chamber 2202 from the internal probe alignment chamber 2208 to the distal end chamber for catheter lumen 2206.

Figure 31:
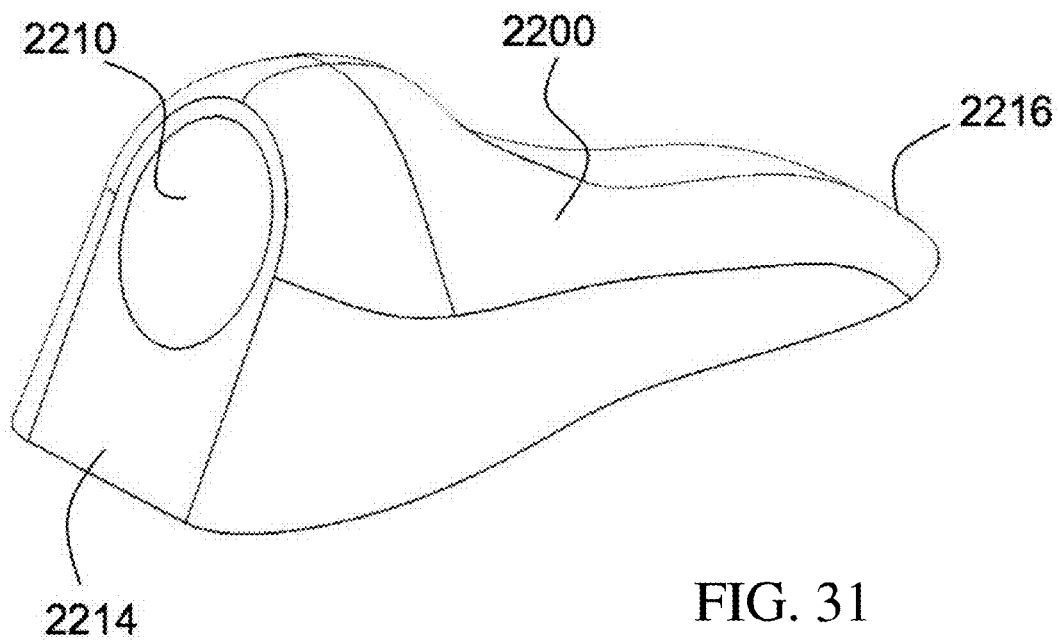
FIG. 31 shows a perspective view of an embodiment of the sampling hub.

FIG. 31 shows a perspective view of another sampling hub embodiment. Surface curvature in the sampling cannula is shown.

Figure 32:
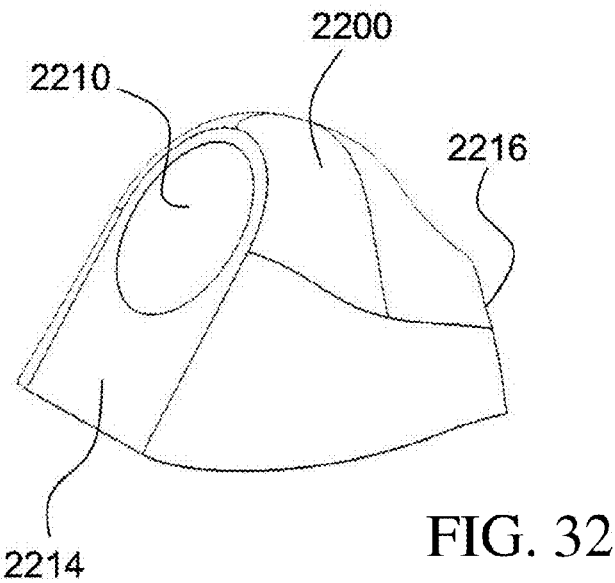
FIG. 32 shows a perspective view of an embodiment of the sampling hub with a shortened distal end.

FIG. 32 shows a perspective view of another sampling hub embodiment with a shortened distal end 2216.

Figure 33:
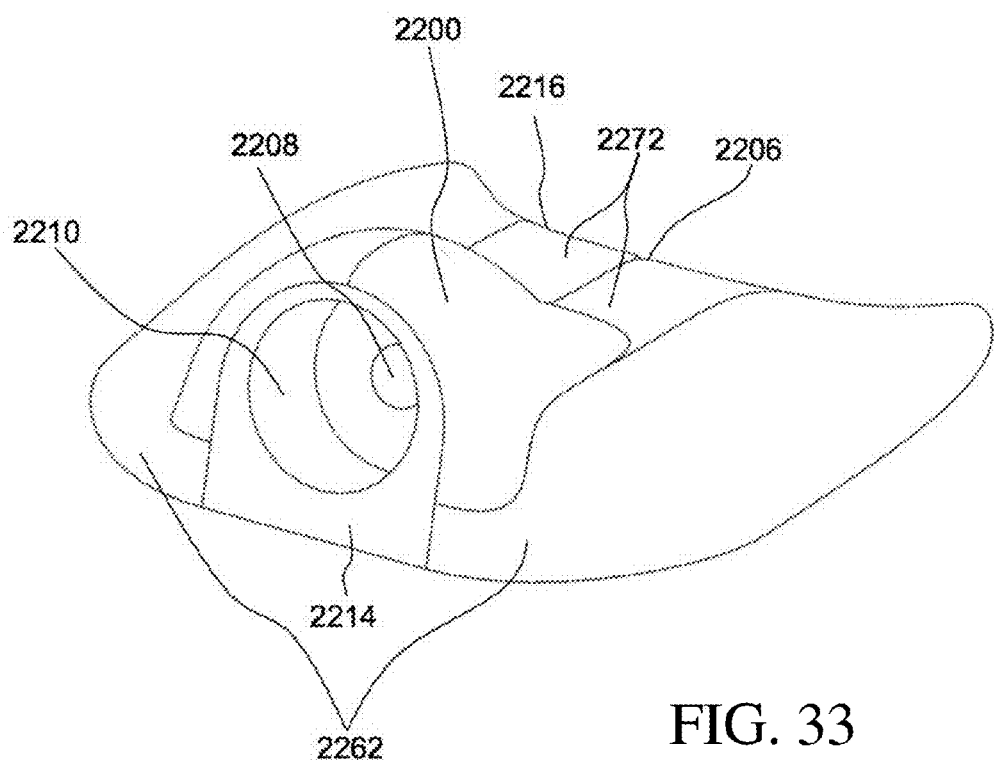
FIG. 33 shows a perspective view of an embodiment of the sampling hub with extended support wings and a clear viewing panel on the distal end.

FIG. 33 shows a perspective view of another sampling hub embodiment with extended support wings and clear viewing panels 2272 so that the positioning of the sampling cannula 1500 or other device through the sampling hub 2200 can be viewed. The clear viewing panels 2272 can also be used to view where the sampling hub lumen 3000 penetrates a distal environment.

Figure 34:
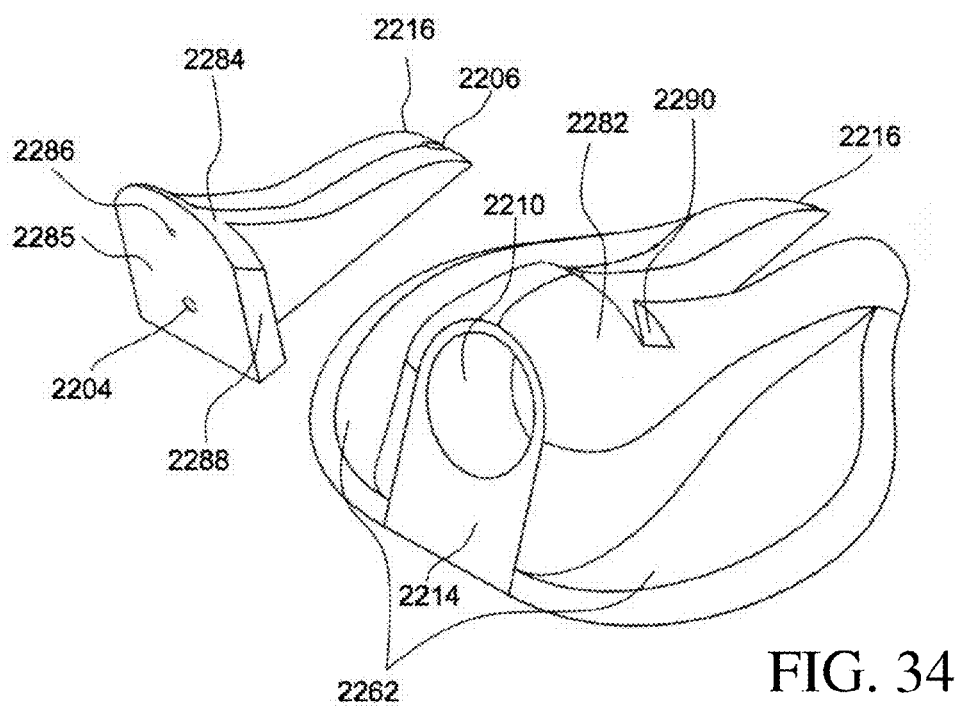
FIG. 34 shows a perspective disassembled view of a two part sampling hub embodiment.

FIG. 34 is an exploded view of a two part sampling hub embodiment. The distal part 2284 houses the entire lumen chamber with the chamber's distal end 2204 at the proximal end of the distal part 2285. The distal part contains a ledge 2288 for alignment within the proximal sampling hub part 2282 and a locking knob 2286 so it is held in place after insertion. The proximal sampling hub part 2282 is configured to receive the distal sampling hub part alignment ledge 2288 within its internal alignment chamber 2290.

Figure 35:
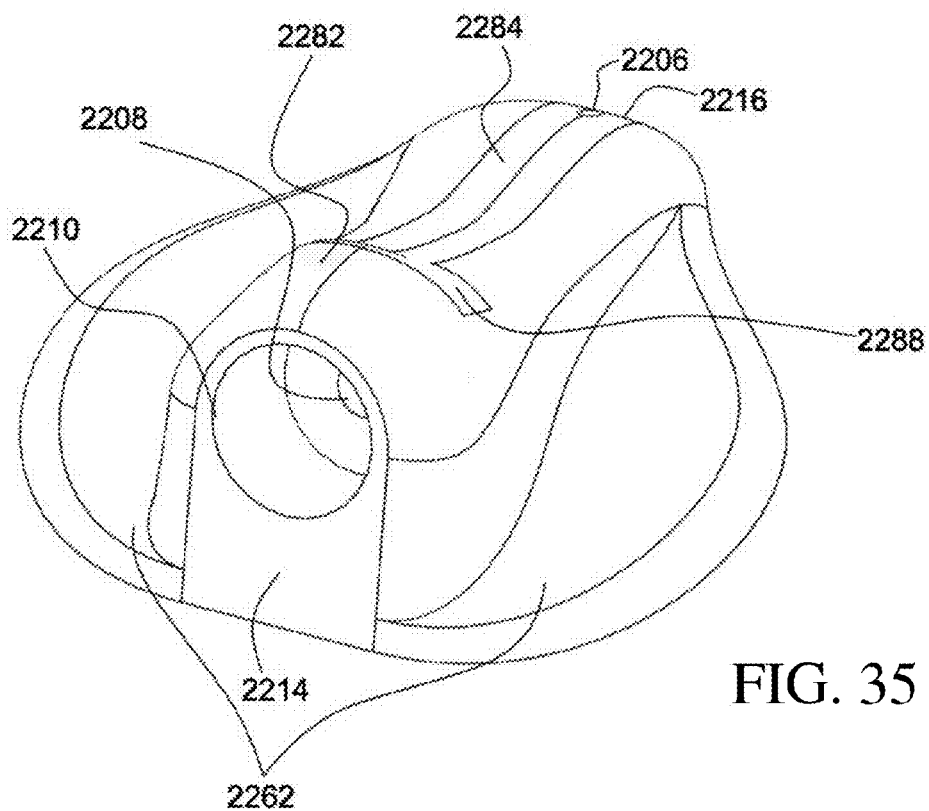
FIG. 35 shows a perspective assembled view of a two part sampling hub.

FIG. 35 is a perspective view of a two part sampling hub embodiment. The distal sampling hub part 2284 is shown within the proximal sampling hub component 2282.

Figure 36:
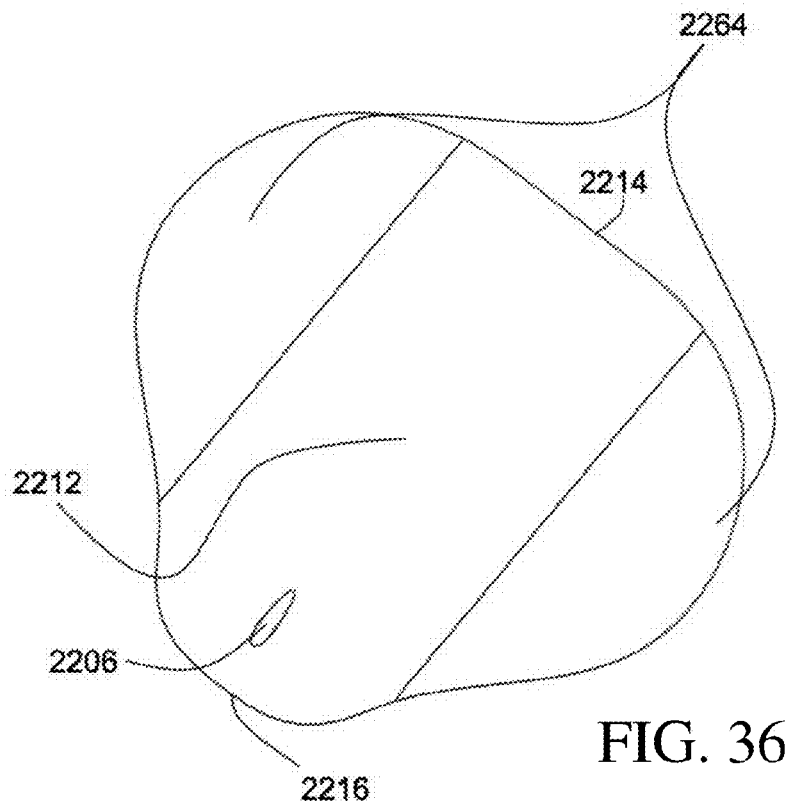
FIG. 36 shows an embodiment of the bottom of a winged sampling hub embodiment.

FIG. 36 is a view of the bottom segment of a sampling hub embodiment. The flat wing bottoms 2264, flat bottom of the sampling hub 2212, and the distal end of the lumen chamber 2206 are shown. The flat bottoms 2264 and 2212 would lie against the surface into which the liquid sampler (not shown) is positioned, as lying flat against the surface of a patient. The flat bottoms 2264 and 2212 may be independently rigid or flexible. When flat and rigid, the flat surfaces may apply pressure against the patient and underlying tissue to have the skin conform to the flat surface and have the chamber for the catheter lumen 2206 in a secure alignment on the skin and in alignment with the desired target area for retrieving liquid through the lumen (not shown).

Figure 37:
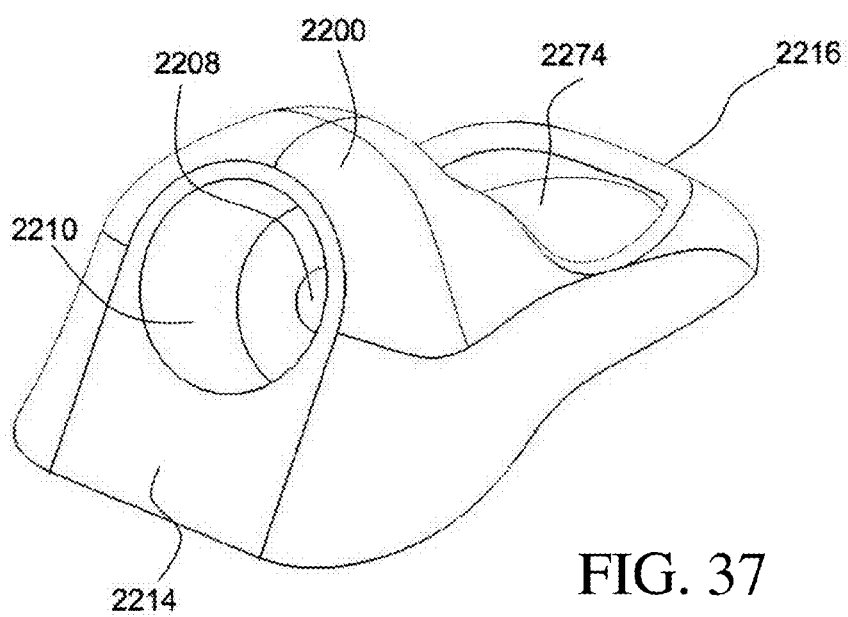
FIG. 37 shows a perspective view of an embodiment of the sampling hub with a distal through hole.

FIG. 37 is a perspective view of a sampling hub embodiment with distal visualization window 2274. The window may be a transparent or translucent layer or merely an opening, without substance therein.

It should be appreciated that various sizes, dimensions, contours, rigidity, shapes, flexibility and materials of any of the components or portions of components in the various embodiments discussed throughout may be varied and utilized as desired or required. Similarly, locations and alignments of the various components may vary as desired or required.

It should be appreciated that any of the components or modules referred to with regards to any of the present invention embodiments discussed herein, may be integrally or separately formed with one another. Further, redundant functions or structures of the components or modules may be implemented.

It should be appreciated that the device and related components discussed herein may take on all shapes along the entire continual geometric spectrum of manipulation of x, y and z planes to provide and meet the anatomical and structural demands and operational requirements. Moreover, locations and alignments of the various components may vary as desired or required.

An embodiment of the present invention provides a medical blood sampling catheter device that provides a simple, fast, and painless procedure for periodic access to small amounts of an accurate blood source. Unlike other blood sampling devices, certain embodiments of this device minimize the quantity of high quality blood drawn, and can optimize this quantity for a variety of analyte sampling tests.

A liquid sampling device within the scope of the present technology may include a delivery catheter and a sampling cannula, wherein the sampling cannula is located within a lumen of the delivery catheter and has a longitudinal axis, the delivery catheter being moveable over the sampling cannula by retraction or extension of the delivery catheter. The sampling device may have two extreme relative positions of the delivery catheter and the sampling cannula are available, a first extreme position where the delivery catheter shields at least the majority of sampling port(s) in the sampling cannula from exposure to an adjacent environment along the longitudinal axis of the sampling cannula and a second extreme position wherein the delivery catheter has moved rearwardly and exposes the majority of sampling port(s) in the sampling cannula to an adjacent environment.

Sampling ports may be present along the longitudinal axis of the sampling cannula and at least some of the ports are substantially perpendicular to the longitudinal axis of the sampling cannula. The sampling device may have sampling ports are present along the longitudinal axis of the sampling cannula and at least some of the ports are perpendicular to the longitudinal axis of the sampling cannula and in the first extreme position, at least some of the sampling ports are shielded from the adjacent environment and in the second extreme position, at least one or more of the sampling ports are exposed to the adjacent environment.

The sampling cannula may support a catheter hub that surrounds a front end of the sampling cannula, the sampling hub providing a sealed insertion port physically insulating intake ports in the sampling cannula from exposure to an adjacent environment. The sampling device may have two extreme relative positions of the delivery catheter and the sampling cannula are available, a first extreme position where the delivery catheter shields at least the majority of sampling ports in the sampling cannula from exposure to an adjacent environment along the longitudinal axis of the sampling cannula and a second extreme position wherein the delivery catheter has moved rearwardly and exposed to the adjacent environment the majority of sampling ports in the sampling cannula, and wherein movement of the delivery catheter from the first extreme position to the second extreme position causes the catheter hub to cover the longitudinal axis of the sampling cannula and expose at least some of the intake ports in the sampling cannula to the adjacent environment.

The sampling cannula may have a volume therein to hold liquid samples, and there is a port at a proximal end of the volume to allow controlled passage of liquid within the volume to be withdrawn into a modular sampling component.

The sampling device may have the sampling cannula relative to the forward and rearward movement of the delivery catheter after the delivery catheter has been positioned within a body of a patient, the sampling cannula comprises a volume therein to hold tissue samples, and there is a port at a proximal end of the volume to allow controlled retention of solid within the volume to be withdrawn into a modular sampling component. The sampling device may have a proximal support element is present to resist forward and rearward movement of the sampling cannula within the delivery catheter. Upon withdrawal of the delivery catheter and retention of a forward position by the sampling cannula, a chamber may be formed at a proximal end of the sampling cannula and reduced pressure or other extraction methods is applied within a volume of the sampling cannula to draw liquid samples from the adjacent environment into the volume through the ports exposed to the adjacent environment.

A method of sampling liquids from within a patient may have steps of:
a) inserting a sampling device into a region of a patient, the sampling device comprising a delivery catheter and sampling cannula located within a lumen of the delivery catheter and having a longitudinal axis, the delivery catheter being moveable over the sampling cannula by retraction or extension of the delivery catheter;
b) moving the delivery catheter towards a target volume of the patient causing a retraction of the delivery catheter, thereby exposing the sampling cannula to the target volume of the patient;
c) allowing liquid within the target volume of the patient into the sampling cannula; and
d) withdrawing the liquid from the sampling cannula to create a liquid sample.

The sampling cannula may be inserted through the skin or other barrier into a target area within the patient, the sampling cannula is positioned at a forward location within the patient, the delivery catheter is withdrawn from the forward location and the sampling cannula remains at the forward location.

A support element within the sampling device may support a proximal end of the sampling cannula so as to resist withdrawal from the forward location by any friction between the delivery catheter and the sampling cannula.

The sampling cannula may have at least one liquid inflow port along its longitudinal axis and movement of the delivery catheter away from the target area increases exposure of the at least one delivery port to liquid within the target area of the patient.

In the method there may be multiple liquid inflow ports along the longitudinal axis of the sampling cannula and movement of the delivery catheter away from the target area increases exposure of the multiple delivery ports to liquid within the target area of the patient and then liquid is drawn into the sampling cannula through the multiple delivery ports.

In method, the sampling cannula may support a sampling hub that surrounds a front end of the sampling cannula, the sampling hub providing a sealed insertion port physically insulating the sampling cannula from liquid in the target area within the patient, and the sampling hub covers the sampling cannula before the liquid is withdrawn. In this type of method, the retraction of the delivery catheter may simultaneously cause the sampling hub to cover the sampling cannula and upon full insertion exposes the sampling cannula to liquid within the target area of the patient.

Although specific materials, dimensions and designs have been provided to enable practice of the present technology, this specific disclosure is to be understood as support for the generic concepts recited herein and are not intended to limit the generic scope of the claims. Variations, equivalents and alternatives to the specifics will be understood by those skilled in the art in this light.

The invention claimed is:

1. A method of sampling liquids from within a patient comprising:
a) inserting a sampling device into a region within a patient, the sampling device comprising a delivery catheter and sampling cannula located within a lumen of the delivery catheter and having a longitudinal axis, the delivery catheter being moveable over the sampling cannula by retraction or extension of the delivery catheter;
b) moving the sampling cannula towards a target volume of the patient causing a retraction of the delivery catheter relative to the sampling cannula, thereby exposing the sampling cannula to the target volume of the patient; and
c) allowing liquid within the target volume of the patient into the sampling cannula;
wherein inserting the sampling device comprises (i) transitioning a proximal valve of a sampling hub from a closed state to an open state by inserting a distal end of the delivery catheter and the sampling cannula at least partially through the proximal valve and (ii) inserting the sampling cannula through a distal valve and distal end of the sampling hub while the distal end of the delivery catheter remains proximal to the distal valve;
wherein inserting the sampling device further comprises positioning the sampling cannula and the delivery catheter to be entirely proximal to the sampling hub while the sampling cannula is located within the lumen of the delivery catheter.

2. The method of claim 1 wherein the sampling cannula is inserted into a target area at a forward location within the patient, and the delivery catheter is withdrawn while the sampling cannula remains at the forward location.

3. The method of claim 2 wherein a support element within the sampling device supports a proximal end of the sampling cannula so as to resist withdrawal from the forward location by any friction between the delivery catheter and the sampling cannula.

4. The method of claim 3 wherein the sampling cannula comprises multiple inflow ports along the longitudinal axis of the sampling cannula, movement of the delivery catheter away from the target area increases exposure of the multiple inflow ports to liquid within the target area of the patient, and liquid is drawn into the sampling cannula through the multiple inflow ports.

5. The method of claim 4 wherein the retraction of the delivery catheter simultaneously causes the sampling hub to cover the sampling cannula and upon full insertion exposes the sampling cannula to liquid within the target area of the patient.

6. The method of claim 2 wherein the sampling cannula has at least one inflow port along its longitudinal axis and movement of the delivery catheter away from the target area increases exposure of the at least one inflow port to liquid within the target area of the patient.

7. The method of claim 2 wherein the sampling cannula supports the sampling hub that surrounds a front end of the sampling cannula, the sampling hub providing a sealed insertion port physically insulating the sampling cannula from liquid in the target area within the patient, and the sampling hub covers the sampling cannula before the liquid is withdrawn.

8. The method of claim 1 wherein the sampling cannula is inserted through the sampling hub into a target area at a forward location within the patient, and the delivery catheter is withdrawn while the sampling cannula remains at the forward location.

9. The method of claim 1 further comprising inserting a distal end of the sampling cannula through a distal valve of the hub.

10. The method of claim 9 wherein the distal valve is positioned at the region within the patient.

11. The method of claim 9 wherein the distal valve is a distal septum.

12. The method of claim 1 wherein moving the delivery catheter further comprises advancing the delivery catheter through a proximal chamber of the hub, distal to the proximal valve, until the distal end of the delivery catheter abuts a proximal end of a distal chamber of the hub.

13. The method of claim 1 further comprising advancing the distal end of the sampling cannula until a proximal end of the delivery catheter abuts a proximal end of an outer sheath.

14. The method of claim 13 wherein the outer sheath houses the delivery catheter and is connected to the sampling cannula.

15. The method of claim 1 further comprising, withdrawing the sampling cannula proximally into the delivery catheter while the delivery catheter is held by the proximal valve until the sampling cannula is within the lumen of the delivery catheter.

16. The method of claim 1 wherein the proximal valve is positioned outside the patient.

17. The method of claim 1 wherein the proximal valve is a proximal septum.

18. The method of claim 1 wherein the sampling hub contains a coating of a hydrophobic or hydrophilic material.

19. A method comprising:
   a) inserting a probe device into a region within a patient, the probe device comprising a delivery catheter and a cannula located within a lumen of the delivery catheter and having a longitudinal axis, the delivery catheter being moveable over the cannula by retraction or extension of the delivery catheter;
   b) moving the cannula towards a target volume of the patient causing a retraction of the delivery catheter relative to the cannula, thereby exposing the cannula to the target volume of the patient; and
   c) placing the target volume of the patient in fluid communication with a lumen of the cannula;
   wherein inserting the probe device comprises (i) transitioning a proximal valve of a hub from a closed state to an open state by inserting a distal end of the delivery catheter and the cannula at least partially through the proximal valve and (ii) inserting the cannula through a distal valve and a distal end of the hub while the distal end of the delivery catheter remains proximal to the distal valve;
   wherein inserting the probe device further comprises positioning the cannula and the delivery catheter to be entirely proximal to the hub while the cannula is located within the lumen of the delivery catheter.

20. The method of claim 19 further comprising: delivering, with the cannula, a therapy to the target volume.

21. The method of claim 20 wherein the therapy is an electric shock.

22. The method of claim 19 wherein the probe device further comprises a syringe having a plunger.

23. The method of claim 19 further comprising: allowing liquid within the target volume of the patient into the cannula.

24. The method of claim 19 wherein the distal valve is positioned at the region within the patient.

25. The method of claim 19 wherein the distal valve is a distal septum.

26. The method of claim 19 wherein the cannula is inserted into a target area at a forward location within the patient, and the delivery catheter is withdrawn while the cannula remains at the forward location.

27. The method of claim 26 wherein a support element within the probe device supports a proximal end of the cannula so as to resist withdrawal from the forward location by any friction between the delivery catheter and the cannula.

28. The method of claim 19 wherein moving the delivery catheter further comprises advancing the delivery catheter through a proximal chamber of the hub, distal to the proximal valve, until the distal end of the delivery catheter abuts a proximal end of a distal chamber of the hub.

29. The method of claim 19 further comprising, withdrawing the cannula proximally into the delivery catheter while the delivery catheter is held by the proximal valve until the cannula is within the lumen of the delivery catheter.

30. The method of claim 19 wherein the hub contains a coating of a hydrophobic or hydrophilic material.

31. A method of sampling liquids from within a patient comprising:
   a) inserting a sampling device into a region within a patient, the sampling device comprising a delivery catheter and sampling cannula located within a lumen of the delivery catheter and having a longitudinal axis, the delivery catheter being moveable over the sampling cannula by retraction or extension of the delivery catheter;
   b) moving the sampling cannula towards a target volume of the patient causing a retraction of the delivery catheter relative to the sampling cannula, thereby exposing the sampling cannula to the target volume of the patient; and
   c) allowing liquid within the target volume of the patient into the sampling cannula;
   wherein inserting the sampling device comprises (i) transitioning a proximal valve of a sampling hub from a closed state to an open state by inserting a distal end of the delivery catheter and the sampling cannula at least partially through the proximal valve and (ii) inserting the sampling cannula through a distal valve and distal end of the sampling hub while the distal end of the delivery catheter remains proximal to the distal valve;
   wherein the sampling device further comprises an outer body with the delivery catheter being located within a body chamber of the outer body, the sampling cannula being secured to the outer body, the delivery catheter being moveable over the sampling cannula by retraction or extension of the delivery catheter, and the sampling cannula having a length that is shorter than a combined length of the outer body and the delivery catheter.

32. The method of claim 31 wherein the sampling cannula is inserted into a target area at a forward location within the patient, and the delivery catheter is withdrawn while the sampling cannula remains at the forward location.

33. The method of claim 31 wherein the sampling cannula is inserted through the sampling hub into a target area at a forward location within the patient, and the delivery catheter is withdrawn while the sampling cannula remains at the forward location.

34. The method of claim 33 wherein a support element within the sampling device supports a proximal end of the sampling cannula so as to resist withdrawal from the forward location by any friction between the delivery catheter and the sampling cannula.

35. The method of claim 33 wherein the sampling cannula has at least one inflow port along its longitudinal axis and movement of the delivery catheter away from the target area increases exposure of the at least one inflow port to liquid within the target area of the patient.

36. The method of claim 35 wherein the sampling cannula comprises multiple inflow ports along the longitudinal axis of the sampling cannula, movement of the delivery catheter away from the target area increases exposure of the multiple inflow ports to liquid within the target area of the patient, and liquid is drawn into the sampling cannula through the multiple inflow ports.

37. The method of claim 33 wherein the sampling cannula supports the sampling hub that surrounds a front end of the sampling cannula, the sampling hub providing a sealed insertion port physically insulating the sampling cannula from liquid in the target area within the patient, and the sampling hub covers the sampling cannula before the liquid is withdrawn.

38. The method of claim 37 wherein the retraction of the delivery catheter simultaneously causes the sampling hub to cover the sampling cannula and upon full insertion exposes the sampling cannula to liquid within the target area of the patient.

39. The method of claim 31 further comprising inserting a distal end of the sampling cannula through a distal valve of the hub.

40. The method of claim 39 wherein the distal valve is positioned at the region within the patient.

41. The method of claim 39 wherein the distal valve is a distal septum.

42. The method of claim 31 wherein moving the delivery catheter further comprises advancing the delivery catheter through a proximal chamber of the hub, distal to the proximal valve, until the distal end of the delivery catheter abuts a proximal end of a distal chamber of the hub.

43. The method of claim 31 further comprising advancing the distal end of the sampling cannula until a proximal end of the delivery catheter abuts a proximal end of an outer sheath.

44. The method of claim 43 wherein the outer sheath houses the delivery catheter and is connected to the sampling cannula.

45. The method of claim 31 further comprising, withdrawing the sampling cannula proximally into the delivery catheter while the delivery catheter is held by the proximal valve until the sampling cannula is within the lumen of the delivery catheter.

46. The method of claim 31 wherein the proximal valve is positioned outside the patient.

47. The method of claim 31 wherein the proximal valve is a proximal septum.

48. The method of claim 31 wherein the sampling hub contains a coating of a hydrophobic or hydrophilic material.

49. A method comprising:
  a) inserting a probe device into a region within a patient, the probe device comprising a delivery catheter and a cannula located within a lumen of the delivery catheter and having a longitudinal axis, the delivery catheter being moveable over the cannula by retraction or extension of the delivery catheter;
  b) moving the cannula towards a target volume of the patient causing a retraction of the delivery catheter relative to the cannula, thereby exposing the cannula to the target volume of the patient; and
  c) placing the target volume of the patient in fluid communication with a lumen of the cannula;
  wherein inserting the probe device comprises (i) transitioning a proximal valve of a hub from a closed state to an open state by inserting a distal end of the delivery catheter and the cannula at least partially through the proximal valve and (ii) inserting the cannula through a distal valve and a distal end of the hub while the distal end of the delivery catheter remains proximal to the distal valve;
  wherein the probe device further comprises an outer body with the delivery catheter being located within a body chamber of the outer body, the cannula being secured to the outer body, the delivery catheter being moveable over the cannula by retraction or extension of the delivery catheter, and the cannula having a length that is shorter than a combined length of the outer body and the delivery catheter.

50. The method of claim 49 further comprising: delivering, with the cannula, a therapy to the target volume.

51. The method of claim 50 wherein the therapy is an electric shock.

52. The method of claim 49 wherein the probe device further comprises a syringe having a plunger.

53. The method of claim 49 further comprising: allowing liquid within the target volume of the patient into the cannula.

54. The method of claim 49 wherein the distal valve is positioned at the region within the patient.

55. The method of claim 49 wherein the distal valve is a distal septum.

56. The method of claim 49 wherein the cannula is inserted into a target area at a forward location within the patient, and the delivery catheter is withdrawn while the cannula remains at the forward location.

57. The method of claim 56 wherein a support element within the probe device supports a proximal end of the cannula so as to resist withdrawal from the forward location by any friction between the delivery catheter and the cannula.

58. The method of claim 49 wherein moving the delivery catheter further comprises advancing the delivery catheter through a proximal chamber of the hub, distal to the proximal valve, until the distal end of the delivery catheter abuts a proximal end of a distal chamber of the hub.

59. The method of claim 49 further comprising, withdrawing the cannula proximally into the delivery catheter while the delivery catheter is held by the proximal valve until the cannula is within the lumen of the delivery catheter.

60. The method of claim 49 wherein the hub contains a coating of a hydrophobic or hydrophilic material.

\* \* \* \* \*